United States Patent
Hudalla et al.

(10) Patent No.: US 12,152,088 B2
(45) Date of Patent: *Nov. 26, 2024

(54) CO-ASSEMBLY PEPTIDES, NANOSTRUCTURES, AND METHODS OF MAKING AND USING THE SAME

(71) Applicant: University of Florida Research Foundation, Incorporated, Gainesville, FL (US)

(72) Inventors: Gregory Allan Hudalla, Gainesville, FL (US); Dillon T. Seroski, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 208 days.

This patent is subject to a terminal disclaimer.

(21) Appl. No.: 17/124,384

(22) Filed: Dec. 16, 2020

(65) Prior Publication Data

US 2021/0107943 A1 Apr. 15, 2021

Related U.S. Application Data

(63) Continuation of application No. 15/672,783, filed on Aug. 9, 2017, now Pat. No. 10,906,939.

(60) Provisional application No. 62/464,526, filed on Feb. 28, 2017, provisional application No. 62/372,427, filed on Aug. 9, 2016.

(51) Int. Cl.
  *C07K 7/08* (2006.01)
  *C07K 1/02* (2006.01)
  *C07K 1/113* (2006.01)
  *C07K 7/06* (2006.01)

(52) U.S. Cl.
  CPC ............... *C07K 7/08* (2013.01); *C07K 1/02* (2013.01); *C07K 1/1136* (2013.01); *C07K 7/06* (2013.01); *C07K 2319/00* (2013.01); *C07K 2319/21* (2013.01); *C07K 2319/50* (2013.01); *C07K 2319/60* (2013.01); *C07K 2319/735* (2013.01)

(58) Field of Classification Search
  None
  See application file for complete search history.

(56) References Cited

U.S. PATENT DOCUMENTS 10,906,939 B2 2/2021 Hudalla et al.
2013/0012457 A1 1/2013 Boden et al.

OTHER PUBLICATIONS

Baldwin et al., Cytochrome display on amyloid fibrils. J Am Chem Soc. 2006, 128(7): 2162-3.
Baxa et al, Mechanism of inactivation on prion conversion of the *Saccharomyces cerevisiae* Ure2 protein. Proc Natl Acad Sci U S A. 2002;99(8):5253-60.
Black et al., Self-assembled peptide amphiphile micelles containing a cytotoxic T-cell epitope promote a protective immune response in vivo. Adv Mater. 2012; 24(28): 3845-9.
Chen et al., The use of self-adjuvanting nanofiber vaccines to elicit high-affinity B cell responses to peptide antigens without inflammation. Biomaterials. 2013; 34: 8776-85.
Chow et al., Self-assembling nanostructures to deliver angiogenic factors to pancreatic islets. Biomaterials. 2010; 31 (24): 6154-61.
Collier et al., Enzymatic modification of self-assembled peptide structures with tissue transglutaminase. Bioconjug Chem. 2003; 14(4): 748-55.
Collier et al., Multi-component extracellular matrices based on peptide self-assembly. Chem Soc Rev. 2010; 39(9): 3413-24.
Davis et al., Injectable self-assembling peptide nanofibers create intramyocardial microenvironments for endothelial cells. Circulation. 2005; 111(4): 442-50.
Davis et al., Local myocardial insulin-like growth factor 1 (IGF-1) delivery with biotinylated peptide nanofibers improves cell therapy for myocardial infarction. Proc Natl Acad Sci U S A. 2006; 103(21): 8155-60.
Du et al., Supramolecular Hydrogelators and Hydrogels: From Soft Matter to Molecular Biomaterials. Chem Rev. 2015; 115(24): 13165-307.
Fettis et al., Microgels with tunable affinity-controlled protein release via desolvation of self-assembled peptide nanofibers, J Mater. Chem. B 2016, 4, 3054-3064.
Guler et al., Presentation and recognition of biotin on nanofibers formed by branched peptide amphiphiles. Nano Lett. 2005; 5(2): 249-52.
Haines-Butterick et al., In vitro assessment of the pro-inflammatory potential of beta-hairpin peptide hydrogels. Biomaterials. 2008; 29(31): 4164-9.
Holmes et al., Extensive neurite outgrowth and active synapse formation on self-assembling peptide scaffolds. Proc Natl Acad Sci U S A. 2000; 97(12): 6728-33.
Hsieh et al., Controlled delivery of PDGF-BB for myocardial protection using injectable self-assembling peptide nanofibers. J Clin Invest. 2006; 116(1): 237-48.
Hudalla et al., Gradated assembly of multiple proteins into supramolecular nanomaterials. Nat Mater. 2014; 13(8): 829-36.
Jung et al., Co-assembling peptides as defined matrices for endothelial cells. Biomaterials. 2009; 30(12): 2400-10.

(Continued)

*Primary Examiner* — Thomas S Heard

(74) *Attorney, Agent, or Firm* — Wolf, Greenfield & Sacks, P.C.

(57) ABSTRACT

Provided herein are charge complementary peptides that can be optionally coupled to a cargo polypeptide that are capable of self-assembling under stimulating conditions. The charge complementary peptides can be capable of forming supramolecular structures. Also provided herein are methods of using the charge complementary peptides provided herein.

20 Claims, 60 Drawing Sheets

Specification includes a Sequence Listing.

(56) References Cited

OTHER PUBLICATIONS

Khan et al., Post-assembly functionalization of supramolecular nanostructures with bioactive peptides and fluorescent proteins by native chemical ligation. Bioconjug Chem. 2014; 25(4): 707-17.

King et al., A modular self-assembly approach to functionalized .beta.-sheet peptide hydrogel biomaterials. Royal Society of Chemistry. Soft matter, 2016. 1915-1923.

Kyle et al., Rational molecular design of complementary self-assembling peptide hydrogels. Adv Healthc Mater. 2012; 1(5): 640-5.

Lee et al. Bone regeneration with low dose BMP-2 amplified by biomimetic supramolecular nanofibers within collagen scaffolds. Biomaterials. 2013; 34(2): 452-9.

Lee et al. Gel scaffolds of BMP-2-binding peptide amphiphile nanofibers for spinal arthrodesis. Adv Healthc Mater. 2015;4(1)131-41.

Leng et al., Integration of a Fluorescent Molecular Biosensor into Self-Assembled Protein Nanowires: A Large Sensitivity Enhancement. Angew Chem Int Edit. 2010;49(40):7243-6.

Mahmoud et al., Bioorthogonal dual functionalization of self-assembling peptide fibers. Biomaterials. 2011;32 (15):3712-20.

Matsumura et al., Uemura S, Mihara H. Construction of biotinylated peptide nanotubes for arranging proteins. Mol Biosyst. 2005; 1(2): 146-8.

Mehrban et al., Assessing cellular response to functionalized alpha-helical peptide hydrogels. Adv Healthc Mater. 2014;3(9)1387-91.

Men et al., Seeding-induced self-assembling protein nanowires dramatically increase the sensitivity of immunoassays. Nano Lett. 2009; 9(6): 2246-50.

Miyachi et al., Peptide nanofibers modified with a protein by using designed anchor molecules bearing hydrophobic and functional moieties. Chemistry. 2010;16(22):6644-50.

Pompano et al., Titrating T-cell epitopes within self-assembled vaccines optimizes CD4+ helper T cell and antibody outputs. Adv Healthc Mater. 2014; 3(11): 1898-908.

Reches et al., Biological and chemical decoration of peptide nanostructures via biotin-avidin interactions. J Nanosci Nanotechno. 2007;7(7):2239-45.

Restuccia et al., Self-assembled glycopeptide nanofibers as modulators of galectin-1 bioactivity. Cell Mol Bioeng. 2015; 8(3): 471-87.

Rudra et al., A self-assembling peptide acting as an immune adjuvant. Proc Natl Acad Sci U S A. 2010; 107(2): 622-7.

Rudra et al., Modulating adaptive immune responses to peptide self-assemblies. ACS Nano. 2012; 6(2): 1557-64.

Sangiambut et al., A robust route to enzymatically functional, hierarchically self-assembled peptide frameworks. Advanced Materials. 2013; 25(19): 2661-5.

Sawada et al., Affinity-based screening of peptides recognizing assembly states of self-assembling peptide nanomaterials. Journal of the American Chemical Society. 2009; 131(40): 14434-41.

Sawada et al., Dense surface functionalization using peptides that recognize differences in organized structures of self-assembling nanomaterials. Mol Biosyst. 2012; 8(4): 1264-74.

Seroski et al., Co-assembly tags based on charge complementarity (CATCH) for installing functional protein ligands into supramolecular biomaterials.Cellular and Molecular Bioengineering 9:3, Sep. 2016, 335-350.

Stendahl et al., Growth factor delivery from self-assembling nanofibers to facilitate islet transplantation. Transplantation. 2008; 86(3): 478-81.

Tian et al., Fibrillized peptide microgels for cell encapsulation and 3D cell culture. Soft Matter. 2011; 7(13): 6005-11.

Wu et al., Active protein aggregates induced by terminally attached self-assembling peptide ELK16 in *Escherichia coli*. Microb Cell Fact. 2011; 10:9, 1-8.

Ma et al., Protein Secondary Structure Prediction Based on Data Partition and Semi-Random Subspace Method. Sci Rep. Jun. 29, 2018;8(1):9856. doi: 10.1038/s41598-018-28084-8.

Positive Peptide

Negative Peptide

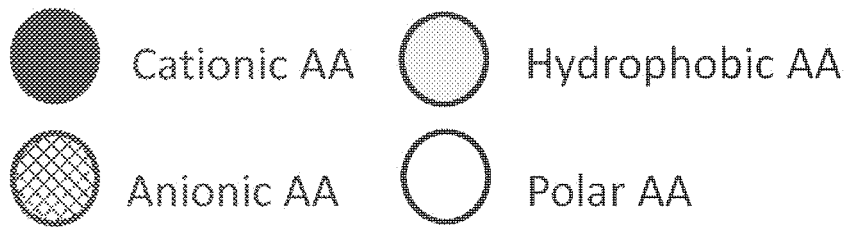
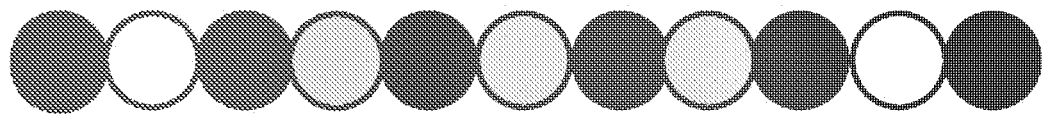
Positive Peptide
FIG. 2C
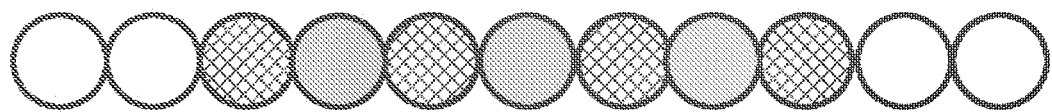
Negative Peptide
FIG. 2D
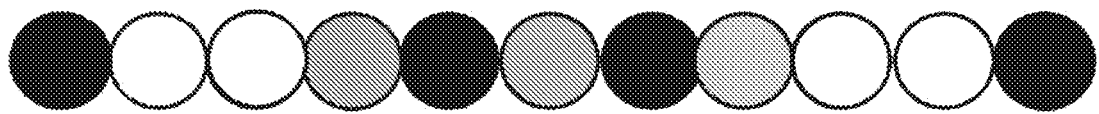
Positive Peptide
FIG. 2E

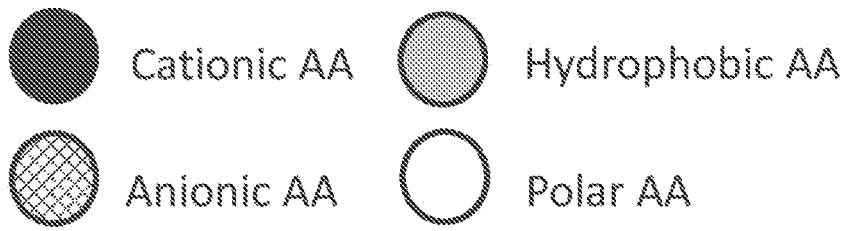
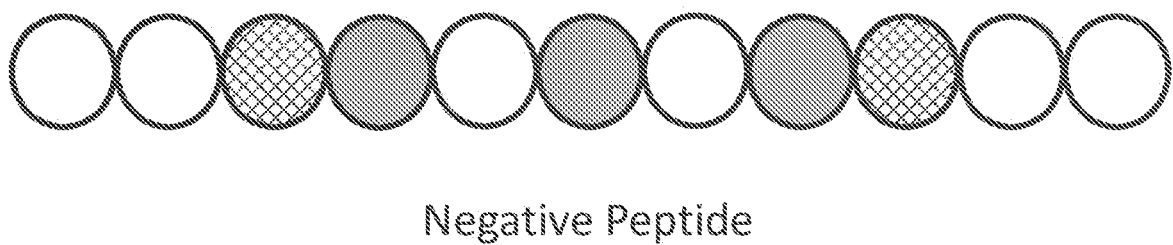
Negative Peptide
FIG. 2F
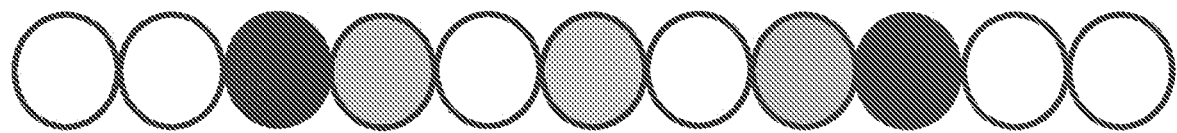
Positive Peptide
FIG. 2G

CATCH(+) – Ac-QQKFKFKFKQQ-Am   SEQ ID NO: 1
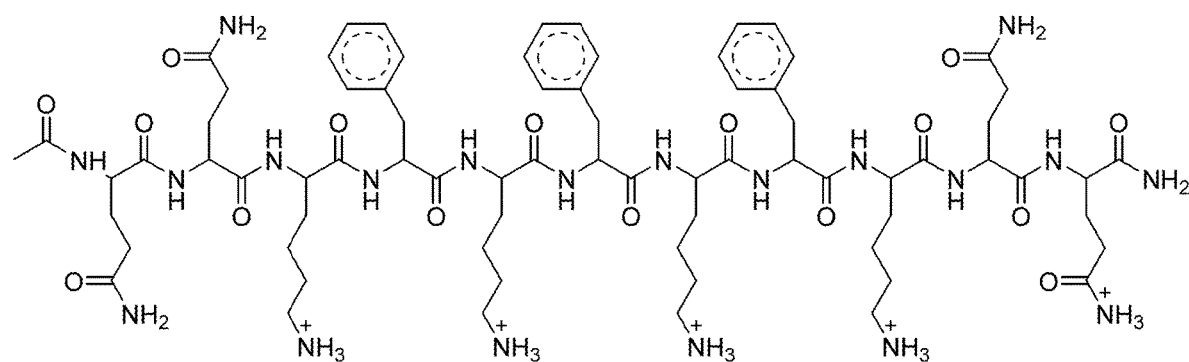
CATCH(-) – Ac-EQEFEFEFEQE-Am   SEQ ID NO: 2
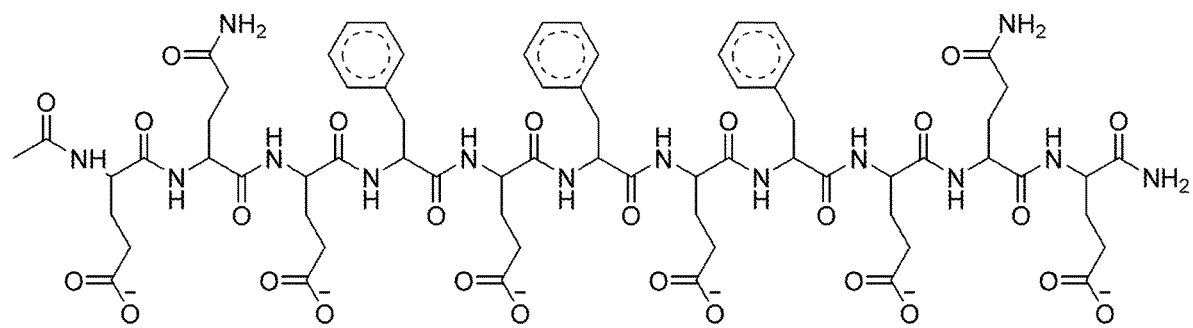
FIG. 6

CATCH(+)
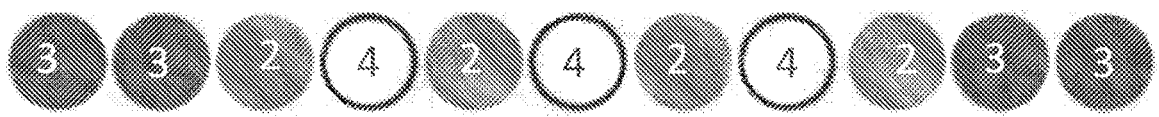
① = anionic     ③ = polar
② = cationic    ④ = hydrophobic
CATCH(-)
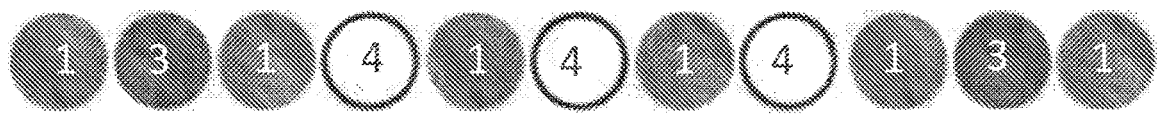
FIG. 7A

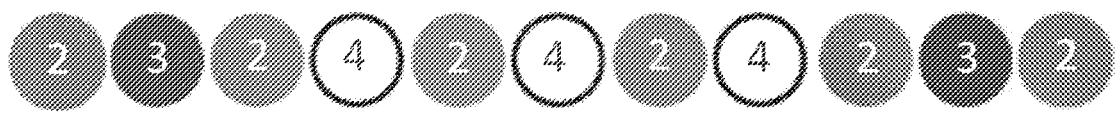
 = anionic    = polar
 = cationic    = hydrophobic
FIG. 7B

```
T7-term
TGGGGTCGTTCCCTCTAGAAATATTTTGTTTAACTTTAAGAAGGAGATATACCATGGCCGAACAGGAATTTGAATTG
AATTTGAACAGGAAGGATCCGGCGGCGGCAGGGGGGGGCAGCGGCGGCGGCGGCAGCGGCGGCGGCGAATTCTCC
AAAGGAGAAGAGCTGTTCACTGGAGTGGTACCAATACTTGTGGAGTTGGACGGAGATGTGAACGGACACAAATTTTC
AGTCCGCGGGAGGGGAAGGGGATGCTACTATTGGCAAGCTGACGCTCAAATTCATCTGTACCACCGGAAAACTCC
CTGTACCCTGGCCACACTGGTGACAACTCTGACTTACGGCGTGCAATGTTTTAGCCGATACCCAGACCACATGAAG
AGGCACGGACTTTTTCAAAAGCGCAATGCCTGAAGGATACGTACAGGAAAGGACCATTTCTTTTAAAGACGACGGGAA
GTACAAAACCCGGGCAGTGGTGAAGTTTGAGGGCGATACCCTCGTCAATAGGATCGAATTGAAGGGAACTGACTTCA
AAGAAGATGGCAACATCCTGGGTCACAAGCTTGAGTATAACTTTAACTCCCACAACGTGTATATTACAGCCGACAAA
CAGAAGAATGGAATTAAGGCTAACTTCACTGTCAGACACAATGTCGAAGATGGCTCCGTGCAGCTCGCCGATCACTA
TCAACAGAATACTCCTATCGGGGACGGCCCAGTCCTGCTGCCCGACAACCACTACCTGAGTACCCAGACTGTTCTGA
GCAAAGATCCGAACGAGAAGCGCGACCACATGGTGCTGCATGAGTATGTGAACGCTGCGGGAATTACCCTCGGCATG
GACGAGCTGTACAAGCTGGAGCACCACCACCACCACCACTGAGATCCGGCTGCTAACAAAGCCCGAAAGGAAGCTGA
GTTGGCTGCTGCCACCGCTGAGCAATAACTAGCAATAACCCCTTTGGGCCTCTAAACGGGTCTTGAGGGGTTTT
TTGCTGAAAAGAGGAACTATTATGGGATTGGCCGAATGGGACGCGCCCTGTAGCGCGCATAGGGCGGCGGGGTGG
TGGTACGGCAGCGTGACGGCTAACTGGCAGCGGCCTAGNNNCGGCTTCCTTTCGNTCNTCCATTCCAATCCTGCC
AAGCTCNNCCCGGGGATTTCCCACCG 5'3' Frame 2
G V V P S R Y F C L T L R R R Y T                                        Stop  D P A A R K A R K
E A E L A A A T A G A I T S R N P F G P L N R V L E G F A E R R Y P D W
P N G T R F V A P I A R R G W W Y A Q R D G Y T G S G L X X A S F X K S I P I
L P S X X R G F P T
```

FIG. 12

```
T7-term
    1 GCTTCCTTTC GGGCTTTGTT AGCAGCCGGA TCTCAGTGGT GGTGGTGGTG
   51 GTGCTCGAGC TTGTACAGCT CGTCCATGCC GAGGGTAATT CCCGCAGCGT
  101 TGACATACTC ATGCAGCACC ATGTGGTCGC GCTTCTCGTT CGGATCTTTG
  151 CTCAGAACAG TCTGGGTACT CAGGTAGTGG TTGTCGGGCA GCAGGACTGG
  201 GCCGTCCCCG ATAGGAGTAT TCTGTTGATA GTGATCGGCG AGCTGCACGG
  251 AGCCATCTTC GACATTGTGT CTGACAGTGA AGTTAGCCTT AATTCCATTC
  301 TTCTGTTTGT CGGCTGTAAT ATACACGTTG TGGGAGTTAA AGTTATACTC
  351 AAGCTTGTGA CCCAGGATGT TGCCATCTTC TTTGAAGTCA GTTCCCTTCA
  401 ATTCGATCCT ATTGACGAGG GTATCGCCCT CAAACTTCAC CACTGCCCGG
  451 GTTTTGTACT TCCCGTCGTC TTTAAAAGAA ATGGTCCTTT CCTGTACGTA
  501 TCCTTCAGGC ATTGCGCTTT TGAAAAAGTC GTGCCTCTTC ATGTGGTCTG
  551 GGTATCGGCT AAAACATTGC ACGCCGTAAG TCAGAGTTGT CACCAGTGTG
  601 GGCCAGGGTA CAGGGAGTTT TCCGGTGGTA CAGATGAATT TGAGCGTCAG
  651 CTTGCCAATA GTAGCATCCC CTTCCCCCTC CCCGCGGACT GAAAATTTGT
  701 GTCCGTTCAC ATCTCCGTCC AACTCCACAA GTATTGGTAC CACTCCAGTG
  751 AACAGCTCTT CTCCTTTGGA GAATTCGCCG CTGCCGCCGC TGCCGCCGCC
  801 GCCGCTGCCG CCGCTGCCGC CGCCGGATCC TTCCTGTTCG GGTTCGGGTT
  851 CGGGTTCCTG TTCGGCCATG GTATATCTCC TTCTTAAAGT TAAACAAAAA
  901 TTATTTCTAG AGGGGAATTG TTATCCGCTC ACAATTCCCC TATAGTGAGT
  951 CGTATTAATT T 3'5' Frame 3
I N T T H Y R G I V S G Stop Q F P S R N N F C L T L R R R Y T Stop D P A A N K A R K E
```

FIG. 13

CATCH(+) + CATCH(-)

CATCH(-)

CATCH(+)

*Tri-assembly*
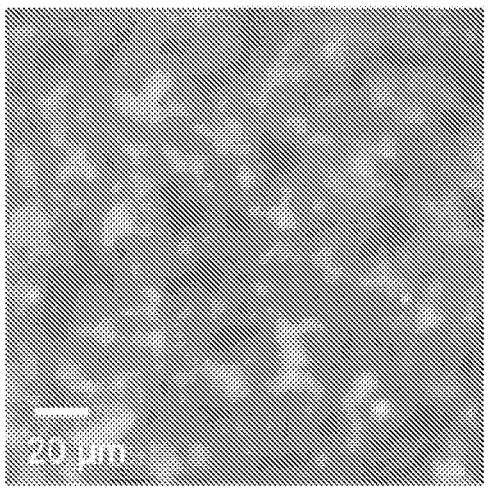 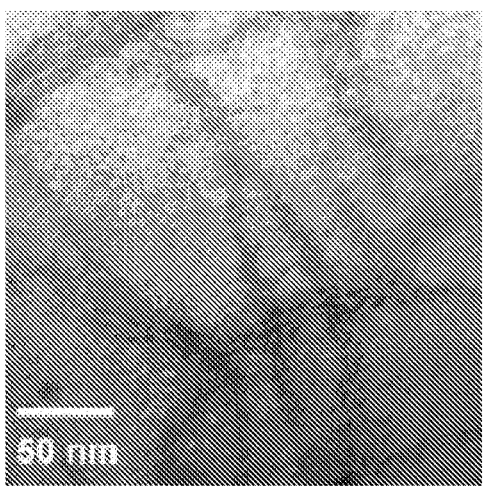
FIG. 27A    FIG. 27B
*Tri-assembly controls*
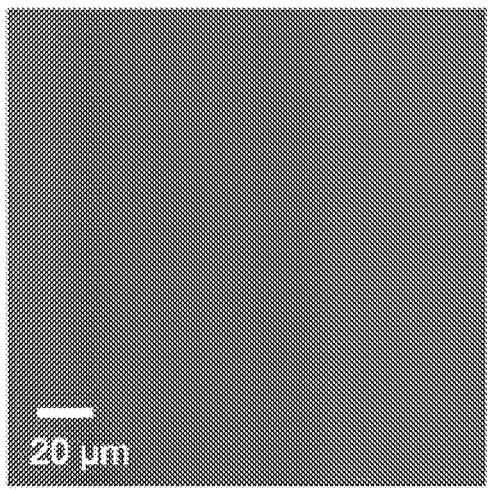 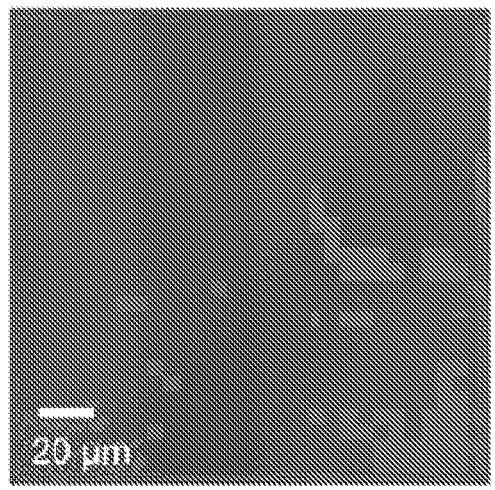
FIG. 28A    FIG. 28B

*Di-assembly*
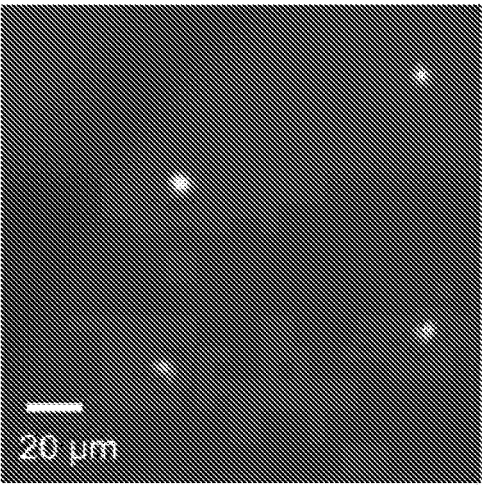
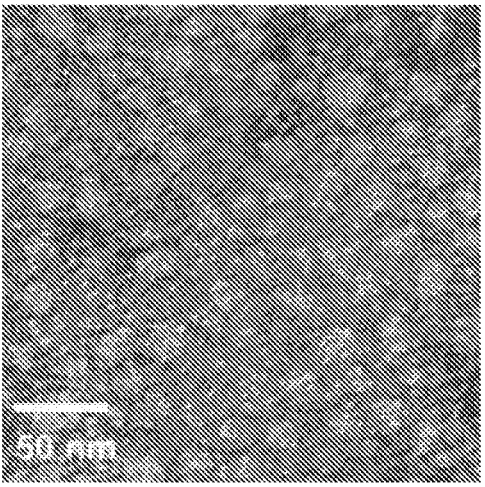
FIG. 29A　　　　　　　FIG. 29B
*Di-assembly controls*
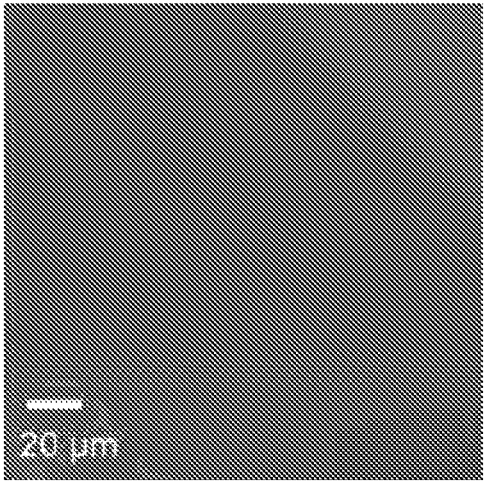
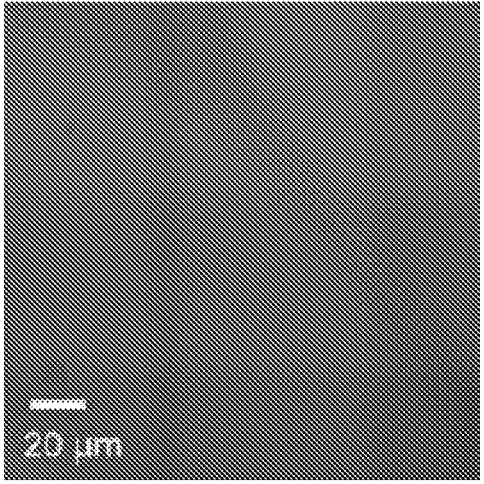
FIG. 30A　　　　　　　FIG. 30B CATCH(+) or CATCH(-)

CATCH(+) and CATCH(-)

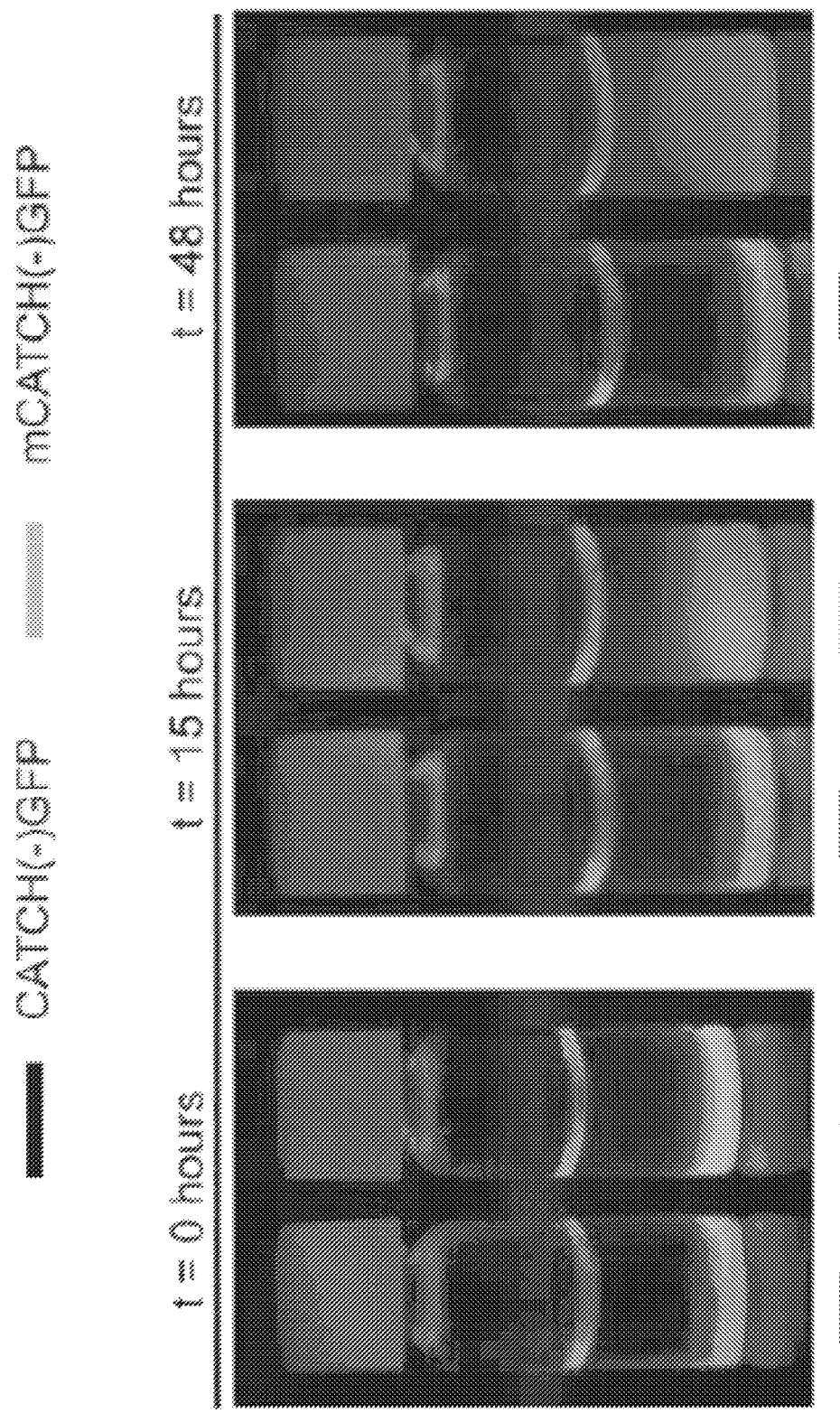

CATCH(4/4)

CATCH(4/6)

CATCH(6/4)

CATCH(6/6)

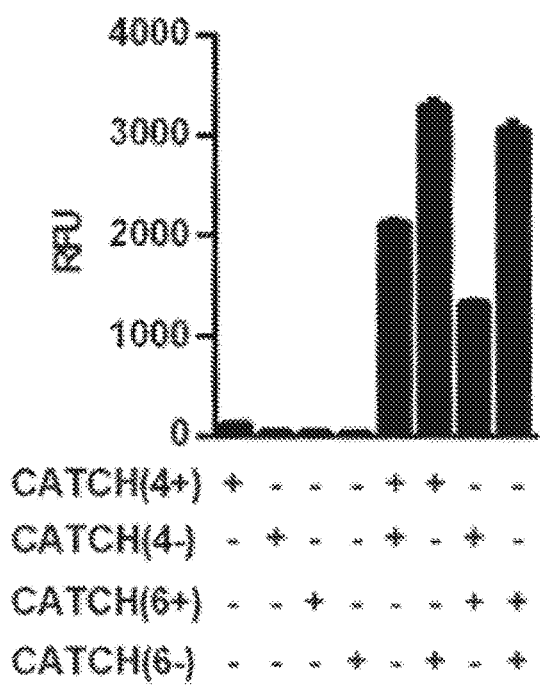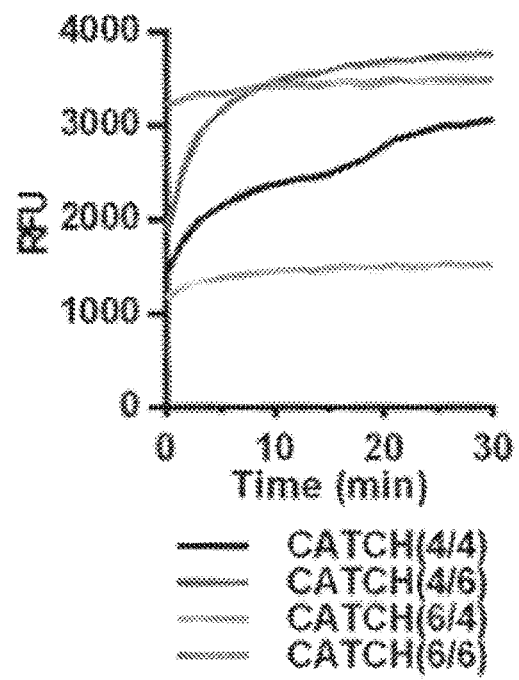
FIG. 40A
FIG. 40B

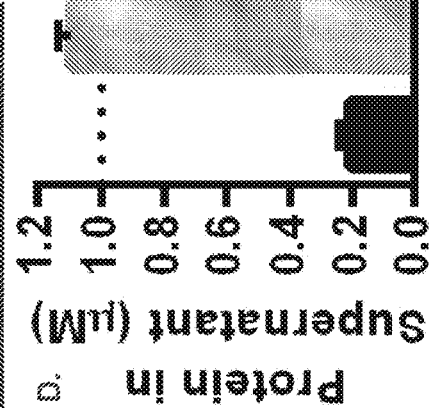
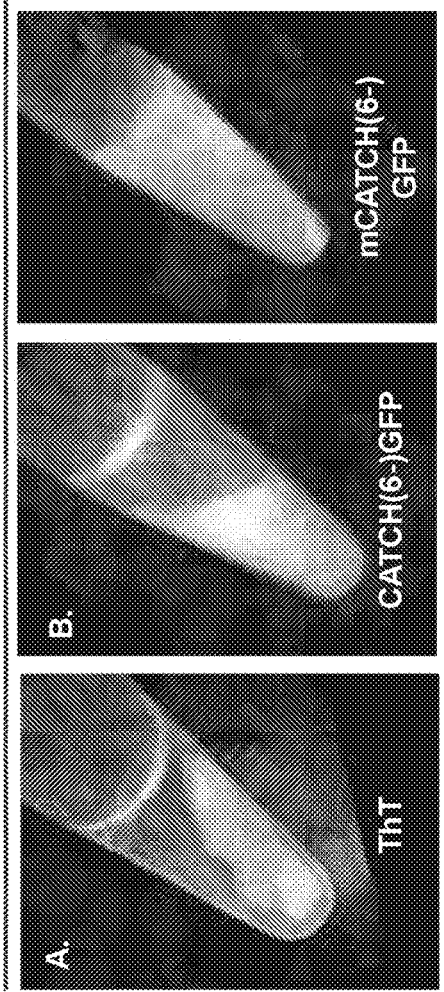
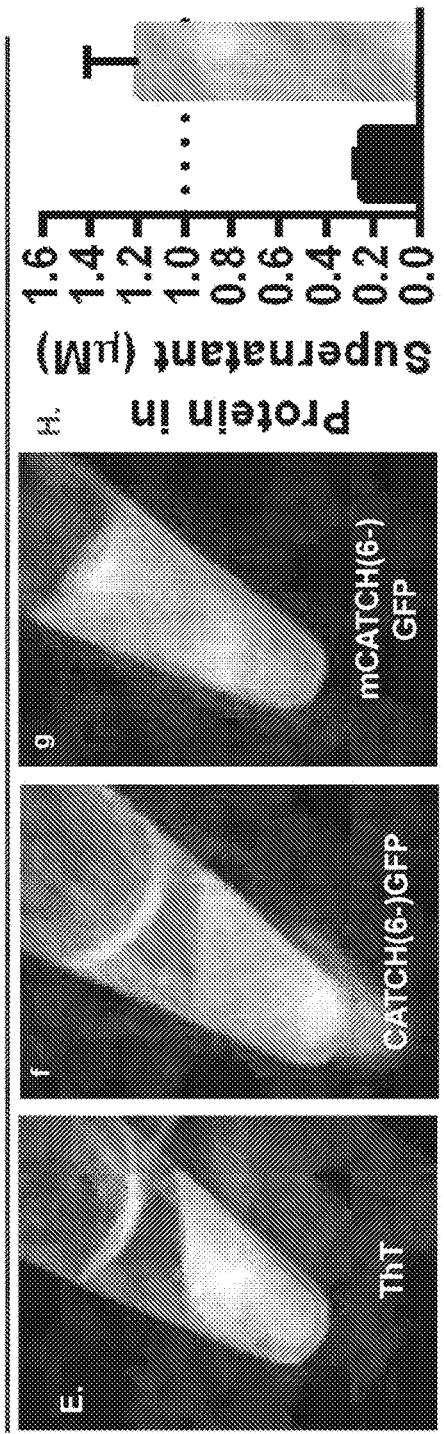
FIGS. 42A-42H

CATCH(4/4)

CATCH(4/6)

CATCH(6/4)

CATCH(6/6)

0.1 µm

ATG GAAAATTATATTTCCAGACGAACAGGAATTTGAATTTG
AATTTGAACAGGAAGAAATTTATATTTCCAGACGAACAGGAATTTGAATTTGAACA
GGAAGAAATTTATATTTCCAGACGAACAGGAATTTGAATTTGAACAGGAAGAAAT
TTATATTTCCAGACGAACAGGAATTTGAATTTGAACAGGAAGAAATTTATATTTC
AGACGAACAGGAATTTGAATTTGAACAGGAAGAAATTTATATTTCAGACGAACA
GGAATTTGAATTTGAACAGGAAGAAATTTATATTTCCAGACGAACAGGAATTTGAA
TTTGAATTTGAACAGGAAGAAATTTATATTTCAGACGAACAGGAATTTGAATTTG
AACAGGAAGAAATTTATATTTCCAGACGAACAGGAATTTGAATTTGAACAGGAACA
AAATTATATTTCCAGACGAACAGGAAGAAATTTAT
TCCAGTGA

FIG. 50A

| Feature | DNA Sequence | Protein Sequence |
|---|---|---|
| His6 | CACCACCACCAC CACCAC | HHHHHH |
| TEVc | GAAAATTTATAT TTCCAGAGC | ENLYFQS |
| CATCH(6-) | GAACAGGAATTT GAATTTGAATTT GAACAGGAA | EQEFEFEFEQE |

FIG. 50C

ATGCACCACCACCACCACCACCACC
ACCACCACAACACGCCAGAACACAT
CACAGCCGTGGTGCAGCGTTATGTT
GCCGCCCTGAACGCCGGCGATTTAG
ATGGCATCGTTGCTTTGTTCGCCGA
CGACGCCACGGTGGAGGACCCTGTT
GGGAGCGAACCACGCTCTGGAACAG
CAGCGATACGTGAATTTTACGCTAA
TAGTCTGAAGCTGCCTCTTGCCGTA
GAACTTACTCAGGAGGTACGCGCGG
TCGCCAATGAAGCGGCTTTTGCTTT
CACGGTTTCGTTTGAATACCAAGGT
CGTAAGACTGTCGTAGCCCCTATAG
ACCACTTCAGATTCAATGGGGCGGG
CAAGGTGGTGAGTATCCGGGCATTG
TTCGGAGAGAAGAACATTCACGCTG
GCGCGCATCGAACAGGATTTGAAT
TTGAATTTGAACAGGAATGA

FIG. 53A

M H H H H H H H
H N T P E H I T
A V V Q R Y V A A
L N A G D L D G I
V A L F A D D A T
V E D P V G S E P
R S G T A A I R E
F Y A N S L K L P
L A V E L T Q E V
R A V A N E A A F
A F T V S F E Y Q
G R K T V V A P I
D H F R F N G A G
K V V S S R A L F
G E K N I H A G A
E E Q E F E F E F
E Q E Stop

FIG. 53B

| Feature | DNA Sequence | Protein Sequence |
|---|---|---|
| His10 | CACCACCACCACCACCACCA CCACCACCAC | HHHHHH HHHH |
| TEVc | AACACGCCAGAACACATCAC<br>AGCCGTGGTGCAGCGTTATG<br>TTGCCGCCCTGAACGCCGGC<br>GATTTAGATGGCATCGTTGC<br>TTTGTTCGCCGACGACGCCA<br>CGGTGGAGGACCCTGTTGGG<br>AGCGAACCACGCTCTGGAAC<br>AGCAGCGATACGTGAATTTT<br>ACGCTAATAGTCTGAAGCTG<br>CCTCTTGCCGTAGAACTTAC<br>TCAGGAGGTACGCGCGGTCG<br>CCAATGAAGCGGCTTTTGCT<br>TTCACGGTTTCGTTTGAATA<br>CCAAGGTCGTAACACTGTCG<br>TAGCCCCTATAGACCACTTC<br>AGATTCAATGGGGCGGGCAA<br>GGTGGTGAGTATCCGGGCAT<br>TGTTCGGAGAGAAGAACATT<br>CACGCTGGCGCGC | N T P E H I T<br>A V V Q R Y V<br>A A L N A G D<br>L D G I V A L<br>F A D D A T V<br>E D P V G S E<br>P R S G T A A<br>I R E F Y A N<br>S L K L P L A<br>V E L T Q E V<br>R A V A N E A<br>A F A F T V S<br>F E Y Q G R K<br>T V V A P I D<br>H F R F N G A<br>G K V V S S R<br>A L F G E K N<br>I H A G A |
| Methionine | ATG | M |
| CATCH(6-) | GAACAGGAATTTGAATTT GAATTTGAACAGGAA | E Q E F E F E F E Q E |

FIG. 53C

SEQUENCE LISTING

<160> NUMBER OF SEQ ID NOS: 51

<210> SEQ ID NO 1
<211> LENGTH: 11
<212> TYPE: PRT
<213> ORGANISM: Artificial Sequence
<220> FEATURE:
<223> OTHER INFORMATION: CATCH (4+)

<400> SEQUENCE: 1

Gln Gln Lys Phe Lys Phe Lys Phe Lys Gln Gln
1               5                   10

<210> SEQ ID NO 2
<211> LENGTH: 11
<212> TYPE: PRT
<213> ORGANISM: Artificial Sequence
<220> FEATURE:
<223> OTHER INFORMATION: CATCH (6-)

<400> SEQUENCE: 2

Glu Gln Glu Phe Glu Phe Glu Phe Glu Gln Glu
1               5                   10

<210> SEQ ID NO 3
<211> LENGTH: 11
<212> TYPE: PRT
<213> ORGANISM: Artificial Sequence
<220> FEATURE:
<223> OTHER INFORMATION: CATCH (6+)

<400> SEQUENCE: 3

Lys Gln Lys Phe Lys Phe Lys Phe Lys Gln Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: also referred to herein as CATCH (4-)

<400> SEQUENCE: 4

Gln Gln Glu Phe Glu Phe Glu Phe Glu Gln Gln
1               5                   10

<210> SEQ ID NO 5
<211> LENGTH: 11
<212> TYPE: PRT
<213> ORGANISM: Artificial Sequence
<220> FEATURE:
<223> OTHER INFORMATION: A CATCH peptide

<400> SEQUENCE: 5

Lys Gln Gln Phe Lys Phe Lys Phe Lys Gln Gln
1               5                   10

<210> SEQ ID NO 6
<211> LENGTH: 11
<212> TYPE: PRT
<213> ORGANISM: Artificial Sequence
<220> FEATURE:
<223> OTHER INFORMATION: also referred to herein as CATCH (2+)

<400> SEQUENCE: 6

Gln Gln Lys Phe Gln Phe Gln Phe Lys Gln Gln
1               5                   10

<210> SEQ ID NO 7
<211> LENGTH: 11
<212> TYPE: PRT
<213> ORGANISM: Artificial Sequence
<220> FEATURE:
<223> OTHER INFORMATION: also referred to herein as CATCH (2-)

<400> SEQUENCE: 7

Gln Gln Glu Phe Gln Phe Gln Phe Glu Gln Gln
1               5                   10

<210> SEQ ID NO 8
<211> LENGTH: 11
<212> TYPE: PRT
<213> ORGANISM: Artificial Sequence
<220> FEATURE:
<223> OTHER INFORMATION: also referred to herein as CATCH (*4+)

<400> SEQUENCE: 8

Lys Gln Gln Phe Lys Phe Lys Phe Gln Gln Lys
1               5                   10

<210> SEQ ID NO 9
<211> LENGTH: 18
<212> TYPE: PRT
<213> ORGANISM: Artificial Sequence
<220> FEATURE:
<223> OTHER INFORMATION: CATHC Pepetide with Protease clevage site

<400> SEQUENCE: 9

Ser Gln Gln Lys Phe Lys Phe Lys Phe Lys Gln Gln Glu Asn Leu Tyr
1               5                   10                  15

Glu Gln

<210> SEQ ID NO 10
<211> LENGTH: 19
<212> TYPE: PRT
<213> ORGANISM: Artificial Sequence
<220> FEATURE:
<223> OTHER INFORMATION: A CATCH peptide with a protease clevage site.

<400> SEQUENCE: 10

Ser Gln Gln Lys Phe Lys Phe Lys Phe Lys Gln Gln Trp Glu Asn Leu
1               5                   10                  15

Tyr Phe Gln

<210> SEQ ID NO 11
<211> LENGTH: 19
<212> TYPE: PRT
<213> ORGANISM: Artificial Sequence
<220> FEATURE:
<223> OTHER INFORMATION: A CATCH Peptide with a protease clevage site.

<400> SEQUENCE: 11

Ser Glu Gln Glu Phe Glu Phe Glu Phe Glu Gln Glu Trp Glu Asn Leu
1               5                   10                  15

Tyr Phe Gln

<210> SEQ ID NO 12
<211> LENGTH: 5
<212> TYPE: PRT
<213> ORGANISM: Artificial Sequence
<220> FEATURE:
<223> OTHER INFORMATION: Thrombin cleavage sequence

```
<400> SEQUENCE: 12

Leu Val Pro Arg Gly
1               5

<210> SEQ ID NO 13
<211> LENGTH: 4
<212> TYPE: PRT
<213> ORGANISM: Artificial Sequence
<220> FEATURE:
<223> OTHER INFORMATION: C-terminal residues after cleavage with
      Thrombin

<400> SEQUENCE: 13

Leu Val Pro Arg
1

<210> SEQ ID NO 14
<211> LENGTH: 8
<212> TYPE: PRT
<213> ORGANISM: Artificial Sequence
<220> FEATURE:
<223> OTHER INFORMATION: Human Rhinovirus 3C Protease cleavage sequence

<400> SEQUENCE: 14

Leu Glu Val Leu Phe Gln Gly Pro
1               5

<210> SEQ ID NO 15
<211> LENGTH: 6
<212> TYPE: PRT
<213> ORGANISM: Artificial Sequence
<220> FEATURE:
<223> OTHER INFORMATION: C-terminal residues after cleavage with Human
      Rhinovirus 3C Protease

<400> SEQUENCE: 15

Leu Glu Val Leu Phe Gln
1               5

<210> SEQ ID NO 16
<211> LENGTH: 5
<212> TYPE: PRT
<213> ORGANISM: Artificial Sequence
<220> FEATURE:
<223> OTHER INFORMATION: Factor Xa cleavage sequence
<220> FEATURE:
<221> NAME/KEY: misc_feature
<222> LOCATION: (5)..(5)
<223> OTHER INFORMATION: Xaa can be any naturally occurring amino acid

<400> SEQUENCE: 16

Ile Glu Gly Arg Xaa
1               5

<210> SEQ ID NO 17
<211> LENGTH: 4
<212> TYPE: PRT
<213> ORGANISM: Artificial Sequence
<220> FEATURE:
<223> OTHER INFORMATION: C-terminal residues after cleavage with Factor
      Xa

<400> SEQUENCE: 17

Ile Glu Gly Arg
1
```

```
<210> SEQ ID NO 18
<211> LENGTH: 5
<212> TYPE: PRT
<213> ORGANISM: Artificial Sequence
<220> FEATURE:
<223> OTHER INFORMATION: Enterokinase cleavage sequence
<220> FEATURE:
<221> NAME/KEY: misc_feature
<222> LOCATION: (5)..(5)
<223> OTHER INFORMATION: Xaa can be any naturally occurring amino acid

<400> SEQUENCE: 18

Asp Asp Asp Lys Xaa
1               5

<210> SEQ ID NO 19
<211> LENGTH: 4
<212> TYPE: PRT
<213> ORGANISM: Artificial Sequence
<220> FEATURE:
<223> OTHER INFORMATION: C-terminal residues after cleavage with
      Enterokinase

<400> SEQUENCE: 19

Asp Asp Asp Lys
1

<210> SEQ ID NO 20
<211> LENGTH: 6
<212> TYPE: PRT
<213> ORGANISM: Artificial Sequence
<220> FEATURE:
<223> OTHER INFORMATION: TEV cleavage sequence

<400> SEQUENCE: 20

Glu Asn Lys Phe Gln Ser
1               5

<210> SEQ ID NO 21
<211> LENGTH: 5
<212> TYPE: PRT
<213> ORGANISM: Artificial Sequence
<220> FEATURE:
<223> OTHER INFORMATION: C-terminal residues after cleavage with TEV

<400> SEQUENCE: 21

Glu Asn Leu Phe Gln
1               5

<210> SEQ ID NO 22
<211> LENGTH: 11
<212> TYPE: PRT
<213> ORGANISM: Artificial Sequence
<220> FEATURE:
<223> OTHER INFORMATION: a mCATCH(-) (a mutant CATCH(-) peptide)

<400> SEQUENCE: 22

Glu Gln Glu Pro Glu Pro Glu Pro Glu Gln Glu
1               5                   10

<210> SEQ ID NO 23
<211> LENGTH: 11
<212> TYPE: PRT
<213> ORGANISM: Artificial Sequence
<220> FEATURE:
<223> OTHER INFORMATION: a mCATCH(+) (a mutant CATCH(+) peptide)

<400> SEQUENCE: 23
```

Gln Gln Lys Pro Lys Pro Lys Pro Lys Gln Gln
1               5                   10

<210> SEQ ID NO 24
<211> LENGTH: 1183
<212> TYPE: DNA
<213> ORGANISM: Artificial Sequence
<220> FEATURE:
<223> OTHER INFORMATION: T7-Terminal sequence of CATCH(-)GFP inserted in
      pET21d as determined by Sanger sequencing
<220> FEATURE:
<221> NAME/KEY: misc_feature
<222> LOCATION: (1121)..(1123)
<223> OTHER INFORMATION: n is a, c, g, t or u
<220> FEATURE:
<221> NAME/KEY: misc_feature
<222> LOCATION: (1137)..(1137)
<223> OTHER INFORMATION: n is a, c, g, t or u
<220> FEATURE:
<221> NAME/KEY: misc_feature
<222> LOCATION: (1140)..(1140)
<223> OTHER INFORMATION: n is a, c, g, t or u
<220> FEATURE:
<221> NAME/KEY: misc_feature
<222> LOCATION: (1164)..(1165)
<223> OTHER INFORMATION: n is a, c, g, t or u

<400> SEQUENCE: 24
tggggtcgtt ccctctagaa tattttgttt aactttaaga aggagatata ccatggccga      60
acaggaattt gaatttgaat tgaacagga aggatccggc ggcggcagcg gcggcagcgg     120
cggcggcggc agcggcggca gcggcgaatt ctccaaagga agagctgt tcactggagt      180
ggtaccaata cttgtggagt tggacggaga gtgtaacgga cacaaatttt cagtccgcgg    240
ggaggggaa ggggatgcta ctattggcaa gctgacgctc aaattcatct gtaccaccgg    300
aaaactccct gtaccctggc ccacactggt gacaacrctg acrracggcg tgcaatgttt    360
tagccgatac ccagaccaca tgaagaggca cgacttttc aaaagcgcaa tgcctgaagg     420
atacgtacag gaaggacca tttcttttaa agacgacggg aagtacaaaa cccgggcagt     480
ggtgaagttt gagggcgata ccctcgtcaa taggatcgaa ttgaagggaa ctgacttcaa    540
agaagatggc aacatcctgg gtcacaagct tgagtataac tttaactccc acaacgtgta    600
tattacagcc gacaaacaga agaatggaat taaggctaac ttcactgtca gacacaatgt    660
cgaagatggc tccgtgcagc tcgccgatca ctatcaacag aatactccta tcggggacgg    720
cccagtcctg ctgcccgaca accactacct gagtacccag actgttctga gcaaagatcc    780
gaacgagaag cgcgaccaca tggtgctgca tgagtatgtc aacgctgcgg aattaccct    840
cggcatggac gagctgtaca agctcgagca ccaccaccac caccactgag atccggctgc    900
taacaaagcc cgaaaggaag ctgagttggc tgctgccacc gctggagcaa taactagcaa    960
taaccccttt ggggcctcta accgggtc ttggagggt ttttgctga aaagaggaac       1020
tattatccgg attggccgaa tgggacgcgc cctgtagcgc gcatagcgcg gcggggtgg    1080
tggtacgcgc agcgtgacgg ctacactggc agcggcctag nnnccgcttc ctttcgntcn    1140
tccattccaa tcctgccaag ctcnnccccgg ggatttccca ccg                     1183

<210> SEQ ID NO 25
<211> LENGTH: 392
<212> TYPE: PRT
<213> ORGANISM: Artificial Sequence
<220> FEATURE:
<223> OTHER INFORMATION: Amino acid translation of T7-Terminal sequence
      of CATCH(-)GFP inserted in pET21d
<220> FEATURE:

```
<221> NAME/KEY: misc_feature
<222> LOCATION: (372)..(373)
<223> OTHER INFORMATION: Xaa can be any naturally occurring amino acid
<220> FEATURE:
<221> NAME/KEY: misc_feature
<222> LOCATION: (377)..(378)
<223> OTHER INFORMATION: Xaa can be any naturally occurring amino acid
<220> FEATURE:
<221> NAME/KEY: misc_feature
<222> LOCATION: (386)..(387)
<223> OTHER INFORMATION: Xaa can be any naturally occurring amino acid

<400> SEQUENCE: 25

Gly Val Val Pro Ser Arg Ile Phe Cys Leu Thr Leu Arg Arg Tyr
1               5                   10                  15

Thr Met Ala Glu Gln Glu Phe Glu Phe Glu Gln Glu Gly Ser
            20                  25                  30

Gly Gly Gly Ser Gly Gly Ser Gly Gly Gly Ser Gly Gly Ser Gly
            35                  40                  45

Glu Phe Ser Lys Gly Glu Glu Leu Phe Thr Gly Val Val Pro Ile Leu
50                  55                  60

Val Glu Leu Asp Gly Asp Val Asn Gly His Lys Phe Ser Val Arg Gly
65                  70                  75                  80

Glu Gly Glu Gly Asp Ala Thr Ile Gly Lys Leu Thr Leu Lys Phe Ile
                85                  90                  95

Cys Thr Thr Gly Lys Leu Pro Val Pro Trp Pro Thr Leu Val Thr Thr
            100                 105                 110

Leu Thr Tyr Gly Val Gln Cys Phe Ser Arg Tyr Pro Asp His Met Lys
            115                 120                 125

Arg His Asp Phe Phe Lys Ser Ala Met Pro Glu Gly Tyr Val Gln Glu
        130                 135                 140

Arg Thr Ile Ser Phe Lys Asp Asp Gly Lys Tyr Lys Thr Arg Ala Val
145                 150                 155                 160

Val Lys Phe Glu Gly Asp Thr Leu Val Asn Arg Ile Glu Leu Lys Gly
                165                 170                 175

Thr Asp Phe Lys Glu Asp Gly Asn Ile Leu Gly His Lys Leu Glu Tyr
            180                 185                 190

Asn Phe Asn Ser His Asn Val Tyr Ile Thr Ala Asp Lys Gln Lys Asn
        195                 200                 205

Gly Ile Lys Ala Asn Phe Thr Val Arg His Asn Val Glu Asp Gly Ser
210                 215                 220

Val Gln Leu Ala Asp His Tyr Gln Gln Asn Thr Pro Ile Gly Asp Gly
225                 230                 235                 240

Pro Val Leu Leu Pro Asp Asn His Tyr Leu Ser Thr Gln Thr Val Leu
                245                 250                 255

Ser Lys Asp Pro Asn Glu Lys Arg Asp His Met Val Leu His Glu Tyr
            260                 265                 270

Val Asn Ala Ala Gly Ile Thr Leu Gly Met Asp Glu Leu Tyr Lys Leu
        275                 280                 285

Glu His His His His His His Asp Pro Ala Ala Asn Lys Ala Arg Lys
290                 295                 300

Glu Ala Glu Leu Ala Ala Ala Thr Ala Gly Ala Ile Thr Ser Asn Asn
305                 310                 315                 320

Pro Phe Gly Pro Leu Asn Arg Val Leu Glu Gly Phe Phe Ala Glu Lys
                325                 330                 335

Arg Asn Tyr Tyr Pro Asp Trp Pro Asn Gly Thr Arg Pro Val Ala Arg
            340                 345                 350
```

Ile Ala Arg Arg Gly Trp Trp Tyr Ala Gln Arg Asp Gly Tyr Thr Gly
        355                 360                 365

Ser Gly Leu Xaa Xaa Ala Ser Phe Xaa Xaa Ser Ile Pro Ile Leu Pro
    370                 375                 380

Ser Xaa Xaa Arg Gly Phe Pro Thr
385                 390

<210> SEQ ID NO 26
<211> LENGTH: 954
<212> TYPE: DNA
<213> ORGANISM: Artificial Sequence
<220> FEATURE:
<223> OTHER INFORMATION: T7-terminal polynucleotide obtained via Sanger
      Sequencing of mCATCH(-)GFP insert in pET21d

<400> SEQUENCE: 26

```
gcttcctttc gggctttgtt agcagccgga tctcagtggt ggtggtggtg gtgctcgagc      60
ttgtacagct cgtccatgcc gagggtaatt cccgcagcgt tgacatactc atgcagcacc     120
atgtggtcgc gcttctcgtt cggatcttgc tcagaacagc tgggtactca ggtagtggtt     180
gtcgggcagc aggactgggc cgtccccgat aggagtatct gttgatagtg atcggcgagc     240
tgcacggagc catcttcgac attgtgtctg acagtgaagt tagccttaat tccattcttc     300
tgtttgtcgg ctgtaatata cacgttgtgg gagttaaagt tatactcaag cttgtgaccc     360
aggatgttgc catcttcttt gaagtcagtt cccttcaatt cgatcctatt gacgagggta     420
tcgccctcaa acttcaccac tgcccgggtt ttgtacttcc cgtcgtcttt aaaagaaatg     480
gtccttttcct gtacgtatcc tcaggcattg cgcttttgaa aaagtcgtgc ctcttcatgt     540
ggtctgggta tcggctaaaa cattgccgcc gtaagtcaga gttgtcacca gtgtgggcca     600
gggtacaggg agttttccgg tggtacagat gaatttgagc gtcagcttgc caatagtagc     660
atccccttcc cctccccgc ggactgaaat ttgtgtccgt tcacatctcc gtccaactcc     720
acaagtattg gtaccactcc agtgaacagc tcttctcctt tggagaattc gccgctgccg     780
ccgctgccgc cgccgccgct gccgccgctg ccgccgccgg atccttcctg ttcgggttcg     840
ggttcgggtt cctgttcggc catggtatat ctccttctta agttaaacaa aaattatttc     900
tagaggggaa ttgttatccg ctcacaattc ccctatagtg agtcgtatta attt           954
```

<210> SEQ ID NO 27
<211> LENGTH: 316
<212> TYPE: PRT
<213> ORGANISM: Artificial Sequence
<220> FEATURE:
<223> OTHER INFORMATION: Amino Acid translation of T7-terminal sequence
      of mCATCH(-)GFP insert in pET21d

<400> SEQUENCE: 27

Ile Asn Thr Thr His Tyr Arg Gly Ile Val Ser Gly Gln Phe Pro Ser
1               5                   10                  15

Arg Asn Asn Phe Cys Leu Thr Leu Arg Arg Arg Tyr Thr Met Ala Glu
            20                  25                  30

Gln Glu Pro Glu Pro Glu Pro Glu Gln Glu Gly Ser Gly Gly Gly Ser
        35                  40                  45

Gly Gly Ser Gly Gly Gly Ser Gly Gly Ser Gly Glu Phe Ser Lys
    50                  55                  60

Gly Glu Glu Leu Phe Thr Gly Val Val Pro Ile Leu Val Glu Leu Asp
65                  70                  75                  80

```
Gly Asp Val Asn Gly His Lys Phe Ser Val Arg Gly Glu Gly Glu Gly
             85                  90                  95

Asp Ala Thr Ile Gly Lys Leu Thr Leu Lys Phe Ile Cys Thr Thr Gly
            100                 105                 110

Lys Leu Pro Val Pro Trp Pro Thr Leu Val Thr Thr Leu Thr Tyr Gly
        115                 120                 125

Val Gln Cys Phe Ser Arg Tyr Pro Asp His Met Lys Arg His Asp Phe
    130                 135                 140

Phe Lys Ser Ala Met Pro Glu Gly Tyr Val Gln Glu Arg Thr Ile Ser
145                 150                 155                 160

Phe Lys Asp Asp Gly Lys Tyr Lys Thr Arg Ala Val Val Lys Phe Glu
                165                 170                 175

Gly Asp Thr Leu Val Asn Arg Ile Glu Leu Lys Gly Thr Asp Phe Lys
            180                 185                 190

Glu Asp Gly Asn Ile Leu Gly His Lys Leu Glu Tyr Asn Phe Asn Ser
        195                 200                 205

His Asn Val Tyr Ile Thr Ala Asp Lys Gln Lys Asn Gly Ile Lys Ala
    210                 215                 220

Asn Phe Thr Val Arg His Asn Val Glu Asp Gly Ser Gln Leu Ala Asp
225                 230                 235                 240

His Tyr Gln Gln Asn Thr Pro Ile Gly Asp Gly Pro Val Leu Leu Pro
                245                 250                 255

Asp Asn His Tyr Leu Ser Thr Gln Thr Val Leu Ser Lys Asp Pro Asn
            260                 265                 270

Glu Lys Arg Asp His Met Val Leu His Glu Tyr Val Asn Ala Ala Gly
        275                 280                 285

Ile Thr Leu Gly Met Asp Glu Leu Tyr Lys Leu Glu His His His His
    290                 295                 300

His His Asp Pro Ala Ala Asn Lys Ala Arg Lys Glu
305                 310                 315

<210> SEQ ID NO 28
<211> LENGTH: 585
<212> TYPE: DNA
<213> ORGANISM: Artificial Sequence
<220> FEATURE:
<223> OTHER INFORMATION: polynucleotide capable of encoding a CATCH(6-)
      polypeptide

<400> SEQUENCE: 28
atgcaccacc accaccacca ccacgaaaat ttatatttcc agagcgaaca ggaatttgaa      60
tttgaatttg aacaggaaga aaatttatat ttccagagcg aacaggaatt tgaatttgaa     120
tttgaacagg aagaaaattt atatttccag agcgaacagg aatttgaatt tgaatttgaa     180
caggaagaaa atttatattt ccagagcgaa caggaatttg aatttgaatt tgaacaggaa     240
gaaaatttat atttccagag cgaacaggaa tttgaatttg aatttgaaca ggaagaaaat     300
ttatatttcc agagcgaaca ggaatttgaa tttgaatttg aacaggaaga aaatttatat     360
ttccagagcg aacaggaatt tgaatttgaa tttgaacagg aagaaaattt atatttccag     420
agcgaacagg aatttgaatt tgaatttgaa caggaagaaa atttatattt ccagagcgaa     480
caggaatttg aatttgaatt tgaacaggaa gaaaatttat atttccagag cgaacaggaa     540
tttgaatttg aatttgaaca ggaagaaaat ttatatttcc agtga                     585

<210> SEQ ID NO 29
<211> LENGTH: 193
```

```
<212> TYPE: PRT
<213> ORGANISM: Artificial Sequence
<220> FEATURE:
<223> OTHER INFORMATION: A CATCH(6-) polypeptide

<400> SEQUENCE: 29

Met His His His His His His Glu Asn Leu Tyr Phe Gln Ser Glu Gln
1               5                   10                  15

Glu Phe Glu Phe Glu Phe Glu Gln Glu Glu Asn Leu Tyr Phe Gln Ser
            20                  25                  30

Glu Gln Glu Phe Glu Phe Glu Phe Glu Gln Glu Glu Asn Leu Tyr Phe
        35                  40                  45

Gln Ser Glu Gln Glu Phe Glu Phe Glu Phe Glu Gln Glu Glu Asn Leu
    50                  55                  60

Tyr Phe Gln Ser Glu Gln Glu Phe Glu Phe Glu Phe Glu Gln Glu Glu
65                  70                  75                  80

Asn Leu Tyr Phe Gln Ser Glu Gln Glu Phe Glu Phe Glu Phe Glu Gln
                85                  90                  95

Glu Glu Asn Leu Tyr Phe Gln Ser Glu Gln Glu Phe Glu Phe Glu Phe
            100                 105                 110

Glu Gln Glu Glu Asn Leu Tyr Phe Gln Ser Glu Gln Glu Phe Glu Phe
        115                 120                 125

Glu Phe Glu Gln Glu Glu Asn Leu Tyr Phe Gln Ser Glu Gln Glu Phe
    130                 135                 140

Glu Phe Glu Phe Glu Gln Glu Glu Asn Leu Tyr Phe Gln Ser Glu Gln
145                 150                 155                 160

Glu Phe Glu Phe Glu Phe Glu Gln Glu Glu Asn Leu Tyr Phe Gln Ser
                165                 170                 175

Glu Gln Glu Phe Glu Phe Glu Phe Glu Gln Glu Glu Asn Leu Tyr Phe
            180                 185                 190

Gln

<210> SEQ ID NO 30
<211> LENGTH: 18
<212> TYPE: DNA
<213> ORGANISM: Artificial Sequence
<220> FEATURE:
<223> OTHER INFORMATION: A His 6 encoding polypeptide

<400> SEQUENCE: 30
caccaccacc accaccac                                                  18

<210> SEQ ID NO 31
<211> LENGTH: 6
<212> TYPE: PRT
<213> ORGANISM: Artificial Sequence
<220> FEATURE:
<223> OTHER INFORMATION: His 6 polypeptide

<400> SEQUENCE: 31

His His His His His His
1               5

<210> SEQ ID NO 32
<211> LENGTH: 21
<212> TYPE: DNA
<213> ORGANISM: Artificial Sequence
<220> FEATURE:
<223> OTHER INFORMATION: a TEVc encoding polypeptide

<400> SEQUENCE: 32
```

```
gaaaatttat atttccagag c                                              21

<210> SEQ ID NO 33
<211> LENGTH: 7
<212> TYPE: PRT
<213> ORGANISM: Artificial Sequence
<220> FEATURE:
<223> OTHER INFORMATION: A TEVc polypeptide

<400> SEQUENCE: 33

Glu Asn Leu Tyr Phe Gln Ser
1               5

<210> SEQ ID NO 34
<211> LENGTH: 32
<212> TYPE: DNA
<213> ORGANISM: Artificial Sequence
<220> FEATURE:
<223> OTHER INFORMATION: a CATCH(6-) encoding polypeptide

<400> SEQUENCE: 34
gaacggaatt tgaatttgaa tttgaacagg aa                                  32

<210> SEQ ID NO 35
<211> LENGTH: 445
<212> TYPE: DNA
<213> ORGANISM: Artificial Sequence
<220> FEATURE:
<223> OTHER INFORMATION: A polynucleotide capable of encoding
      KSI-CATCH(6-) polypeptide

<400> SEQUENCE: 35
atgcaccacc accaccacca ccaccaccac cacaacacgc cagaacacat cacagccgtg     60
gtgcagcgtt atgttgccgc cctgaacgcc ggcgatttag atggcatcgt tgctttgttc    120
gccgacgacg ccacggtgga ggaccctgtt gggagcgaac cacgctctgg aacagcagcg    180
atacgtgaat tttacgctaa tagtctgaag ctgcctcttg ccgtagaact tactcaggag    240
gtacgcgcgg tcgccaatga agcggctttt gctttcacgg tttcgtttga ataccaaggt    300
cgtaagactg tcgtagcccc tatagaccac ttcagattca atggggcggg caaggtggtg    360
agtatccggg cattgttcgg agagaagaac attcacgctg cgcgcatgg aacaggaatt    420 tgaatttgaa tttgaacagg aatga                                         445

<210> SEQ ID NO 36
<211> LENGTH: 145
<212> TYPE: PRT
<213> ORGANISM: Artificial Sequence
<220> FEATURE:
<223> OTHER INFORMATION: A KSI-CATCH(6-) encoded polypeptide

<400> SEQUENCE: 36

Met His His His His His His His His His Asn Thr Pro Glu His
1               5                   10                  15

Ile Thr Ala Val Val Gln Arg Tyr Val Ala Ala Leu Asn Ala Gly Asp
            20                  25                  30

Leu Asp Gly Ile Ala Leu Phe Ala Asp Asp Ala Thr Glu Asp Pro Val
        35                  40                  45

Gly Ser Glu Pro Arg Ser Gly Thr Ala Ala Ile Arg Glu Phe Tyr Ala
    50                  55                  60

Asn Ser Leu Lys Leu Pro Leu Ala Val Glu Leu Thr Gln Glu Val Arg
65                  70                  75                  80
```

```
Ala Val Ala Asn Glu Ala Ala Phe Ala Phe Thr Val Ser Phe Glu Tyr
                85                  90                  95

Gln Gly Arg Lys Thr Val Val Ala Pro Ile Asp His Phe Arg Phe Asn
            100                 105                 110

Gly Ala Gly Lys Val Val Ser Ser Arg Ala Leu Phe Gly Glu Lys Asn
        115                 120                 125

Ile His Ala Gly Ala Met Glu Gln Glu Phe Glu Phe Glu Phe Glu Gln
    130                 135                 140

Glu
145

<210> SEQ ID NO 37
<211> LENGTH: 30
<212> TYPE: DNA
<213> ORGANISM: Artificial Sequence
<220> FEATURE:
<223> OTHER INFORMATION: His10 encoding polynucleotide

<400> SEQUENCE: 37
caccaccacc accaccacca ccaccaccac                                      30

<210> SEQ ID NO 38
<211> LENGTH: 10
<212> TYPE: PRT
<213> ORGANISM: Artificial Sequence
<220> FEATURE:
<223> OTHER INFORMATION: His10 polypeptide

<400> SEQUENCE: 38

His His His His His His His His His His
1               5                   10

<210> SEQ ID NO 39
<211> LENGTH: 374
<212> TYPE: DNA
<213> ORGANISM: Artificial Sequence
<220> FEATURE:
<223> OTHER INFORMATION: TEVc encoding polynucleotide

<400> SEQUENCE: 39
aacaacgcca gaaacacatca cagccgtggt gcagcgttat gttgccgccc tgaacgccgg      60
cgatttagat ggcatcgttg cttttgttcgc cgacgacgcc acggtggagg accctgttgg    120
gagcgaacca cgctctggaa cagcagcgat acgtgaattt tacgctaata gtctgaagct    180
gcctcttgcc gtagaactta ctcaggaggt acgcgcggtc gccaatgaag cggcttttgc    240
tttcacggtt tcgtttgaat accaaggtcg taagactgtc gtagccccta tagaccactt    300
cagattcaat ggggcgggca aggtggtgag tatccgggca ttgttcggag agaagaacat    360
tcacgctggc gcgc                                                      374

<210> SEQ ID NO 40
<211> LENGTH: 124
<212> TYPE: PRT
<213> ORGANISM: Artificial Sequence
<220> FEATURE:
<223> OTHER INFORMATION: TEVc polypeptide

<400> SEQUENCE: 40

Asn Thr Pro Glu His Ile Thr Ala Val Val Gln Arg Tyr Val Ala Ala
1               5                   10                  15

Leu Asn Ala Gly Asp Leu Asp Gly Ile Val Ala Leu Phe Ala Asp Asp
```

```
                  20                  25                  30
Ala Thr Val Glu Asp Pro Val Gly Ser Glu Pro Arg Ser Gly Thr Ala
             35                  40                  45
Ala Ile Arg Glu Phe Tyr Ala Asn Ser Leu Lys Leu Pro Leu Ala Val
         50                  55                  60
Glu Leu Thr Gln Glu Val Arg Ala Val Ala Asn Glu Ala Ala Phe Ala
 65                  70                  75                  80
Phe Thr Val Ser Phe Glu Tyr Gln Gly Arg Lys Thr Val Val Ala Pro
                 85                  90                  95
Ile Asp His Phe Arg Phe Asn Gly Ala Gly Lys Val Val Ser Ser Arg
            100                 105                 110
Ala Leu Phe Gly Glu Lys Asn Ile His Ala Gly Ala
        115                 120
```

<210> SEQ ID NO 41
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 41

```
Gln Gln Lys Phe Gln Phe Gln Phe Glu Gln Gln
 1               5                   10
```

<210> SEQ ID NO 42
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 42

```
Glu Asn Lys Phe Gln Ser
 1               5
```

<210> SEQ ID NO 43
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 43

```
Ser Glu Asn Leu Tyr Phe Gln
 1               5
```

<210> SEQ ID NO 44
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(4)
<223> OTHER INFORMATION: Xaa can be a positively charged amino acid or a
      hydrophobic amino acid
<220> FEATURE:
<221> NAME/KEY: misc_feature
<222> LOCATION: (1)..(4)
<223> OTHER INFORMATION: Xaa1 = A4, Xaa2 = A3, Xaa3 = A2, Xaa4 = A1

<400> SEQUENCE: 44

Xaa Xaa Xaa Xaa

```
<210> SEQ ID NO 45
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(4)
<223> OTHER INFORMATION: Xaa can be a negatively charged amino acid or a
      hydrophobic amino acid
<220> FEATURE:
<221> NAME/KEY: misc_feature
<222> LOCATION: (1)..(4)
<223> OTHER INFORMATION: Xaa1 = B4, Xaa2 = B3, Xaa3 = B2, Xaa4 = B1

<400> SEQUENCE: 45

Xaa Xaa Xaa Xaa
1

<210> SEQ ID NO 46
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(5)
<223> OTHER INFORMATION: Xaa can be a positively charged amino acid or a
      hydrophobic amino acid
<220> FEATURE:
<221> NAME/KEY: misc_feature
<222> LOCATION: (1)..(5)
<223> OTHER INFORMATION: Xaa1 = A5, Xaa2 = A4, Xaa3 = A3, Xaa4 = A2,
      Xaa5 = A1

<400> SEQUENCE: 46

Xaa Xaa Xaa Xaa Xaa
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(5)
<223> OTHER INFORMATION: Xaa can be a negatively charged amino acid or a
      hydrophobic amino acid
<220> FEATURE:
<221> NAME/KEY: misc_feature
<222> LOCATION: (1)..(5)
<223> OTHER INFORMATION: Xaa1 = B5, Xaa2 = B4, Xaa3 = B3, Xaa4 = B2,
      Xaa5 = B1

<400> SEQUENCE: 47

Xaa Xaa Xaa Xaa Xaa
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
```

<222> LOCATION: (1)..(7)
<223> OTHER INFORMATION: Xaa can be a positively charged amino acid or a
      hydrophobic amino acid
<220> FEATURE:
<221> NAME/KEY: misc_feature
<222> LOCATION: (1)..(7)
<223> OTHER INFORMATION: Xaa1 = A7, Xaa2 = A6, Xaa3 = A5, Xaa4 = A4,
      Xaa5 = A3, Xaa6 = A2, Xaa7 = A1

<400> SEQUENCE: 48

Xaa Xaa Xaa Xaa Xaa Xaa Xaa
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(7)
<223> OTHER INFORMATION: Xaa can be a negatively charged amino acid or a
      hydrophobic amino acid
<220> FEATURE:
<221> NAME/KEY: misc_feature
<222> LOCATION: (1)..(7)
<223> OTHER INFORMATION: Xaa1 = B7, Xaa2 = B6, Xaa3 = B5, Xaa4 = B4,
      Xaa5 = B3, Xaa6 = B2, Xaa7 = B1

<400> SEQUENCE: 49

Xaa Xaa Xaa Xaa Xaa Xaa Xaa
1               5

<210> SEQ ID NO 50
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be a polar or a cationic amino acid
<220> FEATURE:
<221> NAME/KEY: misc_feature
<222> LOCATION: (2)..(2)
<223> OTHER INFORMATION: Xaa can be a polar amino acid
<220> FEATURE:
<221> NAME/KEY: misc_feature
<222> LOCATION: (3)..(3)
<223> OTHER INFORMATION: Xaa can be a polar or a cationic amino acid
<220> FEATURE:
<221> NAME/KEY: misc_feature
<222> LOCATION: (4)..(4)
<223> OTHER INFORMATION: Xaa can be a hydrophobic amino acid
<220> FEATURE:
<221> NAME/KEY: misc_feature
<222> LOCATION: (5)..(5)
<223> OTHER INFORMATION: Xaa can be a polar or a cationic amino acid
<220> FEATURE:
<221> NAME/KEY: misc_feature
<222> LOCATION: (6)..(6)
<223> OTHER INFORMATION: Xaa can be a hydrophobic amino acid
<220> FEATURE:
<221> NAME/KEY: misc_feature
<222> LOCATION: (7)..(7)
<223> OTHER INFORMATION: Xaa can be a polar or a cationic amino acid
<220> FEATURE:
<221> NAME/KEY: misc_feature
<222> LOCATION: (8)..(8)
<223> OTHER INFORMATION: Xaa can be a hydrophobic amino acid
<220> FEATURE:
<221> NAME/KEY: misc_feature
<222> LOCATION: (9)..(9)

<223> OTHER INFORMATION: Xaa can be a polar or a cationic amino acid
<220> FEATURE:
<221> NAME/KEY: misc_feature
<222> LOCATION: (10)..(10)
<223> OTHER INFORMATION: Xaa can be a polar amino acid
<220> FEATURE:
<221> NAME/KEY: misc_feature
<222> LOCATION: (11)..(11)
<223> OTHER INFORMATION: Xaa can be a polar or a cationic amino acid
<220> FEATURE:
<221> NAME/KEY: misc_feature
<222> LOCATION: (1)..(11)
<223> OTHER INFORMATION: Xaa1 = A11, Xaa2 = A10, Xaa3 = A9, Xaa4 = A8,
    Xaa5 = A7, Xaa6 = A6, Xaa7 = A5, Xaa8 = A4, Xaa9 = A3, Xaa10 = A2,
    Xaa11 = A1

<400> SEQUENCE: 50

Xaa Xaa Xaa Xaa Xaa Xaa Xaa Xaa Xaa Xaa Xaa
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be a polar or a anionic amino acid
<220> FEATURE:
<221> NAME/KEY: misc_feature
<222> LOCATION: (2)..(2)
<223> OTHER INFORMATION: Xaa can be a polar amino acid
<220> FEATURE:
<221> NAME/KEY: misc_feature
<222> LOCATION: (3)..(3)
<223> OTHER INFORMATION: Xaa can be a polar or a anionic amino acid
<220> FEATURE:
<221> NAME/KEY: misc_feature
<222> LOCATION: (4)..(4)
<223> OTHER INFORMATION: Xaa can be a hydrophobic amino acid
<220> FEATURE:
<221> NAME/KEY: misc_feature
<222> LOCATION: (5)..(5)
<223> OTHER INFORMATION: Xaa can be a polar or a anionic amino acid
<220> FEATURE:
<221> NAME/KEY: misc_feature
<222> LOCATION: (6)..(6)
<223> OTHER INFORMATION: Xaa can be a hydrophobic amino acid
<220> FEATURE:
<221> NAME/KEY: misc_feature
<222> LOCATION: (7)..(7)
<223> OTHER INFORMATION: Xaa can be a polar or a anionic amino acid
<220> FEATURE:
<221> NAME/KEY: misc_feature
<222> LOCATION: (8)..(8)
<223> OTHER INFORMATION: Xaa can be a hydrophobic amino acid
<220> FEATURE:
<221> NAME/KEY: misc_feature
<222> LOCATION: (9)..(9)
<223> OTHER INFORMATION: Xaa can be a polar or a anionic amino acid
<220> FEATURE:
<221> NAME/KEY: misc_feature
<222> LOCATION: (10)..(10)
<223> OTHER INFORMATION: Xaa can be a polar amino acid
<220> FEATURE:
<221> NAME/KEY: misc_feature
<222> LOCATION: (11)..(11)
<223> OTHER INFORMATION: Xaa can be a polar or a anionic amino acid
<220> FEATURE:
<221> NAME/KEY: misc_feature
<222> LOCATION: (1)..(11)
<223> OTHER INFORMATION: Xaa1 = B11, Xaa2 = B10, Xaa3 = B9, Xaa4 = B8,
    Xaa5 = B7, Xaa6 = B6, Xaa7 = B5, Xaa8 = B4, Xaa9 = B3, Xaa10 = B2,
    Xaa11 = B1

```
<400> SEQUENCE: 51

Xaa Xaa Xaa Xaa Xaa Xaa Xaa Xaa Xaa Xaa Xaa
1               5                   10
```

CO-ASSEMBLY PEPTIDES, NANOSTRUCTURES, AND METHODS OF MAKING AND USING THE SAME

CROSS-REFERENCE TO RELATED APPLICATIONS

This application is a continuation of U.S. patent application Ser. No. 15/672,783, filed on Aug. 9, 2017, which claims the benefit of and priority to U.S. Provisional Patent Application No. 62/464,526, Feb. 28, 2017, entitled "CO-ASSEMBLY PEPTIDES, NANOSTRUCTURES, AND METHODS OF MAKING AND USING THE SAME," and also claims the benefit of and priority to U.S. Provisional Patent Application No. 62/372,427, filed on Aug. 9, 2016, entitled "CO-ASSEMBLY TAGS BASED ON CHARGE-COMPLEMENTARITY FOR INSTALLING FOLDED PROTEINS INTO SUPRAMOLECULAR BIOMATERIALS," the contents of each of the aforementioned applications is incorporated by reference herein in its entirety.

SEQUENCE LISTING

This application contains a sequence listing filed in electronic form as an ASCII.txt file entitled U119570152US03-SEQ-JOB, created on Dec. 16, 2020. The content of the sequence listing is incorporated herein in its entirety.

BACKGROUND

Self-assembly is the spontaneous organization of molecules into a precise supramolecular architecture without any external guidance. Throughout nature, biomolecule self-assembly gives rise to various functional biomaterials that can perform complex tasks, such as molecular sensing and recognition, chemical synthesis, motility, and compartmentalization, as well as multi-scale hierarchical organization. There is increasing interest in biomolecule self-assembly for bottom-up fabrication of biomaterials for various technological applications.

SUMMARY

Described herein are sets of charge complementary self-assembling peptides that can contain a positive peptide that can contain at least 3 amino acids ($A_1$-$A_3$, as set forth sequentially from C to N terminus), wherein $A_1$, $A_2$, and As can be each independently selected from a positively charged amino acid and a hydrophobic amino acid, and wherein at least one amino acid of $A_1$-$A_3$ can be a positively charged amino acid and at least one amino acid of $A_1$-$A_3$ can be a hydrophobic amino acid; and a negative peptide can include at least 3 amino acids ($B_1$-$B_3$), wherein $B_1$, $B_2$, and $B_3$ can each be independently selected from a negatively charged amino acid and a hydrophobic amino acid, and wherein at least one amino acid of $B_1$-$B_3$ can be a negatively charged amino acid and at least one amino acid of $B_1$-$B_3$ can be a hydrophobic amino acid, and wherein the positive and the negative peptide can be configured to self-assemble when mixed under a stimulating condition.

In some embodiments, the positive peptide can have at least 4 amino acids ($A_1$-$A_4$ (SEQ ID NO: 44), as set forth sequentially from C to N terminus), wherein $A_1$, $A_2$, $A_3$, and $A_4$, are each independently selected from a positively charged amino acid and a hydrophobic amino acid, and wherein at least one amino acid of $A_1$-$A_4$ (SEQ ID NO: 44) can be a positively charged amino acid and at least one amino acid of $A_1$-$A_4$ (SEQ ID NO: 44) can be a hydrophobic amino acid; and wherein the negative peptide comprises at least 4 amino acids ($B_1$-$B_4$) (SEQ ID NO: 45), wherein $B_1$, $B_2$, $B_3$, and $B_4$ can each be independently selected from a negatively charged amino acid and a hydrophobic amino acid, and wherein at least one amino acid of $B_1$-$B_4$ can be a negatively charged amino acid and at least one amino acid of $B_1$-$B_4$ (SEQ ID NO: 45) can be a hydrophobic amino acid, wherein the positive and the negative peptide can be configured to self-assemble when mixed under a stimulating condition.

In some embodiments, the positive peptide and the negative peptide each comprise an additional amino acid such that the positive peptide can include 5 amino acids ($A_1$-$A_5$ (SEQ ID NO: 46) as set forth sequentially from C to N terminus), wherein $A_1$, $A_2$, $A_3$, $A_4$, and As, can each be independently selected from a positively charged amino acid and a hydrophobic amino acid, and wherein at least one amino acid of $A_1$-$A_5$ (SEQ ID NO: 46) can be a positively charged amino acid and at least one amino acid of $A_1$-$A_5$ (SEQ ID NO: 46) can be a hydrophobic amino acid; and the negative peptide can include 5 amino acids ($B_1$-$B_5$ (SEQ ID NO: 47) as set forth sequentially from C to N terminus), wherein $B_1$, $B_2$, $B_3$, $B_4$, and $B_5$ can each be independently selected from a negatively charged amino acid and a hydrophobic amino acid, and wherein at least one amino acid of $B_1$-$B_5$ (SEQ ID NO: 47) can be a negatively charged amino acid and at least one amino acid of $B_1$-$B_5$ (SEQ ID NO: 47) can be a hydrophobic amino acid.

In some embodiments, the positive peptide and the negative peptide can each include three additional amino acids such that the positive peptide can include: 7 amino acids ($A_1$-$A_7$ (SEQ ID NO: 48) as set forth sequentially from C to N terminus), wherein $A_1$, $A_2$, $A_3$, $A_4$, $A_5$, $A_6$, and $A_7$, can each be independently selected from a positively charged amino acid and a hydrophobic amino acid, and wherein at least one amino acid of $A_1$-$A_7$ (SEQ ID NO: 48) can be a positively charged amino acid and at least one amino acid of $A_1$-$A_7$ (SEQ ID NO: 48) can be a hydrophobic amino acid; and the negative peptide can include: 7 amino acids ($A_1$-$A_7$ (SEQ ID NO: 48) as set forth sequentially from C to N terminus), wherein $A_1$, $A_2$, $A_3$, $A_4$, $A_5$, $A_6$, and $A_7$, can each be independently selected from a positively charged amino acid and a hydrophobic amino acid, and wherein at least one amino acid of $A_1$-$A_7$ (SEQ ID NO: 48) can be a positively charged amino acid and at least one amino acid of $A_1$-$A_7$ (SEQ ID NO: 48) can be a hydrophobic amino acid. In some embodiments, the positive peptide can include at least 11 amino acids ($A_1$-$A_{11}$ (SEQ ID NO: 50) as set forth sequentially from C- to N-terminus), wherein $A_1$, $A_9$, and An can each be a polar or a cationic amino acid, wherein $A_2$ can be a polar amino acid, wherein $A_3$ can be a cationic or a polar amino acid, wherein $A_4$, $A_6$, and $A_8$ can each be a hydrophobic amino acid. wherein $A_5$ and $A_7$ can each be a cationic amino acid or a polar amino acid, wherein $A_{10}$ can be a polar amino acid, and wherein the negative peptide can include at least 11 amino acids amino acids ($B_1$-$B_{11}$ (SEQ ID NO: 51) as set forth sequentially from C to N terminus), wherein $B_1$ and $B_{11}$ can each be a polar or an anionic amino acid, wherein $B_2$ and $B_{10}$, can each be a polar amino acid, wherein $B_3$, $B_5$, $B_7$, and $B_9$, can each be an anionic amino acid or a polar amino acid, and wherein $B_4$, $B_6$, and $B_8$, can each be a hydrophobic amino acid. In some embodiments, the positive peptide can have a sequence of SEQ ID NO: 1, 3, 5, 6, or 8. In some embodiments, the negative peptide can have a sequence of SEQ ID NO: 2, 4, or 7. In some embodiments, the stimulating condition can be an aqueous solution having a pH ranging from about 6.5 to about 8.5. In some embodiments, the positive peptide, the negative peptide, or the positive and the negative peptide can each further include one or more cargo polypeptides coupled to the N-terminus, the C terminus, or both the N-terminus and the C-terminus of the positive peptide, the negative peptide, or both the positive and the negative peptide. The positively charged amino acids can each be independently selected from the group consisting of: lysine, histidine, and arginine. In some embodiments, the negatively charged amino acids can each be independently selected from the group consisting of: aspartate and glutamate. In some embodiments, the hydrophobic amino acids can each be independently selected from the group consisting of: glycine, alanine, valine, leucine, methionine, isoleucine, phenylalanine, tyrosine, and tryptophan.

Also described herein are supramolecular structures that can include a positive peptide that can include at least 4 amino acids ($A_1$-$A_4$) (SEQ ID NO: 44), as set forth sequentially from C to N terminus), wherein $A_1$, $A_2$, $A_3$, and $A_4$, can each be independently selected from a positively charged amino acid and a hydrophobic amino acid, and wherein at least one amino acid of $A_1$-$A_4$ (SEQ ID NO: 44) can be a positively charged amino acid and at least one amino acid of $A_1$-$A_4$ (SEQ ID NO: 44) can be a hydrophobic amino acid; and a negative peptide that can be at least 4 amino acids ($B_1$-$B_4$) (SEQ ID NO: 45), wherein $B_1$, $B_2$, $B_3$, and $B_4$ can each be independently selected from a negatively charged amino acid and a hydrophobic amino acid, and wherein at least one amino acid of $B_1$-$B_4$ (SEQ ID NO: 45) can be a negatively charged amino acid and at least one amino acid of $B_1$-$B_4$ (SEQ ID NO: 45) can be a hydrophobic amino acid, wherein the positive and the negative peptide can be attached to each other via electrostatic interactions. In some embodiments of a supramolecular structure, the positive peptide and the negative peptide each can include an additional amino acid such that the positive peptide can include: at least 5 amino acids ($A_1$-$A_5$ (SEQ ID NO: 46) as set forth sequentially from C to N terminus), wherein $A_1$, $A_2$, $A_3$, $A_4$, and $A_5$, can each be independently selected from a positively charged amino acid and a hydrophobic amino acid, and wherein at least one amino acid of $A_1$-$A_5$ (SEQ ID NO: 46) can be a positively charged amino acid and at least one amino acid of $A_1$-$A_5$ (SEQ ID NO: 46) can be a hydrophobic amino acid; and the negative peptide can include: at least 5 amino acids ($B_1$-$B_5$ (SEQ ID NO: 47) as set forth sequentially from C to N terminus), wherein $B_1$, $B_2$, $B_3$, $B_4$, and $B_5$ can each be independently selected from a negatively charged amino acid and a hydrophobic amino acid, and wherein at least one amino acid of $B_1$-$B_5$ (SEQ ID NO: 47) can be a negatively charged amino acid and at least one amino acid of $B_1$-$B_5$ (SEQ ID NO: 47) can be a hydrophobic amino acid. In some embodiments of a supramolecular, the positive peptide and the negative peptide can each include three additional amino acids such that the positive peptide contains: at least 7 amino acids ($A_1$-$A_7$ (SEQ ID NO: 48) as set forth sequentially from C to N terminus), wherein $A_1$, $A_2$, $A_3$, $A_4$, $A_5$, $A_6$, and $A_7$, can each be independently selected from a positively charged amino acid and a hydrophobic amino acid, and wherein at least one amino acid of $A_1$-$A_7$ (SEQ ID NO: 48) can be a positively charged amino acid and at least one amino acid of $A_1$-$A_7$ (SEQ ID NO: 48) can be a hydrophobic amino acid; and the negative peptide can include: at least 7 amino acids ($A_1$-$A_7$(SEQ ID NO: 48) as set forth sequentially from C to N terminus), wherein $A_1$, $A_2$, $A_3$, $A_4$, $A_5$, $A_6$, and $A_7$, can each be independently selected from a positively charged amino acid and a hydrophobic amino acid, and wherein at least one amino acid of $A_1$-$A_7$ (SEQ ID NO: 48) can be a positively charged amino acid and at least one amino acid of $A_1$-$A_7$ (SEQ ID NO: 48) can be a hydrophobic amino acid. In some embodiments of a supramolecular structure, the positive peptide can include at least 11 amino acids ($A_1$-$A_{11}$ (SEQ ID NO: 50) as set forth sequentially from C- to N-terminus), wherein $A_1$, $A_9$, and $A_{11}$ are each a polar or a cationic amino acid, wherein $A_2$ can be a polar amino acid, wherein $A_3$ can be a cationic or a polar amino acid, wherein $A_4$, $A_6$, and $A_8$ can each be a hydrophobic amino acid, wherein $A_5$ and $A_7$ can each be a cationic amino acid or a polar amino acid, wherein $A_{10}$ can be a polar amino acid, and wherein the negative peptide can include at least 11 amino acids amino acids ($B_1$-$B_{11}$ (SEQ ID NO: 51) as set forth sequentially from C to N terminus), wherein $B_1$ and $B_{11}$ can each be a polar or an anionic amino acid, wherein $B_2$ and $B_{10}$, can each be polar amino acids, wherein $B_3$, $B_5$, $B_7$, and $B_9$, can each an anionic amino acid or a polar amino acid, and wherein $B_4$, $B_6$, and $B_8$, can each be a hydrophobic amino acid. In some embodiments of the supramolecular structure, the positive peptide, the negative peptide, or the positive and the negative peptide can each further include one or more cargo polypeptides coupled to the N-terminus, the C terminus, or both the N-terminus and the C-terminus of the positive peptide, the negative peptide, or both the positive and the negative peptide.

Also provided herein are methods that can include the steps of mixing a positive peptide and a negative peptide in a solution at a pH ranging from about 6.5 to about 8.5, at least 3 amino acids ($A_1$-$A_3$, as set forth sequentially from C to N terminus), wherein $A_1$, $A_2$, and $A_3$ can be each independently selected from a positively charged amino acid and a hydrophobic amino acid, and wherein at least one amino acid of $A_1$-$A_3$ can be a positively charged amino acid and at least one amino acid of $A_1$-$A_3$ can be a hydrophobic amino acid; and a negative peptide can include at least 3 amino acids ($B_1$-$B_3$), wherein $B_1$, $B_2$, and $B_3$ can each be independently selected from a negatively charged amino acid and a hydrophobic amino acid, and wherein at least one amino acid of $B_1$-$B_3$ can be a negatively charged amino acid and at least one amino acid of $B_1$-$B_3$ can be a hydrophobic amino acid.

In some embodiments, the positive peptide can include at least 4 amino acids ($A_1$-$A_4$ (SEQ ID NO: 44), as set forth sequentially from C to N terminus), wherein $A_1$, $A_2$, $A_3$, and $A_4$, can each be independently selected from a positively charged amino acid and a hydrophobic amino acid, and wherein at least one amino acid of $A_1$-$A_4$ (SEQ ID NO: 44) can be a positively charged amino acid and at least one amino acid of $A_1$-$A_4$ (SEQ ID NO: 44) can be a hydrophobic amino acid; and wherein the negative peptide comprises at least 4 amino acids ($B_1$-$B_4$) (SEQ ID NO: 45), wherein $B_1$, $B_2$, $B_3$, and $B_4$ can each be independently selected from a negatively charged amino acid and a hydrophobic amino acid, and wherein at least one amino acid of $B_1$-$B_4$ (SEQ ID NO: 45) can be a negatively charged amino acid and at least one amino acid of $B_1$-$B_4$ (SEQ ID NO: 45) can be a hydrophobic amino acid. The positive peptide and the negative amino acid can each include an additional amino acid such that the positive peptide can include at least 5 amino acids ($A_1$-$A_5$ (SEQ ID NO: 46) as set forth sequentially from C to N terminus), wherein $A_1$, $A_2$, $A_3$, $A_4$, and $A_5$, can each be independently selected from a positively charged amino acid and a hydrophobic amino acid, and wherein at least one amino acid of $A_1$-$A_5$ (SEQ ID NO: 46) can be a positively charged amino acid and at least one amino acid of $A_1$-$A_5$ (SEQ ID NO: 46) can be a hydrophobic amino acid; and wherein the negative peptide can include: at least 5 amino acids ($B_1$-$B_5$ (SEQ ID NO: 47) as set forth sequentially from C to N terminus), wherein $B_1$, $B_2$, $B_3$, $B_4$, and $B_5$ can each be independently selected from a negatively charged amino acid and a hydrophobic amino acid, and wherein at least one amino acid of $B_1$-$B_5$ (SEQ ID NO: 47) can be a negatively charged amino acid and at least one amino acid of $B_1$-$B_5$ (SEQ ID NO: 47) can be a hydrophobic amino acid.

In some embodiments, the positive peptide and the negative amino acid can each include three additional amino acids such that the positive peptide includes: at least 7 amino acids ($A_1$-$A_7$ (SEQ ID NO: 48) as set forth sequentially from C to N terminus), wherein $A_1$, $A_2$, $A_3$, $A_4$, $A_5$, $A_6$, and $A_7$, can each be independently selected from a positively charged amino acid and a hydrophobic amino acid, and wherein at least one amino acid of $A_1$-$A_7$ (SEQ ID NO: 48) can be a positively charged amino acid and at least one amino acid of $A_1$-$A_7$ (SEQ ID NO: 48) can be a hydrophobic amino acid; and the negative peptide can include: at least 7 amino acids ($A_1$-$A_7$(SEQ ID NO: 48) as set forth sequentially from C to N terminus), wherein $A_1$, $A_2$, $A_3$, $A_4$, $A_5$, $A_6$, and $A_7$, can each be independently selected from a positively charged amino acid and a hydrophobic amino acid, and wherein at least one amino acid of $A_1$-$A_7$ (SEQ ID NO: 48) can be a positively charged amino acid and at least one amino acid of $A_1$-$A_7$ (SEQ ID NO: 48) can be a hydrophobic amino acid.

In some embodiments, the positive peptide can include at least 11 amino acids ($A_1$-$A_{11}$ (SEQ ID NO: 50) as set forth sequentially from C- to N-terminus), wherein $A_1$, $A_9$, and $A_{11}$ can each be a polar or a cationic amino acid, wherein $A_2$ can be a polar amino acid, wherein $A_3$ can be a cationic or a polar amino acid, wherein $A_4$, $A_6$, and $A_8$ can each be a hydrophobic amino acid, wherein $A_5$ and $A_7$ are can each be independently selected from a cationic amino acid or a polar amino acid, wherein $A_{10}$ can be a polar amino acid, and wherein the negative peptide can include at least 11 amino acids amino acids ($B_1$-$B_{11}$ (SEQ ID NO: 51) as set forth sequentially from C to N terminus), wherein $B_1$ and $B_{11}$ can each be independently selected from a polar or an anionic amino acid wherein $B_2$ and $B_{10}$, can each be polar amino acids, wherein $B_3$, $B_5$, $B_7$, and $B_9$, can each be independently selected from an anionic amino acid or a polar amino acid, and wherein $B_4$, $B_6$, and $B_8$, can each be a hydrophobic amino acid.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 2A-2G show some embodiments of positive peptide segments (FIGS. 2A, 2C, 2E and 2G) and negative peptide segment(s) (FIGS. 2B, 2D, and 2F).

FIG. 6 shows embodiments of a positive (SEQ ID NO: 1) (CATCH (+)) and negative (SEQ ID NO: 2) (CATCH (−)) peptide segments.

FIGS. 7A-7B show general schematics of designs of CATCH peptides, detailing placement of anionic, cationic, hydrophobic, and polar amino acids.

FIG. 12 demonstrates the results from Sanger sequencing of CATCH(−)GFP inserted in pET21d followed by its translated amino acid sequence.

FIG. 13 demonstrates the results from Sanger sequencing of mCATCH(−)GFP insert in pET21d followed by its translated amino acid sequence.

FIG. 24A shows fluorescence emission spectra of CATCH(−)GFP and mCATCH(−) GFP. FIG. 24B shows a SEC of CATCH(−)GFP and mCATCH(−)GFP (inset: native PAGE gel of CATCH(−) GFP (right) and mCATCH(−)GFP (left)).

FIGS. 27A-27B show fluorescence photomicrograph (FIG. 27A) and transmission electron micrograph (FIG. 27B) of CATCH(−), CATCH(+), and CATCH(−)GFP tri-assemblies.

FIGS. 28A-28B show fluorescence photomicrographs of tri-assembly controls, CATCH(−) GFP alone (FIG. 28A) or mCATCH(−)GFP, CATCH(+), CATCH(−) (FIG. 28B).

FIGS. 29A-29B show fluorescence photomicrograph (FIG. 29A) and transmission electron micrograph (FIG. 29B) of CATCH(+) and CATCH(−)GFP di-assemblies.

FIGS. 30A-30B show fluorescence photomicrographs of di-assembly controls, CATCH(−) GFP alone (FIG. 30A) or mCATCH(−)GFP plus CATCH(+) (FIG. 30B).

FIGS. 32A-32F show fluorescence photomicrographs of fluorescent supramolecular di-assembly microparticles after (FIG. 32A) 15 hours of static incubation, (FIG. 32B) 10 minutes of stirring, and (FIG. 32C) 60 minutes of stirring, or commercially-available fluorescent microspheres with diameters of (FIG. 32D) 1 µm, (FIG. 32E) 2 µm, or (FIG. 32F) 9.9 µm. FIGS. 32G-32I show histograms of DLS intensity of solutions of CATCH(−)GFP and CATCH(+) (FIG. 32G) after 15 hours of static incubation, (FIG. 32H) 10 minutes of stirring, and (FIG. 32I) 60 minutes of stirring.

FIGS. 35A-35G show the formation of macroscopic hydrogels with an integrated folded protein. Digital still images of (FIG. 35A) aqueous buffered solutions of CATCH (+) (top) and CATCH(−) (bottom) alone, and (FIG. 35B) after mixing at a 1:1 (v/v) ratio to induce hydrogel formation. * Red food coloring added to samples for ease of viewing. FIGS. 35C and 35D show blue-light transilluminated digital still images of tri-assembly hydrogels fabricated by mixing CATCH(−) and CATCH(+) with 0.75 µM CATCH(−)GFP (FIG. 35C) or 0.75 µM mCATCH(−)GFP (FIG. 35D) before and after 48 incubation under excess 1× PBS. FIGS. 35E-35G show blue-light transilluminated digital still images assessing time-dependent GFP retention within tri-assembly hydrogels fabricated from mixtures of CATCH(−) and CATCH(+) with 0.75 UM CATCH(−)GFP (left, black bars) or 0.75 µM mCATCH(−)GFP (right, gray bars).

FIGS. 40A-40B show graphs demonstrating ThT endpoint analysis (FIG. 40A) and ThT kinetic analysis (FIG. 40B) of different CATCH combinations.

FIGS. 42A-42H show images and graphs demonstrating the characterization of CATCH-GFP fusion proteins and their integration into CATCH fibers.

FIGS. 50A-50C show DNA sequence (FIG. 50A) that can encode an amino acid sequence (FIG. 50B) of a CATCH(6-). The DNA sequence of FIG. 50A can be recombinantly expressed in an expression vector to produce the protein sequence of FIG. 50B. FIG. 50C. shows a table of some of the specific features of the DNA sequence of FIG. 50A and the polypeptide of FIG. 50B.

FIGS. 53A-53B shows a DNA sequence (FIG. 53A) and the encoded KSI-CATCH(6-) polypeptide (FIG. 53B), where CATCH(6-) can be replaced with any CATCH peptide. FIG. 53C shows a table with some of the features of the DNA sequence of FIG. 53A and the polypeptide of FIG. 53B.

DETAILED DESCRIPTION

Figure 1:
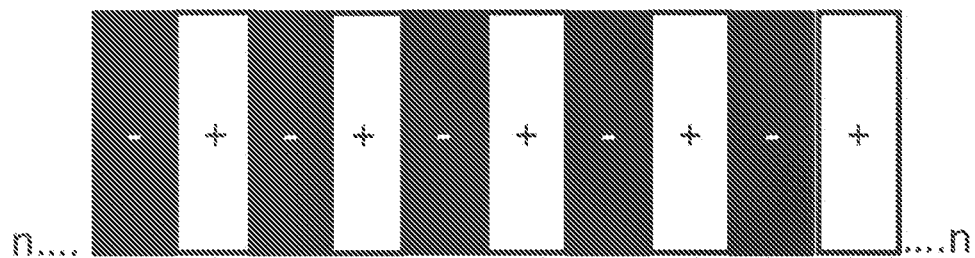
FIG. 1 shows the general layout of nanofiber that can be formed from the self-assembly of two or more charge complementary peptides (i.e. co-assembly peptides) provided herein. The black segments with a (−) denote a peptide segment with an overall anionic charge (negative peptide segment). The white segments with a (+) denote a peptide segment with an overall cationic charge (positive peptide segment). The n corresponds to any number of additional charge-complementary segments.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, and the like, which are within the skill of the art. Such techniques are explained fully in the literature.

Definitions

As used herein, As used herein, "about," "approximately," and the like, when used in connection with a numerical variable, can generally refers to the value of the variable and to all values of the variable that are within the experimental error (e.g., within the 95% confidence interval for the mean) or within +/−10% of the indicated value, whichever is greater.

As used herein, "antibody" can refer to a glycoprotein containing at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen.

As used herein, "anti-infective" can refer to compounds or molecules that can either kill an infectious agent or inhibit it from spreading. Anti-infectives include, but are not limited to, antibiotics, antibacterials, antifungals, antivirals, and antiprotozoans.

As used herein, "aptamer" can refer to single-stranded DNA or RNA molecules that can bind to pre-selected targets including proteins with high affinity and specificity. Their specificity and characteristics are not directly determined by their primary sequence, but instead by their tertiary structure.

As used herein, "attached," "attachment" and the like can refer to the formation of a covalent or non-covalent association (e.g. a bond) between two or more molecules or conjugation of two or more molecules. As used herein, "attached," "attachment" and the like can refer to direct association of two or more molecules together with no intermediate molecules between those that are attached together or to the indirect attachment of two or more molecules together that is mediated via one or more linkers. Where the association is non-covalent, this can encompass charge interactions, affinity interactions, metal coordination, physical adsorption, host-guest interactions, hydrophobic interactions, pi-pi stacking interactions, hydrogen bonding interactions, van der Waals interactions, magnetic interactions, electrostatic interactions, dipole-dipole interactions, and/or combinations thereof. Where the association is covalent, this can encompass bonds where a pair of electrons is shared between one or more atoms in each molecule involved.

As used herein, "cargo polypeptide" can refer to any peptide polypeptide that can be coupled to the N- and/or the C-terminus of a positive or negative peptide segment as provided herein. The cargo polypeptide can be coupled to the positive or negative peptide segment using standard molecular biology and recombinant DNA technology techniques. For example a fusion peptide segment containing the cargo polypeptide, can be produced from a recombinant DNA construct containing DNA encoding the negative or positive peptide segment operatively coupled with DNA encoding the cargo polypeptide and any optional linker. The DNA encoding the negative or positive peptide segment can be operatively coupled to the cargo polypeptide and any optional linker such that the cargo polypeptide is translated in-frame with negative or positive peptide segment. The cargo polypeptide can be a reporter protein (e.g. a fluorescent protein), a pharmaceutically relevant protein (a protein that can be effective to prevent or treat a disease or symptom thereof in a subject), a cell- or tissue-targeting protein, an antibody or fragment thereof, an antigen, an enzyme, a growth factor, a cytokine, a chemokine, an extracellular matrix protein or fragment thereof, a transmembrane receptor or fragment thereof, a toxin or a fragment thereof, and a transcription factor or fragment thereof.

As used herein, "cDNA" can refer to a DNA sequence that is complementary to a RNA transcript in a cell. It is a man-made molecule. Typically, cDNA is made in vitro by an enzyme called reverse-transcriptase using RNA transcripts as templates.

As used herein, "chemotherapeutic agent" or "chemotherapeutic" can refer to a therapeutic agent utilized to prevent or treat a cancer.

As used herein, "coupled" can refer to the direct or indirect (e.g. via a linker) attachment of two or more molecules and/or compounds.

As used herein, "concentrated" can refer to a molecule or population thereof, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "control" can refer to an alternative subject or sample used in an experiment for comparison purpose and included to minimize or distinguish the effect of variables other than an independent variable.

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "DNA molecule" can include nucleic acids/polynucleotides that are made of DNA. As used herein, "expression" can refer to the process by which polynucleotides are transcribed into RNA transcripts. In the context of mRNA and other translated RNA species, "expression" also refers to the process or processes by which the transcribed RNA is subsequently translated into peptides, polypeptides, or proteins. Techniques and methods appropriate for determining an amount of expression will be instantly appreciated by those of ordinary skill in the art and include, but are not limited to, western blotting for the transcribed protein, pyro-sequencing, polymerase chain reaction (PCR) based methods (e.g. reverse transcription PCR and quantitative real-time PCR), and mass-spectrometric based analysis.

As used herein, the term "encode" can refer to principle that DNA can be transcribed into RNA, which can then be translated into amino acid sequences that can form proteins.

As used herein, the term "enzyme" can refer to any protein that can catalyze a chemical or biochemical reaction.

As used herein, the term "fluorescent protein" can refer to any protein that can produce fluorescence when excited by the proper excitation wavelength or by other resonance transfer of energy, e.g. FRET. The term "fluorescent protein" includes, but is not limited to, all types and variants of current fluorescent proteins known in the art, include but not limited to green fluorescent proteins, yellow fluorescent proteins, blue fluorescent proteins, cyan fluorescent proteins, red fluorescent proteins, etc. The term "fluorescent protein" include, without limitation, all forms of such proteins as they are routinely modified, derivitized, and generally known to those of ordinary skill in the art. For example "green fluorescent protein" includes, without limitation, enhanced green fluorescent protein (eGFP), redox sensitive GFP (roGFP), and all color mutants. The amino acid sequences and other characteristics of suitable fluorescent proteins will be known to those of skill in the art and are within the scope of this disclosure.

As used herein, "gene" can refer to a hereditary unit corresponding to a sequence of DNA that occupies a specific location on a chromosome and that contains the genetic instruction for a characteristic(s) or trait(s) in an organism. The term gene can refer to both translated and untranslated regions of a subject's genome.

As used herein, "identity," "identical to", and the like can refer to the relationship between two or more nucleotide or polypeptide sequences, as determined by comparing the sequences. In the art, "identity" also refers to the degree of sequence relatedness between nucleotide or polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure, unless stated otherwise.

As used herein, "immunomodulator," can refer to an agent, such as a therapeutic agent, which is capable of modulating or regulating one or more immune function or response.

As used herein, "isolated" can mean separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "linker" can refer to any amino acid or peptide that can be optionally included between a positive or negative peptide segment and a cargo protein. The linker can range in length from about 1 to about 60 amino acids in length. The linker can be composed of any of the 20 naturally occurring amino acids and be present in any arrangement that does not otherwise perturb the peptide segment assembly or cargo protein activity.

As used herein, "mammal," for the purposes of treatments, can refer to any animal classified as a mammal, including human, domestic and farm animals, nonhuman primates, and zoo, sports, or pet animals, such as, but not limited to, dogs, horses, cats, and cows.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein. As used herein, "nucleic acid sequence" and "oligonucleotide" also encompasses a nucleic acid and polynucleotide as defined above.

As used herein, "operatively linked" can indicate that the regulatory sequences useful for expression of the coding sequences of a nucleic acid are placed in the nucleic acid molecule in the appropriate positions relative to the coding sequence so as to effect expression of the coding sequence. This same term can be applied to the arrangement of coding sequences and/or transcription control elements (e.g. promoters, enhancers, and termination elements), and/or selectable markers in an expression vector. "Operatively linked" can also refer to an indirect attachment (i.e. not a direct fusion) of two or more polynucleotide sequences or polypeptides to each other via a linking molecule (also referred to herein as a linker).

As used herein, "nucleic acid sequence" and "oligonucleotide" can also encompass a nucleic acid and polynucleotide as defined above.

As used herein, "overexpressed" or "overexpression" can refer to an increased expression level of an RNA or protein product encoded by a gene as compared to the level of expression of the same or different RNA or protein product in the same cell type or population thereof or a different cell type, normal cell, and/or control cell or any population thereof. Typically, expression is stated as an increase in the fold-change when determined relatively. The amount of overexpression can also be expressed as a quantitative amount. Techniques are known to those of ordinary skill in the art that can determine the absolute number of molecules of RNA or protein product. Therefore, overexpression can be stated as an amount of the RNA molecule or protein product of interest as compared to a control RNA or protein product (e.g. GAPDH, beta-actin) in the same cell or population thereof, or a different cell or population there of (e.g. different cell type, normal cell, and/or control cell or any population thereof). In the case of overexpression the absolute amount of the RNA molecule or protein product of interest will be less than that of the other RNA or protein product in the same or different cell type that is being used for comparison.

As used herein "peptide" refers to chains of at least 2 amino acids that are short, relative to a protein or polypeptide.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" can refer to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" can refer to any acid or base addition salt whose counter-ions are non-toxic to the subject to which they are administered in pharmaceutical doses of the salts.

As used herein, "plasmid" as used herein can refer to a non-chromosomal double-stranded DNA sequence including an intact "replicon" such that the plasmid is replicated in a host cell.

As used herein, "positive control" can refer to a "control" that is designed to produce the desired result, provided that all reagents are functioning properly and that the experiment is properly conducted.

As used herein, "protein" as used herein can refer to a molecule composed of one or more chains of amino acids in a specific order. The term protein is used interchangeable with "polypeptide." The order is determined by the base sequence of nucleotides in the gene coding for the protein.

Proteins are required for the structure, function, and regulation of the body's cells, tissues, and organs.

As used herein, "preventative" and "prevent" can refer to hindering or stopping a disease or condition before it occurs, even if undiagnosed, or while the disease or condition is still in the sub-clinical phase.

As used herein, "purified" or "purify" can be used in reference to a nucleic acid sequence, peptide, or polypeptide that has increased purity relative to the natural environment.

As used herein, the term "recombinant" or "engineered" can generally refer to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc. Recombinant or engineered can also refer to the polypeptide encoded by the recombinant nucleic acid. Non-naturally occurring nucleic acids or polypeptides include nucleic acids and polypeptides modified by man.

As used herein, "separated" can refer to the state of being physically divided from the original source or population such that the separated compound, agent, particle, or molecule can no longer be considered part of the original source or population.

As used interchangeably herein, "subject," "individual," or "patient" can refer to a vertebrate organism, such as a mammal (e.g. human).

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof. The effect can be therapeutic in terms of a partial or complete cure of a disease, condition, symptom or adverse effect attributed to the disease, disorder, or condition. The term "treatment" as used herein covers any treatment of a disease, in a mammal, particularly a human, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented.

As used herein, "underexpressed" or "underexpression" can refer to a decreased expression level of an RNA or protein product encoded by a gene as compared to the level of expression of the same or different RNA or protein product in the same cell type or population thereof or a different cell type, normal cell, and/or control cell or any population thereof. Typically, expression is stated as an increase in the fold-change when determined relatively. The amount of underexpression can also be expressed as a quantitative amount. Techniques are known to those of ordinary skill in the art that can determine the absolute number of molecules of RNA or protein product. Therefore, underexpression can be stated as an amount of the RNA molecule or protein product of interest as compared to a control RNA or protein product (e.g. GAPDH, beta-actin) in the same cell or population thereof, or a different cell or population there of (e.g. different cell type, normal cell, and/or control cell or any population thereof). In the case of underexpression the absolute amount of the RNA molecule or protein product of interest will be less than that of the other RNA or protein product in the same or different cell type that is being used for comparison.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. "Variant" can also include functional and structural variants.

As used herein, the term "vector" or is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

DISCUSSION

Self-assembly is the spontaneous organization of molecules into a precise supramolecular architecture without any external guidance. Throughout nature, biomolecule self-assembly gives rise to various functional biomaterials that can perform complex tasks, such as molecular sensing and recognition, chemical synthesis, motility, and compartmentalization, as well as multi-scale hierarchical organization. Thus, there is increasing interest in biomolecule self-assembly for bottom-up fabrication of biomaterials for medical and technological applications.

Peptides and peptide analogs that can form elongated nanofibers by adopting β-sheet secondary structures can be advantageous for creating supramolecular biomaterials. Peptide self-assembly into β-sheet nanofibers has been demonstrated to occur under mild aqueous conditions with the resultant nanofibers often undergoing sol-gel transition into macroscopic, physically-crosslinked hydrated structures (i.e. "hydrogels") above a critical concentration. The amino acid sequence of β-sheet fibrillizing peptides can be systematically modified to tailor nanofiber morphology, gelation properties, and stimuli-responsiveness according to the intended application. In addition, β-sheet peptide nanofibers can be fabricated into micron-sized gels using various conventional polymer-processing techniques. Finally, β-sheet peptide nanofibers are well-suited for use in biomedical applications because they are composed of natural amino acids that can be metabolized, they are often biocompatible with cells and tissues, and they typically elicit minimal inflammation and weak or no adaptive immunity directed against the peptide itself, despite being foreign to the host.

To be useful for medical or technological applications, supramolecular biomaterials must often demonstrate functional capabilities beyond robust self-assembly and biocompability. Since synthetic peptides designed to self-assemble typically lack any additional functional features, ligands, fluorophores, antigens, drugs, or other bioactive compounds are often installed into supramolecular biomaterials to impart functional capabilities. Supramolecular biomaterials can be functionalized post-assembly via various covalent and non-covalent grafting approaches, However, current supramolecular biomaterials suffer from several deficiencies. They often rely on complex, inefficient, or poorly reproducible reactions and may only provide transient functionality within complex biological environments.

Alternatively, functional capabilities can be installed directly into supramolecular biomaterials via covalent fusion of a functional molecule and a self-assembling peptide in the pre-assembled state (i.e. "fusion peptides"). Installing functional molecules with more sophisticated properties, such as catalysis, selective molecular recognition, tunable visible light fluorescence, or precise antigen conformation, could impart unprecedented functional capabilities into supramolecular biomaterials already finding use in biomedical and biotechnological applications. Current self-assembling peptides rely on covalent grafting of folded proteins to the self-assembled peptides. Covalent fusions of folded proteins and self-assembling can provide many advantages over covalent grafting, particularly from a material fabrication perspective.

Despite the clear advantages of a covalent fusion approach, there are significant challenges inherent to covalent fusions from a synthesis perspective that have hindered the development and adoption of this approach in the context of self-assembling peptides. In particular, conventional peptide synthesis and purification cannot be adapted to produce protein-peptide fusions. Instead, fusion proteins are typically expressed from recombinant DNA using translational machinery housed within microbes or other cellular hosts. The environment within the cytoplasm of expression hosts is often favorable for β-sheet peptide self-assembly, however, which can hinder recovery of soluble, bioactive fusion proteins by inducing aggregation or misfolding. Self-assembly domains with slow fibrillization kinetics or pH-responsive assembly can address this limitation. However, the former requires assembly kinetics that are well-behaved under various expression conditions and with a wide variety of fusion protein partners, while the latter necessitates proteins with folded conformations that are not pH-sensitive.

With the deficiencies in the current technologies in mind, described herein are self-assembling peptides that can be engineered to resist assembly until acted upon by a stimulus that can be applied under neutral, near-physiological conditions that support maintaining protein folding and function. In some embodiments, charge-complementary peptides can contain one or more ionizable residues that renders the self-assembly of the charge-complementary peptides energetically unfavorable until the two peptides are combined in solution.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Co-Assembly Peptides and Nanostructures
Charge Complementary Peptide Segments

Figure 2A:
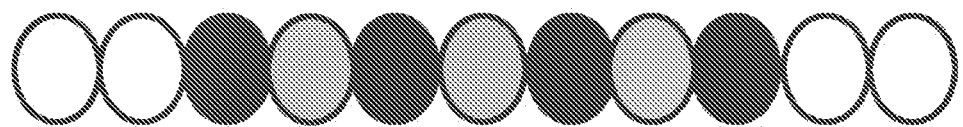
Figure 2B:
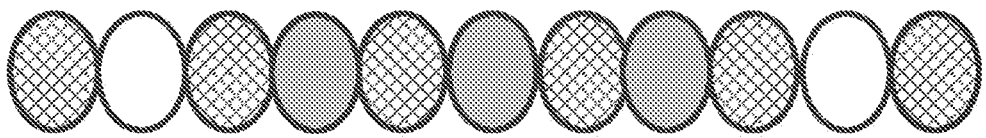

As shown in FIG. 1 provided herein are charge complementary peptide segments that self-assemble to form nanofibers and can contain 1 or more ionizable amino acids such that the charge complementary peptides do not self-assemble until contained in a neutral solution together. In some embodiments, the 1 or more ionizable amino acids are ionizable at a neutral and/or near physiologic pH. In some embodiments the neutral and/or near physiologic pH can range from about 6.5 to about 8.5 The charge complementary peptide segments can be either positive or negatively charged, which refers to the net charge (cationic or anionic) of the entire peptide segment. A general schematic of embodiments of a positive peptide is shown in FIGS. 2A, 2C, 2E, and 2G. A general schematic of embodiments of a negative peptide segment is shown in FIGS. 2B, 2D, and 2F.

A positive peptide can include at least 3 amino acids ($A_1$-$A_3$ as set forth sequentially from C to N terminus), wherein $A_1$, $A_2$, and As can each be independently selected from a positively charged amino acid and a hydrophobic amino acid, and wherein at least one amino acid of $A_1$-$A_3$ can be a positively charged amino acid and at least one amino acid of $A_1$-$A_3$ can be a hydrophobic amino acid. A negative peptide can include at least 3 amino acids ($B_1$-$B_3$ as set forth sequentially from C to N terminus), wherein $B_1$, $B_2$, and $B_3$ can each be independently selected from a negatively charged amino acid and a hydrophobic amino acid, and wherein at least one amino acid of $B_1$-$B_3$ can be a negatively charged amino acid and at least one amino acid of $B_1$-$B_3$ can be a hydrophobic amino acid. When one or more positive and one or more negative peptide segments are mixed together under stimulating conditions, they can self-assemble to form supramolecular structures. The 3 amino acids ($A_1$-$A_3$) can form a core of a larger peptide and can have additional amino acids at the N- and/or C-terminus of the 3 amino acid ($A_1$-$A_3$) core. The additional amino acids can range in number from 1, 2, 3, 4, 5, 6, 7, 8, 9, 10, 20, 30, 40, or 50 or more. The additional amino acids can each be selected from natural and unnatural amino acids, a cationic amino acid, an anionic amino acid, a hydrophobic amino acid, or a polar amino acid. In some embodiments the amino acids can be modified, such as iodinated, fluorinated, or otherwise labeled.

A positive peptide can include at least 4 amino acids ($A_1$-$A_4$ (SEQ ID NO: 44) as set forth sequentially from C to N terminus), wherein $A_1$, $A_2$, $A_3$, and $A_4$, can each be independently selected from a positively charged amino acid and a hydrophobic amino acid, and wherein at least one amino acid of $A_1$-$A_4$ (SEQ ID NO: 44) can be a positively charged amino acid and at least one amino acid of $A_1$-$A_4$ (SEQ ID NO: 44) can be a hydrophobic amino acid. A negative peptide can include at least 4 amino acids ($B_1$-$B_4$ (SEQ ID NO: 45) as set forth sequentially from C to N terminus), wherein $B_1$, $B_2$, $B_3$, and $B_4$ can each be independently selected from a negatively charged amino acid and a hydrophobic amino acid, and wherein at least one amino acid of $B_1$-$B_4$ can be a negatively charged amino acid and at least one amino acid of $B_1$-$B_4$ (SEQ ID NO: 45) can be a hydrophobic amino acid. When one or more positive and one or more negative peptide segments are mixed together under stimulating conditions, they can self-assemble to form supramolecular structures. The 4 amino acids ($A_1$-$A_4$) (SEQ ID NO: 44) can form a core of a larger peptide and can have additional amino acids at the N- and/or C-terminus of the 4 amino acid ($A_1$-$A_4$) (SEQ ID NO: 44) core. The additional amino acids can range in number from 1, 2, 3, 4, 5, 6, 7, 8, 9, 10, 20, 30, 40, or 50 or more. The additional amino acids can each be selected from natural and unnatural amino acids, a cationic amino acid, an anionic amino acid, a hydrophobic amino acid, or a polar amino acid. In some embodiments the amino acids can be modified, such as iodinated, fluorinated, or otherwise labeled.

A positive peptide can include at least 5 amino acids ($A_1$-$A_5$ (SEQ ID NO: 46) as set forth sequentially from C to N terminus), wherein $A_1$, $A_2$, $A_3$, $A_4$, and As, can each be independently selected from a positively charged amino acid and a hydrophobic amino acid, and wherein at least one amino acid of $A_1$-$A_5$ (SEQ ID NO: 46) can be a positively charged amino acid and at least one amino acid of $A_1$-$A_5$ (SEQ ID NO: 46) can be a hydrophobic amino acid. A negative peptide can include at least 5 amino acids ($B_1$-$B_5$ (SEQ ID NO: 47) as set forth sequentially from C to N terminus), wherein $B_1$, $B_2$, $B_3$, $B_4$, and $B_5$ can each be independently selected from a negatively charged amino acid and a hydrophobic amino acid, and wherein at least one amino acid of $B_1$-$B_5$ (SEQ ID NO: 47) can be a negatively charged amino acid and at least one amino acid of $B_1$-$B_5$ (SEQ ID NO: 47) can be a hydrophobic amino acid. When one or more positive and one or more negative peptide segments are mixed together under stimulating conditions, they can self-assemble to form supramolecular structures. The 5 amino acids ($A_1$-$A_5$) (SEQ ID NO: 46) can form a core of a larger peptide and can have additional amino acids at the N- and/or C-terminus of the 5 amino acid ($A_1$-$A_5$) (SEQ ID NO: 46) core. The additional amino acids can range in number from 1, 2, 3, 4, 5, 6, 7, 8, 9, 10, 20, 30, 40, or 50 or more. The additional amino acids can each be selected from natural and unnatural amino acids, a cationic amino acid, an anionic amino acid, a hydrophobic amino acid, or a polar amino acid. In some embodiments the amino acids can be modified, such as iodinated, fluorinated, or otherwise labeled.

A positive peptide can include at least 7 amino acids ($A_1$-$A_7$ (SEQ ID NO: 48) as set forth sequentially from C to N terminus), wherein $A_1$, $A_2$, $A_3$, $A_4$, $A_5$, $A_6$, and $A_7$, can each be independently selected from a positively charged amino acid and a hydrophobic amino acid, and wherein at least one amino acid of $A_1$-$A_7$ (SEQ ID NO: 48) can be a positively charged amino acid and at least one amino acid of $A_1$-$A_7$ (SEQ ID NO: 48) can be a hydrophobic amino acid. A negative peptide can include at least 7 amino acids ($B_1$-$B_7$ (SEQ ID NO: 49) as set forth sequentially from C to N terminus), wherein $B_1$, $B_2$, $B_3$, $B_4$, $B_5$, $B_6$, and $B_7$ can each be independently selected from a negatively charged amino acid and a hydrophobic amino acid, and wherein at least one amino acid of $B_1$-$B_7$ (SEQ ID NO: 49) can be a negatively charged amino acid and at least one amino acid of $B_1$-$B_7$ (SEQ ID NO: 49) can be a hydrophobic amino acid.

When one or more positive and one or more negative peptide segments are mixed together under stimulating conditions, they can self-assemble to form supramolecular structures. The 7 amino acids ($A_1$-$A_7$) (SEQ ID NO: 48) can form a core of a larger peptide and can have additional amino acids at the N- and/or C-terminus of the 5 amino acid ($A_1$-$A_7$) (SEQ ID NO: 48) core. The additional amino acids can range in number from 1, 2, 3, 4, 5, 6, 7, 8, 9, 10, 20, 30, 40, or 50 or more. The additional amino acids can each be selected from natural and unnatural amino acids, a cationic amino acid, an anionic amino acid, a hydrophobic amino acid, or a polar amino acid. In some embodiments the amino acids can be modified, such as iodinated, fluorinated, or otherwise labeled.

The positively charged amino acids (cationic amino acids) can each be independently selected from the group of lysine, histidine, and arginine. The negatively charged amino acids (anionic amino acids) can each be independently selected from the group of aspartate and glutamate. The hydrophobic amino acids can each be independently selected from the group consisting of: glycine, alanine, valine, leucine, methionine, isoleucine, phenylalanine, tyrosine, and tryptophan. In some embodiments, the positive and/or negative peptide segment can further include a cargo polypeptide coupled to the N and/or the C terminus of the peptide. Cargo polypeptides are discussed in greater detail elsewhere herein.

In some embodiments, the peptide having a net positive charge can have at least 11 amino acids ($A_1$-$A_{11}$ (SEQ ID NO: 50) as set forth sequentially from C to N terminus), wherein $A_1$, $A_9$, and $A_1$ can each be a polar or a cationic amino acid, wherein $A_2$ can be a polar amino acid, wherein $A_3$ can be a cationic or a polar amino acid, wherein $A_4$, $A_6$, and As can each be a hydrophobic amino acid, wherein $A_5$ and $A_7$ can each be a cationic amino acid or a polar amino acid, and wherein $A_{10}$ can be a polar amino acid.

In some embodiments, the negative peptide can be composed of at least 11 amino acids ($B_1$-$B_{11}$ (SEQ ID NO: 51) as set forth sequentially from C to N terminus), wherein $B_1$ and $B_{11}$ can each be a polar or an anionic amino acid, wherein $B_2$ and $B_{10}$, can each be polar amino acids, wherein $B_3$, $B_5$, $B_7$, and $B_9$, can each be an anionic or a polar amino acid, and wherein $B_4$, $B_6$, and $B_8$, can each be hydrophobic amino acids.

Suitable cationic amino acids can have positively charged side (or "R" groups) groups and can include, but are not limited to, lysine, arginine, and histidine. Suitable anionic amino acids can have negatively charged side groups and can include, but are not limited to, aspartate and glutamate. Suitable polar amino acids can have polar, uncharged side groups, and can include, but are not limited to, serine, threonine, cysteine, proline, asparagine, and glutamine. Suitable hydrophobic amino acids can have nonpolar, aliphatic or aromatic side groups and can include, but are not limited to, glycine, alanine, valine, leucine, methionine, isoleucine, phenylalanine, tyrosine, and tryptophan. All sequences resulting from employing the general scheme shown in FIGS. 2A and 2B and at least the amino acids described herein are enabled by and within the scope of this disclosure.

In some embodiments, including but not limited to those shown in e.g. FIG. 6, the positive peptide segment can have a sequence of QQKFKFKFKQQ (SEQ ID NO: 1) (also referred to herein as CATCH (4+)), KQKFKFKFKQK (SEQ ID NO: 3) (also referred to herein as CATCH (6+)), KQQFKFKFKQQ (SEQ ID NO: 5), QQKFQFQFKQQ (SEQ ID NO: 6) (also referred to herein as CATCH (2+)), or KQQFKFKFQQK (SEQ ID NO: 8) (also referred to herein as CATCH (*4+). In some embodiments, the negative peptide segment can have a sequence of EQEFEFEFEQE (SEQ ID NO: 2) (also referred to herein as CATCH (6-)), QQEFEFEFEQQ (SEQ ID NO: 4) (also referred to herein as CATCH (4-)), QQEFQFQFEQQ (SEQ ID NO: 7) (also referred to herein as CATCH (2-)).

The positive and negative peptide segments can be produced from DNA that can encode the positive and negative peptide segments. Based on the amino acid sequences provided herein, one of ordinary skill in the art will know techniques and methods that will enable them to generate suitable coding DNA sequences for the peptide segments. In some embodiments, the DNA that can encode the positive and negative peptide segments can be codon optimized for expression in a particular cell type, such as *E. coli*. Codon optimization techniques will be appreciated by those of skill in the art. The peptide segment encoding DNA can be included in a suitable expression vector. Suitable expression vectors will be appreciated by those of ordinary skill in the art. In some embodiments, the expression vector can also express genes that can result in more efficient and/or accurate protein folding and other post-translation modifications. Such expression vectors will be appreciated by those of ordinary skill in the art. The expression vectors can be introduced into a suitable cells and the polypeptides can be produced by expression in the cells and harvested using techniques generally known in the art.

Cargo Polypeptide Fusion Charge Complementary Peptide Segments

Figure 3:
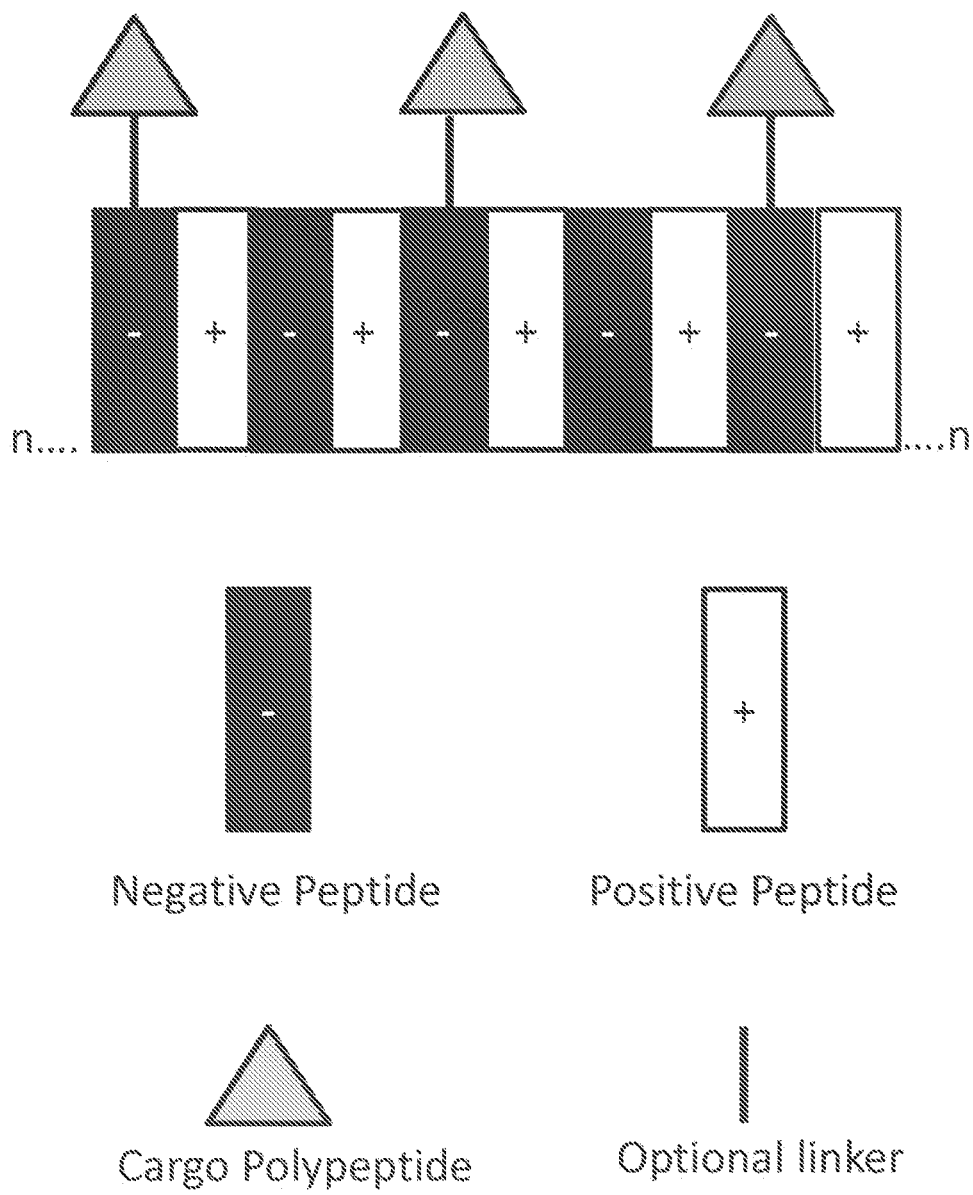
FIG. 3 shows embodiments of the nanofiber of FIG. 1 further containing a cargo polypeptide that can be coupled to one or more of the negative peptide segments via an optional linker.
Figure 4:
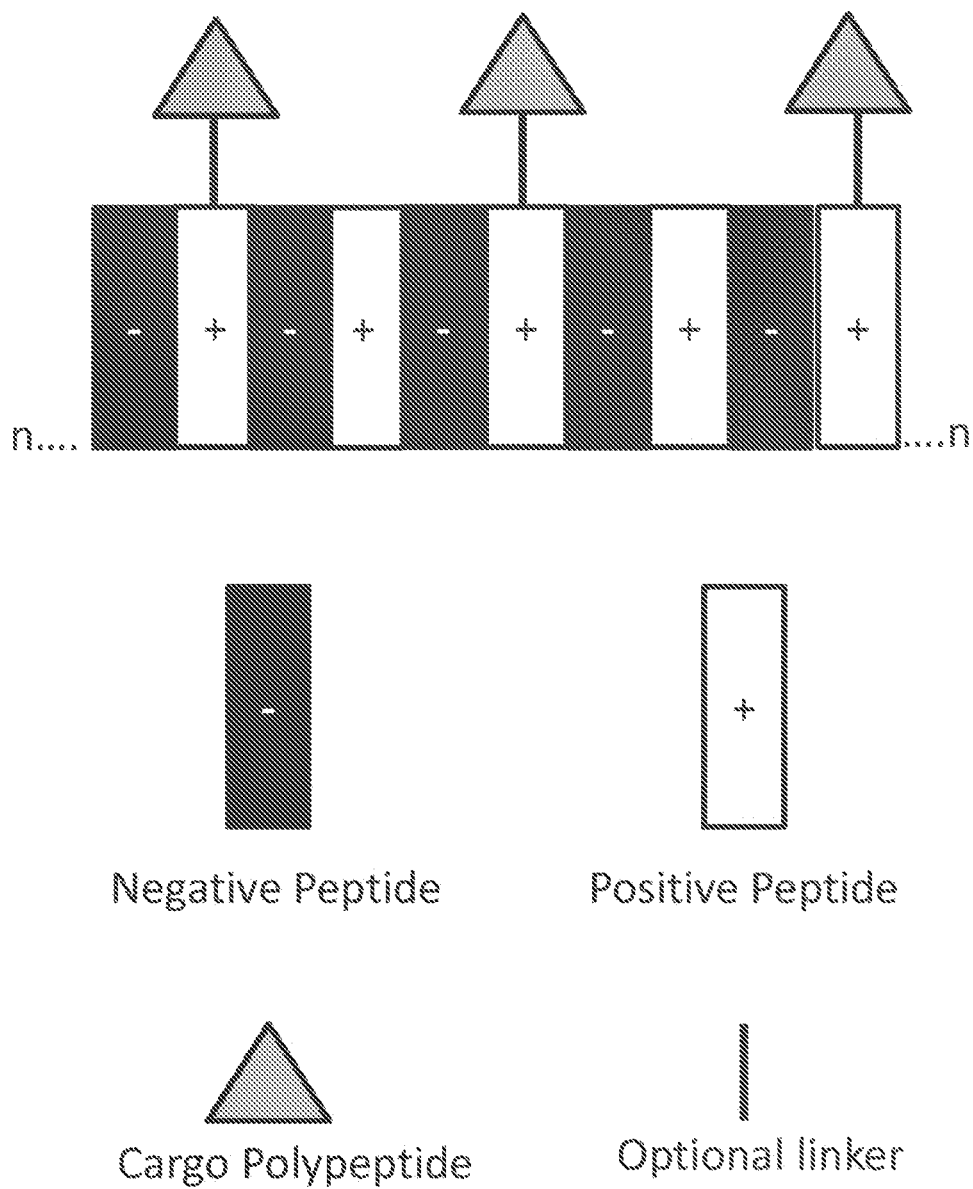
FIG. 4 shows embodiments of the nanofiber of FIG. 1 further containing a cargo polypeptide that can be coupled to one or more of the positive peptide segments via an optional linker.
Figure 5:
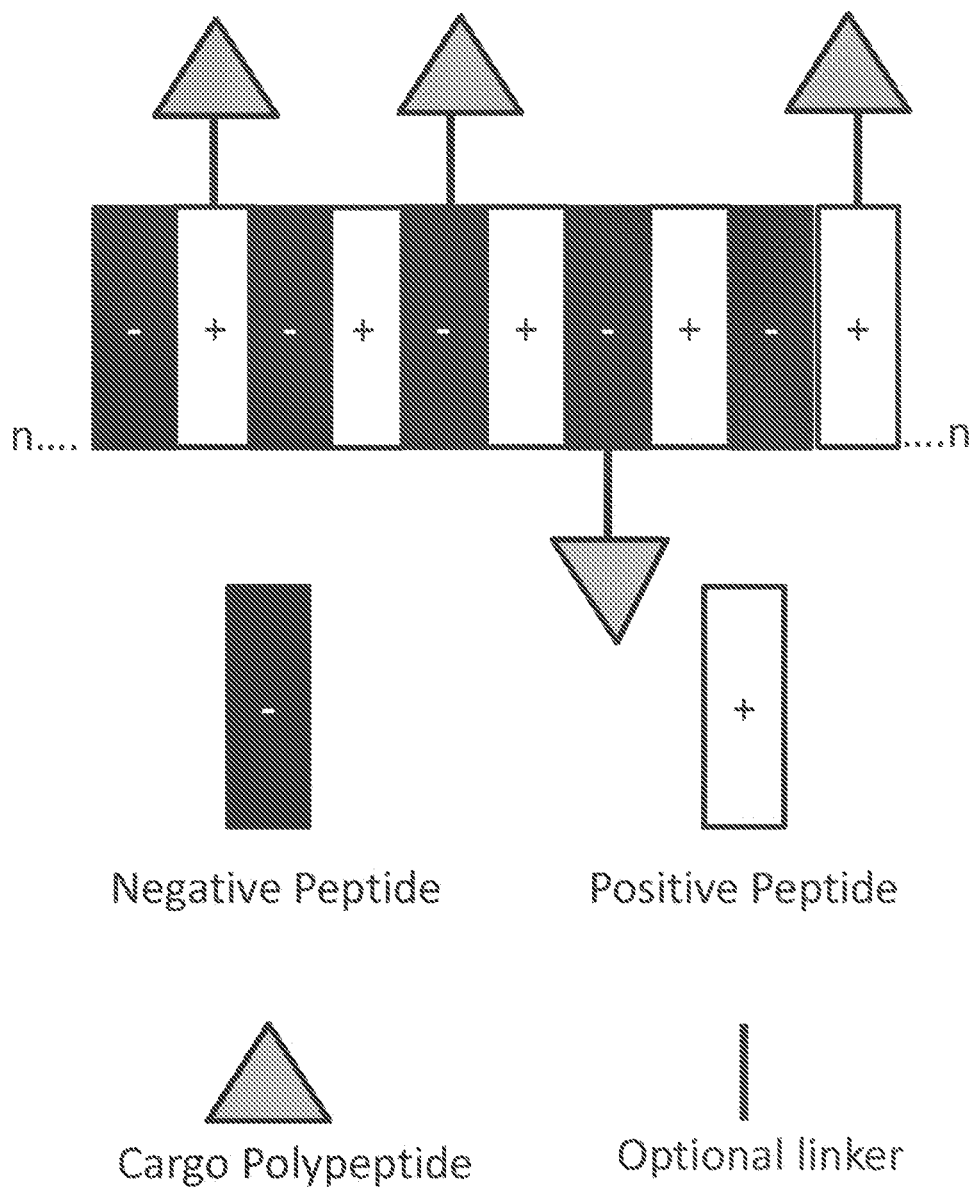
FIG. 5 shows embodiments of the co-assembly peptides and polypeptides further containing a cargo polypeptide that can be coupled to the negative and/or positive peptide segments.

As shown in FIGS. 3-5, the nanofibers formed from the self-assembly of the charge-complementary peptide segments can further contain a cargo polypeptide coupled to the peptide segment (also referred to herein as cargo-polypeptide fusion charged complementary peptide segments, cargo-polypeptide fusion charged positive peptide segment, cargo-polypeptide fusion charged negative peptide segment, as the context demands). The cargo polypeptide can be coupled to one or more of the positive and/or negative peptide segments. The cargo polypeptide can be coupled directly (e.g. no amino acids existing between the N terminus of the peptide segment and the C-terminus of the cargo polypeptide) to the amino acid sequence of a positive or negative peptide segment. The cargo polypeptide can be coupled indirectly, e.g. via an optional linker, to a positive or negative peptide sequence. The linker can be any amino acid sequence ranging from 1 to 60 amino acids. The linker can be composed of any of the 20 naturally occurring amino acids, which can be present in any arrangement that does not perturb the assembly behavior of the peptide segment and/or the bioactivity of the cargo protein.

The cargo polypeptide can be coupled to the positive or negative peptide segment using standard molecular biology and recombinant DNA technology techniques. The cargo polypeptide fusion charged complementary peptide segments can be produced from DNA that can encode the cargo polypeptide charge complementary peptide segments. Based on the amino acid sequences provided herein, one of ordinary skill in the art will know techniques and methods that will enable them to generate suitable coding DNA sequences for the cargo polypeptide fusion charged complementary peptide segments. In some embodiments, the DNA that can encode the cargo polypeptide fusion charged complementary peptide segments can be codon optimized for expression in a particular cell type, such as *E. coli*. Codon optimization techniques will be appreciated by those of skill in the art. The cargo polypeptide fusion charged complementary peptide segment encoding DNA can be included in a suitable expression vector. Suitable expression vectors will be appreciated by those of ordinary skill in the art. In some embodiments, the expression vector can also express genes that can result in more efficient and/or accurate protein folding and other post-translation modifications. Such expression vectors will be appreciated by those of ordinary skill in the art. The expression vectors can be introduced into a suitable cells and the polypeptides can be produced by expression in the cells and harvested using techniques generally known in the art.

For example a fusion peptide segment containing the cargo polypeptide, can be produced from a recombinant DNA construct containing DNA encoding the negative or positive peptide segment operatively coupled with DNA encoding the cargo polypeptide and any optional linker. The DNA encoding the negative or positive peptide segment can be operatively coupled to the cargo polypeptide and any optional linker such that the cargo polypeptide is translated in-frame with negative or positive peptide segment.

The cargo polypeptide can be a reporter protein (e.g. a fluorescent protein), a pharmaceutically relevant protein (a protein that can be effective to prevent or treat a disease or symptom thereof in a subject), a cell- or tissue-targeting protein, an antibody or fragment thereof, enzyme, growth factor, cytokine, chemokine, extracellular matrix protein or fragment thereof, structural protein or fragment thereof, a transmembrane protein or fragment thereof, a transcription factor or fragment thereof, and/or an antigen. The amino acid sequences and/or coding DNA sequences of the cargo polypeptides can be appreciated by those of skill in the art.

Co-Assembly Peptide Nanostructures

Generally, the charge complementary segments do not self-assemble until both the positive and the negative charge complementary segments are present together under stimulating conditions. In some embodiments, the stimulating conditions can be incubation and/or placement in a solutions (e.g. an aqueous solution) at about a neutral or near physiological pH. In some embodiments, the pH of the solution can range from about 6.5 to about 8.5. Once stimulated, the ionizable amino acids are ionized and the charge complementary segments self-assemble into beta sheets with alternating positive and negative segments. The charge complementary peptides (with and/or without a cargo polypeptide) can self-assemble into structures, such as nanofibrillar hydrogels, nanofibers, microparticles, or nanoparticles depending on the concentration of the complementary charged peptide segments with no cargo polypeptide and concentration of positive and negative co-assembly cargo polypeptide fused peptide segments present in the mixture prior to self-assembly.

The co-assembly peptides and resulting nanostructures can be used to endow other supramolecular materials with functional properties of the cargo polypeptides that can be coupled to the co-assembly peptides. The nanostructures can be optionally incorporated into other supermolecular biomaterials and compositions including, but not limited to, hydrogels, synthetic polymer matrices or network, natural polymer matrices or networks, composite networks of natural and synthetic polymers, polymer nanoparticles, and/or polymer microparticles.

Provided herein are supramolecular structures that can be composed of one or more positive peptides and one or more negative peptides that can be attached to each other via e.g. an electrostatic interactions. A positive peptide can include at least 3 amino acids ($A_1$-$A_3$ as set forth sequentially from C to N terminus), wherein $A_1$, $A_2$, and $A_3$ can each be independently selected from a positively charged amino acid and a hydrophobic amino acid, and wherein at least one amino acid of $A_1$-$A_3$ can be a positively charged amino acid and at least one amino acid of $A_1$-$A_3$ can be a hydrophobic amino acid. A negative peptide can include at least 3 amino acids ($B_1$-$B_3$ as set forth sequentially from C to N terminus), wherein $B_1$, $B_2$, and $B_3$ can each be independently selected from a negatively charged amino acid and a hydrophobic amino acid, and wherein at least one amino acid of $B_1$-$B_3$ can be a negatively charged amino acid and at least one amino acid of $B_1$-$B_3$ can be a hydrophobic amino acid. When one or more positive and one or more negative peptide segments are mixed together under stimulating conditions, they can self-assemble to form supramolecular structures. The 3 amino acids ($A_1$-$A_3$) can form a core of a larger peptide and can have additional amino acids at the N- and/or C-terminus of the 4 amino acid ($A_1$-$A_3$) core. The additional amino acids can range in number from 1, 2, 3, 4, 5, 6, 7, 8, 9, 10, 20, 30, 40, or 50 or more. The additional amino acids can each be selected from natural and unnatural amino acids, a cationic amino acid, an anionic amino acid, a hydrophobic amino acid, or a polar amino acid. In some embodiments the amino acids can be modified, such as iodinated, fluorinated, or otherwise labeled.

A positive peptide can include at least 4 amino acids ($A_1$-$A_4$ (SEQ ID NO: 44) as set forth sequentially from C to N terminus), wherein $A_1$, $A_2$, $A_3$, and $A_4$, can each be independently selected from a positively charged amino acid and a hydrophobic amino acid, and wherein at least one amino acid of $A_1$-$A_4$ (SEQ ID NO: 44) can be a positively charged amino acid and at least one amino acid of $A_1$-$A_4$ (SEQ ID NO: 44) can be a hydrophobic amino acid. A negative peptide can include at least 4 amino acids ($B_1$-$B_4$ (SEQ ID NO: 45) as set forth sequentially from C to N terminus), wherein $B_1$, $B_2$, $B_3$, and $B_4$ can each be independently selected from a negatively charged amino acid and a hydrophobic amino acid, and wherein at least one amino acid of $B_1$-$B_4$ (SEQ ID NO: 45) can be a negatively charged amino acid and at least one amino acid of $B_1$-$B_4$ (SEQ ID NO: 45) can be a hydrophobic amino acid. When one or more positive and one or more negative peptide segments are mixed together under stimulating conditions, they can self-assemble to form supramolecular structures. The 4 amino acids ($A_1$-$A_4$) (SEQ ID NO: 44) can form a core of a larger peptide and can have additional amino acids at the N- and/or C-terminus of the 4 amino acid ($A_1$-$A_4$) (SEQ ID NO: 44) core. The additional amino acids can range in number from 1, 2, 3, 4, 5, 6, 7, 8, 9, 10, 20, 30, 40, or 50 or more. The additional amino acids can each be selected from natural and unnatural amino acids, a cationic amino acid, an anionic amino acid, a hydrophobic amino acid, or a polar amino acid. In some embodiments the amino acids can be modified, such as iodinated, fluorinated, or otherwise labeled.

A positive peptide can include at least 5 amino acids ($A_1$-$A_5$ (SEQ ID NO: 46) as set forth sequentially from C to N terminus), wherein $A_1$, $A_2$, $A_3$, $A_4$, and $A_5$, can each be independently selected from a positively charged amino acid and a hydrophobic amino acid, and wherein at least one amino acid of $A_1$-$A_5$ (SEQ ID NO: 46) can be a positively charged amino acid and at least one amino acid of $A_1$-$A_5$ (SEQ ID NO: 46) can be a hydrophobic amino acid. A negative peptide can include at least 5 amino acids ($B_1$-$B_5$ (SEQ ID NO: 47) as set forth sequentially from C to N terminus), wherein $B_1$, $B_2$, $B_3$, $B_4$, and $B_5$ can each be independently selected from a negatively charged amino acid and a hydrophobic amino acid, and wherein at least one amino acid of $B_1$-$B_5$ (SEQ ID NO: 47) can be a negatively charged amino acid and at least one amino acid of $B_1$-$B_5$ (SEQ ID NO: 47) can be a hydrophobic amino acid. When one or more positive and one or more negative peptide segments are mixed together under stimulating conditions, they can self-assemble to form supramolecular structures. The 5 amino acids ($A_1$-$A_5$) (SEQ ID NO: 46) can form a core of a larger peptide and can have additional amino acids at the N- and/or C-terminus of the 5 amino acid ($A_1$-$A_5$) (SEQ ID NO: 46) core. The additional amino acids can range in number from 1, 2, 3, 4, 5, 6, 7, 8, 9, 10, 20, 30, 40, or 50 or more. The additional amino acids can each be selected from natural and unnatural amino acids, a cationic amino acid, an anionic amino acid, a hydrophobic amino acid, or a polar amino acid. In some embodiments the amino acids can be modified, such as iodinated, fluorinated, or otherwise labeled.

A positive peptide can include at least 7 amino acids ($A_1$-$A_7$ (SEQ ID NO: 48) as set forth sequentially from C to N terminus), wherein $A_1$, $A_2$, $A_3$, $A_4$, $A_5$, $A_6$, and $A_7$, can each be independently selected from a positively charged amino acid and a hydrophobic amino acid, and wherein at least one amino acid of $A_1$-$A_7$ (SEQ ID NO: 48) can be a positively charged amino acid and at least one amino acid of $A_1$-$A_7$ (SEQ ID NO: 48) can be a hydrophobic amino acid. A negative peptide can include at least 7 amino acids ($B_1$-$B_7$ (SEQ ID NO: 49) as set forth sequentially from C to N terminus), wherein $B_1$, $B_2$, $B_3$, $B_4$, $B_5$, $B_6$, and $B_7$ can each be independently selected from a negatively charged amino acid and a hydrophobic amino acid, and wherein at least one amino acid of $B_1$-$B_7$ (SEQ ID NO: 49) can be a negatively charged amino acid and at least one amino acid of $B_1$-$B_7$ (SEQ ID NO: 49) can be a hydrophobic amino acid. When one or more positive and one or more negative peptide segments are mixed together under stimulating conditions, they can self-assemble to form supramolecular structures. The 7 amino acids ($A_1$-$A_7$) (SEQ ID NO: 48) can form a core of a larger peptide and can have additional amino acids at the N- and/or C-terminus of the 5 amino acid ($A_1$-$A_7$) (SEQ ID NO: 48) core. The additional amino acids can range in number from 1, 2, 3, 4, 5, 6, 7, 8, 9, 10, 20, 30, 40, or 50 or more. The additional amino acids can each be selected from natural and unnatural amino acids, a cationic amino acid, an anionic amino acid, a hydrophobic amino acid, or a polar amino acid. In some embodiments the amino acids can be modified, such as iodinated, fluorinated, or otherwise labeled.

The positively charged amino acids (cationic amino acids) can each be independently selected from the group of lysine, histidine, and arginine. The negatively charged amino acids (anionic amino acids) can each be independently selected from the group of aspartate and glutamate. The hydrophobic amino acids can each be independently selected from the group consisting of: glycine, alanine, valine, leucine, methionine, isoleucine, phenylalanine, tyrosine, and tryptophan. In some embodiments, the positive and/or negative peptide segment can further include a cargo polypeptide coupled to the N and/or the C terminus of the peptide. Cargo polypeptides are discussed in greater detail elsewhere herein.

In some embodiments, the peptide having a net positive charge can have at least 11 amino acids ($A_1$-$A_{11}$ (SEQ ID NO: 50) as set forth sequentially from C to N terminus), wherein $A_1$, $A_9$, and $A_{11}$ can each be a polar or a cationic amino acid, wherein $A_2$ can be a polar amino acid, wherein $A_3$ can be a cationic or a polar amino acid, wherein $A_4$, $A_6$, and $A_8$ can each be a hydrophobic amino acid, wherein $A_5$ and $A_7$ can each be a cationic amino acid or a polar amino acid, and wherein $A_{10}$ can be a polar amino acid.

In some embodiments, the negative peptide can be composed at least 11 amino acids amino acids ($B_1$-$B_{11}$ (SEQ ID NO: 51) as set forth sequentially from C to N terminus), wherein $B_1$ and $B_{11}$ can each be a polar or an anionic amino acid, wherein $B_2$ and $B_{10}$, can each be polar amino acids, wherein $B_3$, $B_5$, $B_7$, and $B_9$, can each be an anionic or a polar amino acid, and wherein $B_4$, $B_6$, and $B_8$, can each be hydrophobic amino acids.

Suitable cationic amino acids can have positively charged side (or "R" groups) groups and can include, but are not limited to, lysine, arginine, and histidine. Suitable anionic amino acids can have negatively charged side groups and can include, but are not limited to, aspartate and glutamate. Suitable polar amino acids can have polar, uncharged side groups, and can include, but are not limited to, serine, threonine, cysteine, proline, asparagine, and glutamine. Suitable hydrophobic amino acids can have nonpolar, aliphatic or aromatic side groups and can include, but are not limited to, glycine, alanine, valine, leucine, methionine, isoleucine, phenylalanine, tyrosine, and tryptophan. All sequences resulting from employing the general scheme shown in FIGS. 2A and 2B and at least the amino acids described herein are enabled by and within the scope of this disclosure.

The positive peptides and negative peptides can be synthesized using de novo peptide synthesis techniques generally known in the art.

Figure 47:
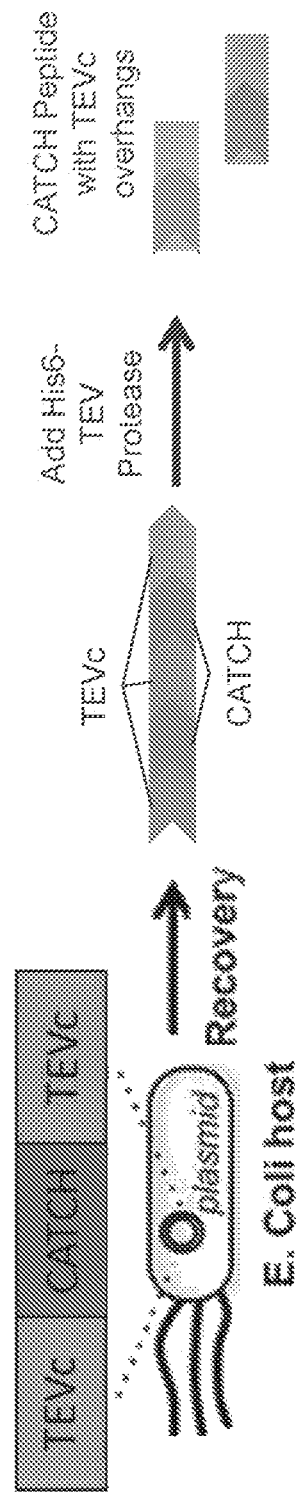
FIG. 47 shows a schematic demonstrating an embodiment of an expression system that can be used to produce CATCH peptides.

In other embodiments, the peptides can be produced via recombinant protein expression techniques based on expression of a peptide or protein sequence from a suitable expression vector. A cartoon of one embodiment of such an expression system is shown in FIG. 47. In some embodiments, the expression vector can include a segment of DNA that can encode a polypeptide that can include one or more positive or negative peptides described above. The segment of DNA can include DNA encoding a first positive or negative peptide that is operatively coupled to a second positive or negative peptide. A DNA segment encoding a protease cleavage site can be coupled in between the first and the second positive or negative peptide. This pattern of peptide encoding DNA segment and protease cleavage site encoding DNA can be repeated as many times as desired and that can be expressed from the expression vector. Stated differently, the DNA segment can encode a chain of one or more positive or negative peptides as described above spaced apart from the protease cleavage sequence. In some embodiments, the protease cleavage sequence can be attached directly at the N-terminus of each peptide or at the C terminus of each peptide After cleavage the peptides can have residual amino acids that correspond to the cleavage site. Table 1 shows, without limitation, various protease cleavage sites that can be included and the portion of the cleavage site would be residual on the N-terminus and C-terminus after cleavage with the protease. The polypeptide can be configured such that all the peptides produced after protease cleavage are the same. The polypeptide can be configured such that the peptides produced after protease cleavage contain a mixture of different positive and/or negative peptides.

TABLE 1

| Protease | Cleavage Sequence | N-terminal residue(s) | C-terminal residue(s) |
|---|---|---|---|
| Cyanogen Bromide | M | M | Any residue that is on the N-terminal side of the M prior to cleavage. |
| Thrombin | LVPR/G (SEQ ID NO: 12) | G | LVPR (SEQ ID NO: 13) |
| Human Rhinovrus 3C Protease | LEVLFQ/GP (SEQ ID NO: 14) | GP | LEVLFQ (SEQ ID NO: 15) |
| Factor Xa | IEGR/X (SEQ ID NO: 16) | X | IEGR (SEQ ID NO: 17) |
| Enterokinase | DDDDK/X (SEQ ID NO: 18) | X | DDDDK (SEQ ID NO: 19) |
| TEV | ENLFQ/S (SEQ ID NO: 20) | S | ENLFQ (SEQ ID NO: 21) |

*Where X is any amino acid

The DNA can further include one or more segments that each encode for a purification tag. Suitable purification tags are generally known in the art and can include, but are not limited to, FLAG, His tag, maltose binding protein, and glutathione-S-transferase. When the polypeptide is expressed from the vector, it can be recovered from the host production cell by any suitable method. After recovery, the produced polypeptide can be purified using a suitable purification technique, including but not limited to, affinity purification or other suitable separation technique (e.g. immunoseparation). After recovery and/or purification, the polypeptide can be exposed to a protease to cleave the polypeptide to release the individual peptide segments. The protease itself can contain an affinity purification tag such that the protease can be removed after cleaving the produced polypeptide via a suitable affinity purification technique, that can include affinity purification based on a protein tag and immunopurification techniques. In other embodiments, the protease can be made inactive by contacting the protease with a protease inhibitor.

In other embodiments a synthetic gene can be generated that encodes a larger carrier protein that is operatively coupled to a positive or negative peptide provided herein. The carrier protein and the positive or negative peptide can be separated by a protease cleavage site. As described above. The synthetic gene can be included in a suitable expression vector. After production of the polypeptide from the synthetic gene, the positive or negative peptide can be separated from the carrier protein by exposing the polypeptide to a protease capable of cleaving at the protease cleavage site in the polypeptide. Suitable carrier proteins can include, without limitation, any protein ranging from about 100 amino acids to about 600 amino acids in length such as, but not limited to, kerosteroid isomerase, maltose binding protein, and glutathione S-transferase.

As such, also provided herein are DNA segments that can encode a positive and/or negative peptide described herein. One of ordinary skill in the art, based upon a peptide or polypeptide sequence, will be able to construct suitable coding sequences for the peptides and polypeptides described herein. Also provided herein are DNA vectors that can include one or more DNA segments that can encode one or more positive and/or negative peptides described herein. The DNA segment that can encode one or more positive and/or negative peptides described herein can be operatively coupled to a suitable promoter that can drive expression of the peptide or polypeptide that is encoded by the DNA segment.

The positive and negative peptides (with or without cargo molecules) and/or vectors that can be used to produce them can be provided as a kit. The kits can contain the positive and negative peptides separate from one another in appropriate containers. The peptides can be solubilized in a carrier solution, lyophilized, or otherwise provided. The kits can also include other reagents such as a solution at a pH ranging from 6.5 to about 8.5. The solution can be used to supply the stimulating condition upon which the positive and negative peptides can self-assemble.

Uses of the Co-Assembly Peptides and Nanostructures

The co-assembly peptides and resulting nanostructures can be used to endow other supramolecular materials with functional properties of the cargo polypeptides that can be coupled to the co-assembly peptides. As discussed above, depending on the concentration of the co-assembly tag peptides mixed and stimulated, different nanostructures can be formed. In embodiments, a method of using the co-assembly peptides provided herein can include the step of mixing at least one engineered peptide having a net positive charge with at least one engineered peptide having a net negative charge in an aqueous solution having a pH ranging from about 6.5 to about 8.5. The mixture can be a mixture containing one or more types of positive peptide (s) and one or more types of negative peptide(s). It will be appreciated that multiple types of positive and negative peptides can be mixed together, where the "type" refers to the cargo molecule attached (none or one present). To put this in context and as a non-limiting example, three types of negative peptides can be a negative peptide having no cargo polypeptide (a first type), a negative peptide having a first cargo polypeptide (a second type), and a negative peptide having a second cargo polypeptide (a third type), where the first cargo polypeptide and the second cargo polypeptide are not the same polypeptide. The number of types of peptides that can be present in a mixture can be at least greater than 2. In some embodiments, the number of types of peptides that can be present in a mixture can range from 2 to 50 or more.

The concentration of any charge complementary peptide in any mixture can range from about 1 0.1 nM to about 1000 mM or more. In some binary mixtures (e.g. mixtures containing one type of positive peptide and one type of negative peptide), the concentration of the positive peptide can be equal to the concentration of the negative peptide. In other binary mixtures, the concentration of the positive peptide can be greater than the concentration of the negative peptide. In further binary mixtures, the concentration of the positive peptide can be less that the concentration of the negative peptide. In some tertiary mixtures (e.g. mixtures containing 3 different types of peptides but at least one type of positive peptide and at least one type of negative peptide), the concentration of each type of peptide can be equal or at least one or at least two types of peptides can be present a concentration that is greater or less than the third type or peptide. In a ternary mixture (e.g. mixtures containing 4 different types of peptides but at least one type of positive peptide and at least one type of negative peptide), the concentrations of each peptide type can be equal or 1, 2, or 3 peptide types can be present at a concentration greater than or less than that of the fourth peptide type present. In view of this description, it will be appreciated how the concentration of the multiple different types of peptides can be varied no matter what the number of types of peptides used.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Self-assembly is the spontaneous organization of molecules into a precise supramolecular architecture without any external guidance.[49] Throughout nature, biomolecule self-assembly gives rise to various functional biomaterials that can perform complex tasks, such as molecular sensing and recognition, chemical synthesis, motility, and compartmentalization, as well as multi-scale hierarchical organization.[34] There is increasing interest in biomolecule self-assembly for bottom-up fabrication of biomaterials for medical and technological applications.[48] Among the various synthetic biomolecules capable of self-assembly,[11] peptides and peptide analogs that form elongated nanofibers by adopting β-sheet secondary structures provide numerous advantages for creating supramolecular biomaterials. In particular, β-sheet fibrillizing peptides can be synthesized and purified in high yield using conventional methods. Peptide self-assembly into β-sheet nanofibers occurs under mild aqueous conditions, with the resultant nanofibers often undergoing sol-gel transition into macroscopic, physically-crosslinked hydrated structures (i.e. "hydrogels") above a critical concentration.[20] The amino acid sequence of β-sheet fibrillizing peptides can be systematically modified to tailor nanofiber morphology, gelation properties, and stimuli-responsiveness according to the intended application.[4] In addition, β-sheet peptide nanofibers can be fabricated into micron-sized gels using various conventional polymer-processing techniques.[12, 46] Finally, β-sheet peptide nanofibers are well-suited for use in biomedical applications because they are composed of natural amino acids that can be metabolized, they are often biocompatible with cells and tissues, and they typically elicit minimal inflammation and weak or no adaptive immunity directed against the peptide itself, despite being foreign to the host.[5, 10, 14, 15, 17, 18, 22]

To be useful for medical or technological applications, supramolecular biomaterials must often demonstrate functional capabilities beyond robust self-assembly and biocompability. Since synthetic peptides designed to self-assemble typically lack any additional functional features, ligands, fluorophores, antigens, drugs, or other bioactive compounds are often installed into supramolecular biomaterials to impart functional capabilities. Supramolecular biomaterials can be functionalized post-assembly via various covalent and non-covalent grafting approaches,[13, 23, 29, 31, 32, 35, 38, 42-44] However, the former often rely on complex, inefficient, or poorly reproducible reactions, while the latter may only provide transient functionality within complex biological environments.

Alternatively, functional capabilities can be installed directly into supramolecular biomaterials via covalent fusion of a functional molecule and a self-assembling peptide in the pre-assembled state (i.e. "fusion peptides"), which provides many advantages over post-assembly modification. In particular, diverse libraries of fusion peptides modified with functional molecules that are stable in organic solvents (e.g. peptides, sugars, or small organic compounds) can be prepared in high yield and purity by adapting conventional solid-phase peptide synthesis methods.[20, 30, 39] The conditions that promote self-assembly of fusion peptides are often similar to those of the unmodified peptide. The concentration of functional molecule integrated into single-component supramolecular assemblies via fusion peptides is well defined and highly reproducible, yet multi-component supramolecular biomaterials with modular and tunable functional capabilities can also be fabricated via simple mixing of two or more fusion peptide variants in the pre-assembled state.[21] Finally, functional molecules fused to a self-assembling peptide are often stably integrated into supramolecular biomaterials because dissociation of peptides inserted into β-sheet nanofibers is energetically unfavorable.[19] As a result, fusion peptides have led to a broad assortment of supramolecular biomaterials with functional capabilities that are suitable for use in various biomedical and biotechnological applications, such as promoting cell adhesion for tissue engineering and regenerative medicine,[8, 30] enabling controlled-release of therapeutics,[6, 9, 12, 26, 27, 45] and presenting antigens and immunomodulatory signals to elicit robust adaptive immunity.[3, 37, 41]

Installing functional molecules with more sophisticated properties, such as catalysis, selective molecular recognition, tunable visible light fluorescence, or precise antigen conformation, could impart unprecedented functional capabilities into supramolecular biomaterials already finding use in biomedical and biotechnological applications. Owing to the diversity of specialized functional capabilities afforded by folded proteins when compared to unfolded peptides and small molecules, there is growing interest in installing folded proteins into supramolecular biomaterials. Covalent fusions of folded proteins and self-assembling peptides provide many advantages over covalent grafting from a material fabrication perspective, yet there are many challenges inherent to covalent fusions from a synthesis perspective. In particular, conventional peptide synthesis and purification cannot be adapted to produce protein-peptide fusions. Instead, fusion proteins are typically expressed from recombinant DNA using translational machinery housed within microbes or other cellular hosts. The environment within the cytoplasm of expression hosts is often favorable for β-sheet peptide self-assembly, however, which can hinder recovery of soluble, bioactive fusion proteins by inducing aggregation or misfolding.[24, 50] Self-assembly domains with slow fibrillization kinetics or pH-responsive assembly can address this limitation,[1, 2, 19, 28, 33] however the former requires assembly kinetics that are well-behaved under various expression conditions and with a wide variety of fusion protein partners, while the latter necessitates proteins with folded conformations that are not pH-sensitive. An under-explored alternative is a peptide that is designed to resist assembly until acted upon by a stimulus that can be applied under neutral, near-physiological conditions that are ideal for maintaining protein folding and function.

Figure 8:
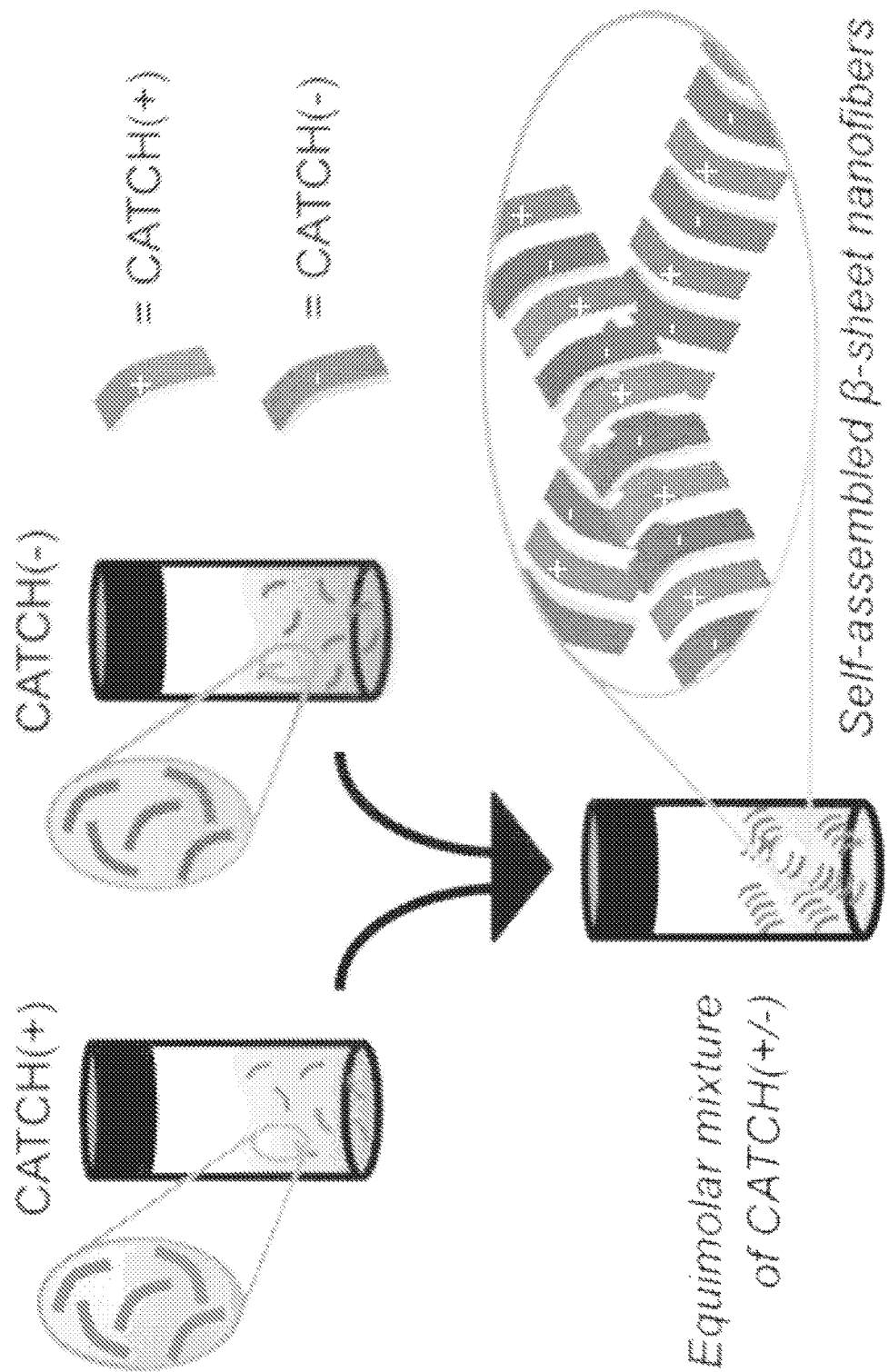
FIG. 8 shows a schematic representation of CATCH peptide co-assembly upon mixing.

In this Example, an approach to install a folded protein that can only assemble into β-sheet nanofibers at neutral pH in the presence of a second charge-complementary peptide (FIGS. 6-9). Also referred to as "CATCH", for Co-Assembly Tags based on CHarge complementarity), Ac-QQKFKFKFKQQ-Am [CATCH(+)] (SEQ ID NO: 1) and Ac-EQEFEFEFEQE-Am [CATCH(-)] (SEQ ID NO: 2) are cationic and anionic variants of the synthetic zwitterionic β-sheet fibrillizing peptide, Ac-QQKFQFQFEQQ-Am (SEQ ID NO: 41) (Q11) (FIGS. 6 and 7A-7B).[7] The alternating core of hydrophobic and hydrophilic residues within Q11 is a common feature of peptides that self-assemble into β-sheet nanofibers,[4] and was maintained in CATCH peptide design. Here, various polar residues within Q11 were replaced with ionizable residues to render CATCH peptide assembly energetically unfavorable until the two peptides were combined in solution (FIG. 8).

Figure 9:
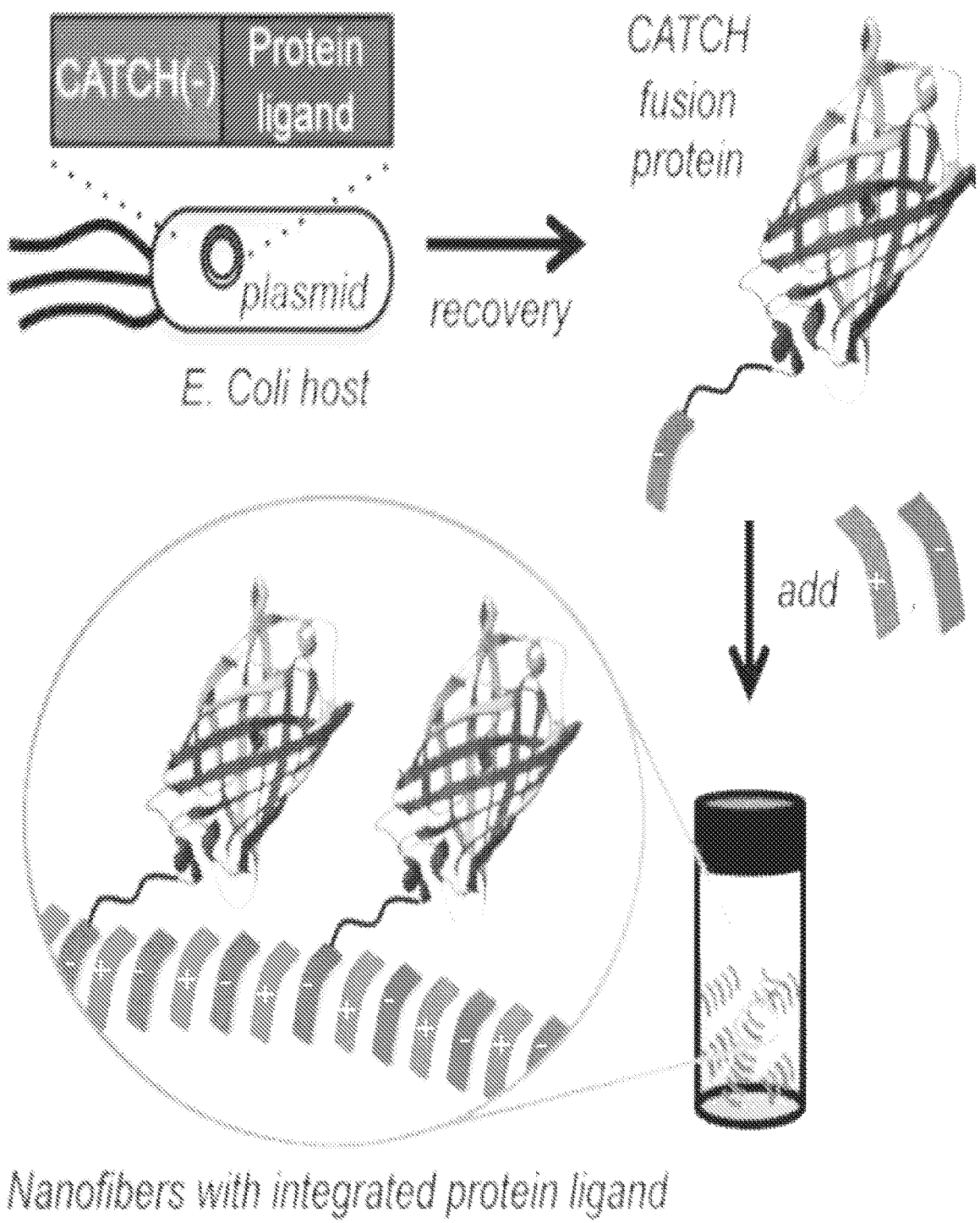
FIG. 9 shows a schematic of a functional protein ligand integrated into nanofibers via the CATCH fusion tag system (protein adapted from PDB: 1EMA).
Figure 10A:
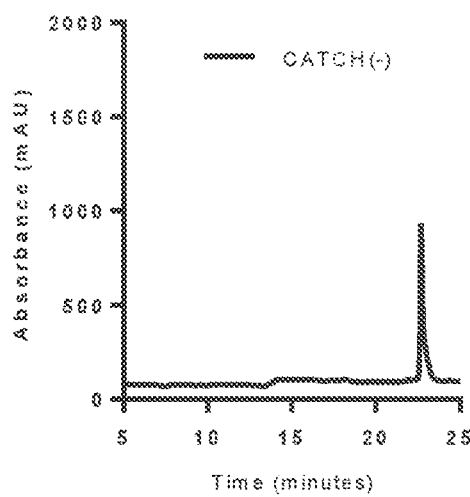
FIGS. 10A-10D show graphs demonstrating the purified CATCH(−) (FIG. 10A), CATCH (+) (FIG. 10B), mCATCH (−) (FIG. 10C), and mCATCH(+) (FIG. 10D) after HPLC.
Figure 10B:
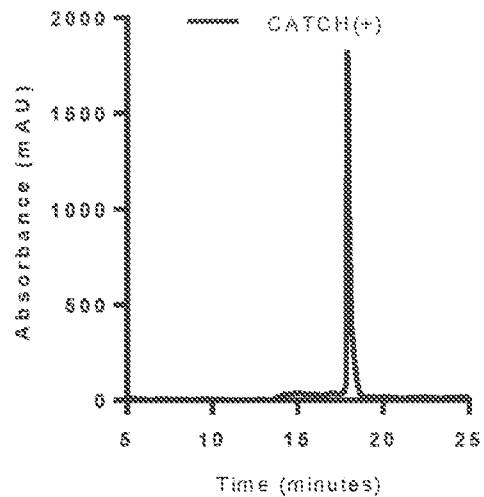
Figure 10C:
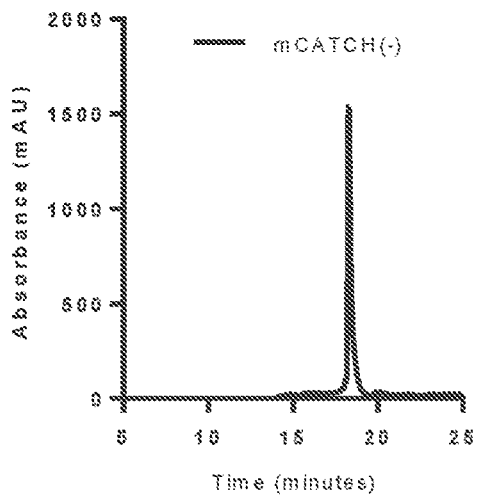
Figure 10D:
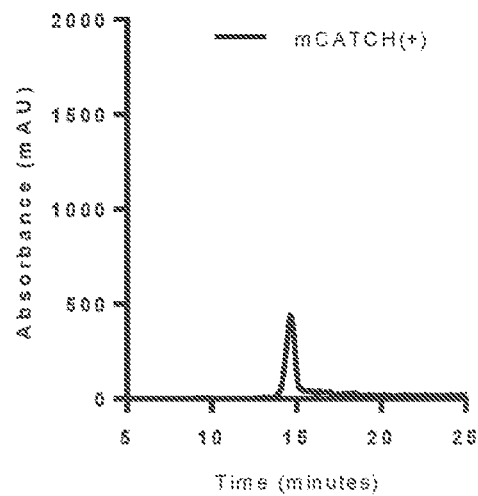
Figure 11A:
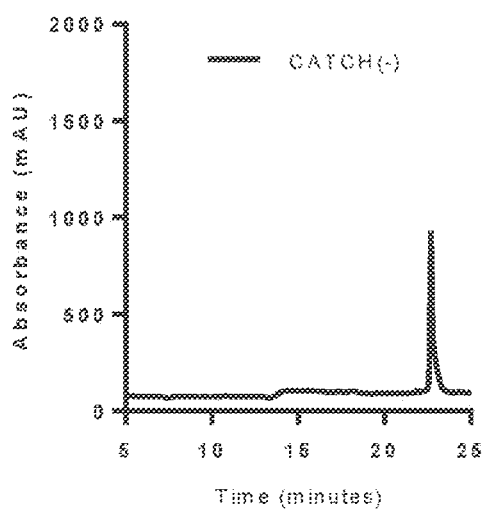
FIGS. 11A-11D show results from MALDI-TOF mass spectrometry analysis of CATCH(−) (FIG. 11A), CATCH (+) (FIG. 11B), mCATCH(−) (FIG. 11C), and mCATCH(+) (FIG. 11D)
Figure 11B:
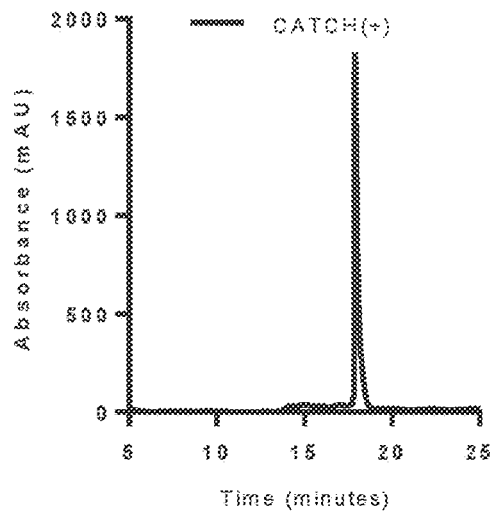
Figure 11C:
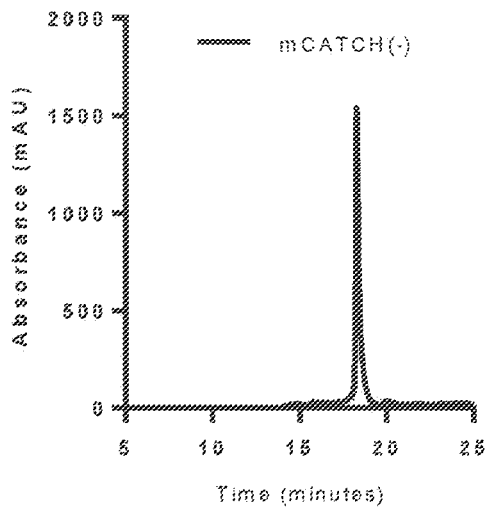
Figure 11D:
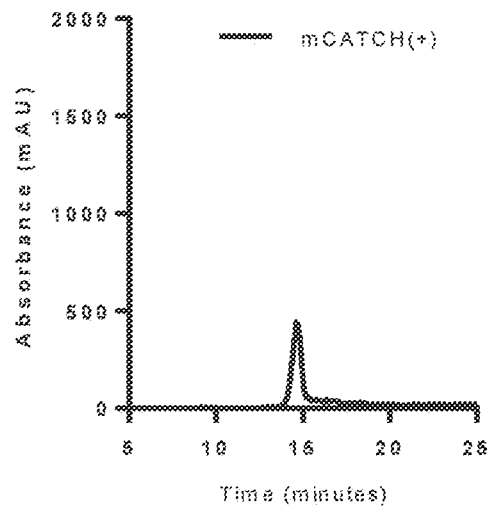

Electrostatic control of assembly is expected to enable optimal E. coli expression of a soluble, monomeric fusion of CATCH(-) and a folded protein by reducing the propensity for fusion protein aggregation or misfolding due to premature peptide self-assembly. In turn, the CATCH fusion protein can integrate into supramolecular biomaterials upon addition of excess CATCH(+) and CATCH(-) (FIG. 9). The β-sheet fibrillization properties of CATCH(+) and CATCH(-) at neutral pH, the expression of a fluorescent CATCH(-) fusion protein by E. coli, and the co-assembly of this fusion protein with CATCH peptides under various conditions were characterized. Finally, the physical crosslinking of CATCH nanofibers into hydrogels was characterized to fabricate functional supramolecular biomaterials with an integrated folded protein.

Materials and Methods

Peptide Synthesis and Purification. The two complimentary peptides, Ac-EQEFEFEFEQE-Am [CATCH(-)] (SEQ ID NO: 2) and Ac-QQKFKFKFKQQ-Am [CATCH(+)] (SEQ ID NO: 1), and their respective mutants, Ac-EQEPEPEPEQE-Am [mCATCH(-)] (SEQ ID NO: 22) and Ac-QQKPKPKPKQQ-Am [mCATCH(+)] (SEQ ID NO: 23), were synthesized using standard Fmoc solid-phase peptide synthesis on a CS336X automated peptide synthesizer (CS Bio), according to established methods.[12] All reagents for peptide synthesis were purchased from Novabiochem, unless stated otherwise. Following final Fmoc deprotection, peptides were acetylated at their N-termini with acetic anhydride (Sigma) (10% acetic anhydride (Sigma), 80% dimethylformamide (DMF) (Fisher), and 10% N,N-Diisopropylethylamine (DIEA) (Fisher)). Synthesis resin was collected, washed with acetone (Fisher), and dried in vacuo overnight. Peptides were cleaved and deprotected with a cocktail of 9.5:0.25:0.25 trifluoroacetic acid (TFA) (Fisher): triisopropylsilane (TIS) (Sigma):water. Peptides were then precipitated with cold diethyl ether (Fisher), collected via centrifugation, washed, and dried in vacuo overnight. Peptides were dissolved in water, frozen, and freeze-dried with a FreeZone 1 lyophilizer (Labconco).

Peptides were purified to greater than 90% purity by reverse phase high-performance liquid chromatography (RP-HPLC) using a Dionex™ Ultimate 3000TM System (Thermo Scientific) equipped with a C-18 column (Thermo Scientific) (FIGS. 10A-10D). The mobile phase consisted of (A) water and (B) acetonitrile, both containing 0.1% TFA. Peptides were detected by absorbance at 215 nm.

MALDI-Time-of-Flight Mass Spectrometry (MALDI-TOF-MS). For MALDI-TOF-MS analysis (FIGS. 11A-11D), 2 μL of RP-HPLC purified peptide was mixed with 2 μL of α-cyano-4-hydroxycinnamic acid (Sigma) (10 mg/mL) in 70% acetonitrile and 30% water (both containing 0.1% TFA). 2 μL of the mixed solution was spotted and dried onto a MSP 96-target polished steel BC MALDI plate. Samples were analyzed using reflectron, positive ion mode on an AB SCIEX TOF/TOFTM 5800 (Bruker) equipped with a 1 kHz N2 Opti-BeamTM on-axis laser.

Thioflavin T (ThT) Assay. A ThT stock solution containing 0.8 mg/ml of thioflavin T (Acros) in 1× phosphate-buffered saline (PBS) (137 mM NaCl, 2.7 mM KCl, 10 mM $Na_2HPO_4$ and 1.8 mM $KH_2PO_4$, pH 7.4) was filtered through a 0.22 μm syringe filter (Millex), and further diluted 1:10 with 1× PBS to create a working solution. Peptide samples were mixed with the ThT working solution at a 1:10 (v/v) ratio, added to a black 96-well plate (Corning), and analyzed with a Molecular Devices SpectraMax M3 spectrophotometer (excitation 450, emission 482 nm). All samples were run in triplicate, with the mean and standard deviation of these samples reported.

Circular Dichroism. Circular Dichroism was performed on an AVIV 202 spectrometer. Peptides were prepared in 1× PBS at 500 μM, unless stated otherwise. Samples were run 3 times, averaged, and converted to mean residue ellipticity. All data reported was for dynode values <500 V.

Expression and Purification of Peptide Fusion Proteins. DNA encoding fusion proteins consisting of each CATCH peptide or mutant CATCH peptide linked to superfolder GFP by a serine-glycine linker was inserted into a pET-21d vector between the NcoI site and XhoI site (FIGS. 12-13). Recombinant plasmids were then transformed into One Shot TOP10 Chemically Competent *E. coli* (Thermo) and plated on ampicillin (100 μg/mL) LB/agar plates for 18 hours at 37° C. Isolated colonies from the plates were selected and cultured in 5 mL of LB media with 0.1 mg/mL ampicillin overnight in an orbital shaker at 225 RPM and 37° C. for 18 hours. Plasmid DNA was recovered with the Qiagen Plasmid Miniprep Kit, and sequenced using the Sanger method at the University of Florida Interdisciplinary Center for Biotechnology Research. Positive DNA sequences were then transformed into Origami B (DE3) Competent Cells (Novagen) and plated on ampicillin (0.1 mg/mL) and kanamycin (0.05 mg/mL) LB/agar plates for 18 hours at 37° C.

Origami B (DE3) clones harboring plasmids encoding CATCH fusion proteins were grown overnight in 5 mL of 2xTY protein expression media (16 g tryptone, 10 g yeast, 5 g NaCl) with 0.1 mg/mL ampicillin and 0.05 mg/mL kanamycin in an orbital shaker at 225 rpm and 37° C. Origami B (DE3) cultures were then sub-cultured into 1L 2xTY media with 0.1 mg/mL ampicillin and 0.05 mg/mL kanamycin, and maintained in an orbital shaker at 225 RPM and 37° C. until an OD (A=600 nm) of 0.6-0.8 was reached. At the specified OD, 1 mL of 0.5 mM isopropyl β-D-1-thiogalactopyranoside (IPTG) was added into the media, and cultures were maintained in an orbital shaker at 225 RPM at 18° C. for 18 hours. Bacteria were pelleted by centrifugation (24600× g at 4° C. for 10 minutes) and re-suspended/washed in 1× PBS three times. Bacteria were then lysed by the addition of 4 mL of B-PER (Thermo) per gram of bacteria pellet. 2 μL of DNAse (2500 U/mL) and 2 μL lysozyme (50 mg/mL) were added for each 1 mL of B-PER added. 1 Pierce protease inhibitor tablet (Thermo) was added to the lysis cocktail. The bacteria pellet was manually separated using a metal spatula, and then incubated at room temperature on a rocker for 20 minutes. Lysate was centrifuged at 47700×g for 15 minutes at 4° C. to remove insoluble material, and the supernatant was collected by decanting. Fusion proteins were purified using metal-affinity chromatography with His-Pur cobalt resin (Thermo) and elution with a step-gradient of 5-250 mM imidazole in 1× PBS, similar to established methods.[19] Molecular weight of all fusion proteins was verified with SDS-PAGE.

Protein Fluorimetry. Fluorescence spectra of both CATCH(−)GFP and mCATCH(−)GFP were acquired with a Molecular Devices SpectraMax M3 spectrophotometer. 10 μM CATCH(−) GFP or mCATCH(−)GFP in 1× PBS was excited with 485 nm light (cutoff=495 nm) and emission was recorded over the range of 495-600 nm. Black 96-well clear bottom plates (Corning) were used to minimize background fluorescence. Spectra were collected in triplicate, with the average reported.

Size Exclusion Chromatography. Aggregation of CATCH (−)GFP and mCATCH(−)GFP was analyzed using size exclusion chromatography on an AKTA Pure fast protein liquid chromatography system equipped with a GE Healthcare Superdex 200 Increase 10/300 column. 200 μL of 10 μM CATCH(−)GFP or mCATCH(−)GFP in 1× PBS was injected into the sample loop. The sample loop was subsequently cleared with 5 mL of 1× PBS to ensure the entire sample was loaded onto the column, and then proteins were eluted with 2.0 column volumes of 1× PBS. Proteins were detected by absorbance at 280 nm.

Nanofiber preparation. Stock solutions of CATCH(−) and CATCH(+) were prepared by dissolving lyophilized peptides in 1× PBS to a final concentration of 500 μM. Peptide concentration was confirmed using Phe absorbance (A=260 nm). CATCH peptides were then mixed at a 1:1 (v/v) ratio and incubated overnight for formation of nanofibers, unless stated otherwise.

Nanofibers with integrated fusion proteins were prepared by mixing stock solutions of CATCH(−)GFP, CATCH(−), and CATCH(+) at final concentrations of 0.75 μM, 187.5 μM, and 200 HM, respectively, unless stated otherwise. Although not explicitly studied, we expected that CATCH (+) and CATCH(−) would co-assemble most efficiently at a nearly equimolar ratio. Thus, here a slight molar excess of CATCH(+) relative to total CATCH(−) (i.e. [CATCH(−) peptide]+[CATCH(−)GFP]) was expected to maximize CATCH(−)GFP integration into nanofibers by preventing competition between CATCH(−) and CATCH(−)GFP during co-assembly.

Transmission Electron Microscopy. Formvar-carbon coated 400 mesh copper grids (FCF400-CU-UB, EMS) were floated on top of 20 μL of 1× PBS solutions containing CATCH peptides with or without CATCH(−)GFP, and then dried by tilting the grid on a Kimwipe. Samples were negatively stained with 2% uranyl acetate in water, and analyzed using a Hitachi H-7000.

Fluorescence Microscopy. Microscopic morphology of CATCH peptide or peptide-fusion protein mixtures was investigated with a Zeiss Axio Observer inverted epifluorescent microscope. For samples containing only CATCH peptides, ThT was mixed with samples at a 1:1 (v/v) ratio, 5 μL of each sample was placed onto a glass microscope slide, samples were covered with a cover slip, and samples were viewed using a GFP filter set. For samples containing CATCH peptides and CATCH(−)GFP, 0.75 μM CATCH(−) GFP was mixed with 200 μM CATCH(+) and 187.5 μM CATCH(−), unless otherwise specified. 5 μL of each sample was placed onto a glass microscope slide, samples were covered with a cover slip, and samples were viewed using a GFP filter set. For all samples, images were collected using an exposure time of 4 s.

Particle Analysis. Size distribution of microscopic materials formed in solutions of 0.75 µM CATCH(−)GFP and 200 µM CATCH(+) under various conditions was determined from fluorescent photomicrographs using the Analyze Particle function in ImageJ software (NIH). Particle range was set from 2 to infinity for all samples, and 8-bit images were set with threshold values below 0.36% to minimize the halo around large particles, yet allow for small particles to be detected. Commercially-available fluorescent polymeric microspheres with known diameters of 1, 2, 4, and 9.9 µm were used for calibration of image analysis, as supplied by the manufacturer (Life Technologies). A minimum of 140 particles was analyzed per condition.

Dynamic light scattering (DLS) was measured on a Brookhaven 90Plus Particle Size Analyzer (Brookhaven Instruments Inc., NY) with BIC Particle Sizing Software. 0.75 µM CATCH(−) GFP+200 µM CATCH(+) samples were prepared in 1× PBS and either incubated for about 15 hours without mixing (i.e. "static") or stirred for 10 and 60 minutes. All samples were run 10 times for a period of about 30 seconds. Particle size histograms are reported in terms of intensity (%).

Zeta Potential. Zeta potential was analyzed on a Brookhaven Zeta Potential Analyzer (Brookhaven Instruments Inc., NY) with PALS Zeta Potential Analyzer Software. Measurements were obtained from samples of 1× PBS solutions containing 0.75 µM CATCH(−)GFP+200 UM CATCH(+) stirred for 1 hour. The sample was analyzed 10 times and only readings below 0.02 relative residual were used to calculate mean zeta potential.

Macroscopic Hydrogel Formation. A 12 mM stock solution of CATCH(−) was prepared by dissolving dry peptide in 1× PBS and adjusting the pH to ~7.6 with ammonium bicarbonate (Fisher). A 12 mM stock solution of CATCH(+) was prepared by dissolving dry peptide in 1×PBS and adjusting the pH to ~7.2 with hydrochloric acid (0.5 N Fisher). CATCH peptide stock solutions were combined at a 1:1 (v/v) ratio in a 0.2 mL glass vial (Thermo), and the vial was gently swirled for 2 min until the hydrogel formed. The hydrogel was stained with red food coloring to aid visualization. Hydrogel images were recorded using a digital still camera.

Protein Incorporation into Macroscopic Hydrogels. Hydrogels were prepared as described above, except 1.5 µM CATCH(−)GFP or mCATCH(−)GFP was added to the 12 mM CATCH(−) solution. Immediately after hydrogel formation, fluorescence was visualized by placing the glass vials on a SafeImager 2.0 transilluminator (Invitrogen) and recording images with a digital still camera. 800 µL of PBS was then carefully overlaid on top of hydrogel. The samples were then incubated for 48 hours to evaluate the protein incorporation within the hydrogel. At various time points, fluorescence in the buffer supernatant was visualized by placing the glass vials on a SafeImager 2.0 transilluminator (Invitrogen) and recording images with a digital still camera. At the end-point, buffer supernatant was carefully removed by decanting and fluorescence was visualized by placing the glass vials on a SafeImager 2.0 transilluminator (Invitrogen) and recording images with a digital still camera.

Results

Figure 14:
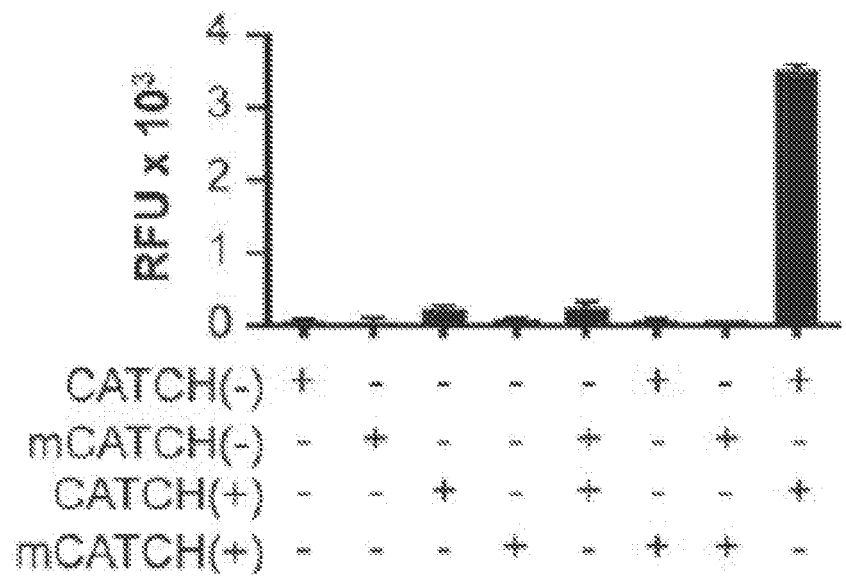
FIG. 14 shows a graph demonstrating results of an endpoint analysis of ThT fluorescence in solutions containing CATCH and mCATCH peptides in various combinations.
Figure 15:
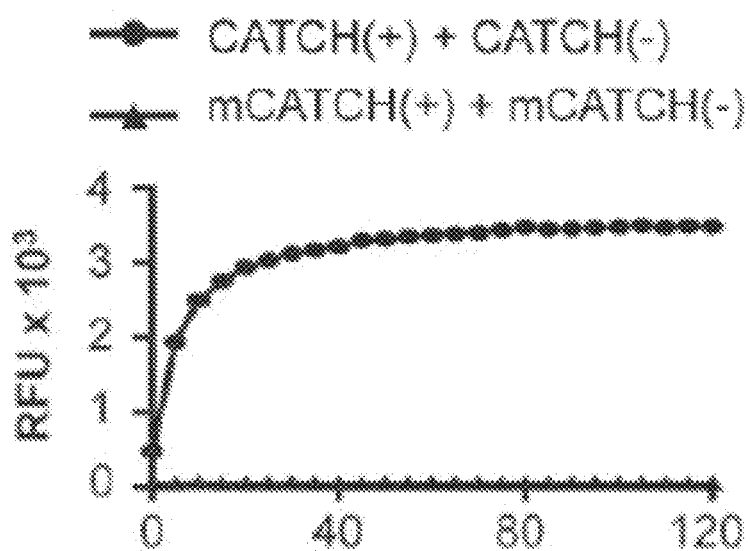
FIG. 15 shows a graph demonstrating results of a kinetic analysis of ThT fluorescence in solutions containing equimolar mixtures of CATCH peptides or mCATCH peptides.

CATCH peptide co-assembly into β-sheet nanofibers. First, CATCH(+) and CATCH(−) co-assembly was characterized using ThT fluorimetry, transmission electron microscopy (TEM), circular dichroism (CD), and fluorescence microscopy (FIGS. 14, 15, 16, 17, 18, 19, 20, 21, and 22). Thioflavin T (ThT) is a fluorescent dye that demonstrates a red-shift and increase in emission upon binding to β-sheet nanofibers.[47] ThT fluorescence increased significantly in an equimolar mixture of CATCH(−) and CATCH(+) when compared to solutions containing either peptide alone (FIG. 14). Notably, ThT fluorescence was not increased in equimolar mixtures of either CATCH peptide with its charge-complementary "mCATCH" mutant having proline residues in place of phenylalanine residues to disrupt β-sheet fibrillization (FIG. 14).[40] ThT fluorescence increased rapidly upon mixing CATCH(+) and CATCH(−) at an equimolar ratio, reaching a plateau within about 40 min that was persistent for at least 2 h, while no change in ThT fluorescence was observed for an equimolar mixture of mCATCH (+) and mCATCH(−) (FIG. 15).

Figure 16:
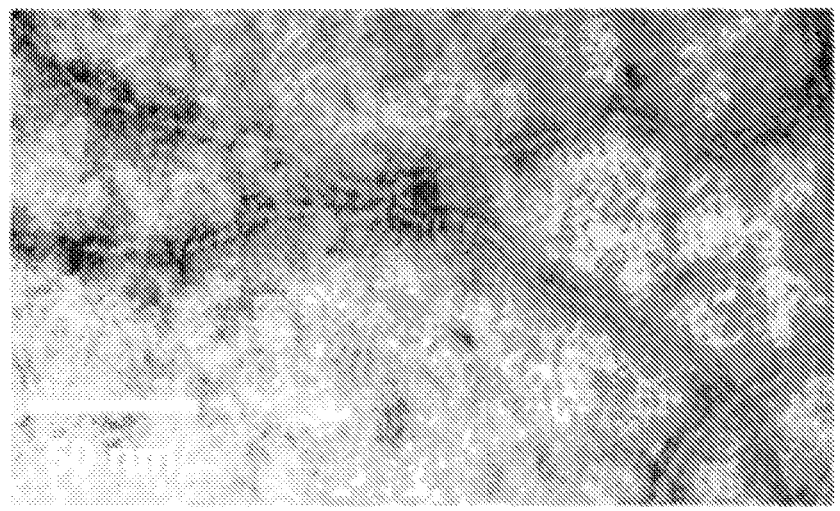
FIG. 16 shows a transmission electron micrograph of an equimolar mixture of CATCH peptides.
Figure 17:
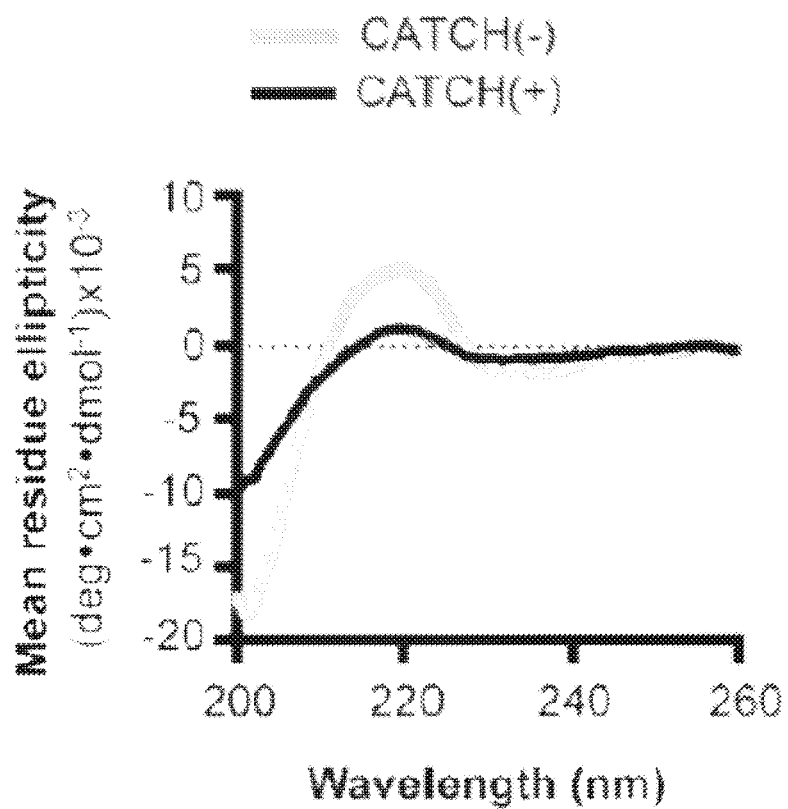
FIG. 17 shows a CD spectra of CATCH peptides alone.
Figure 18:
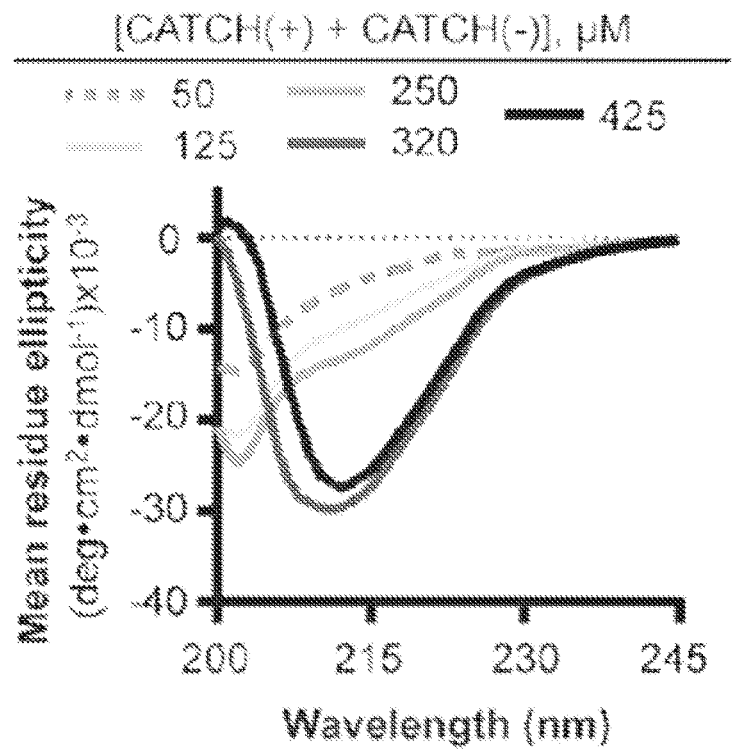
FIG. 18 shows a CD spectra of equimolar mixtures of CATCH peptides at different concentrations.
Figure 19:
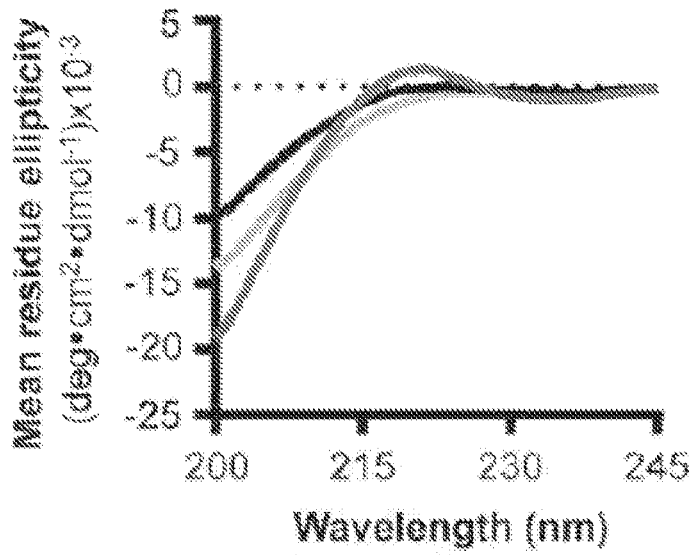
FIG. 19 shows a CD spectra of mixtures of CATCH and mCATCH peptides.
Figure 23:
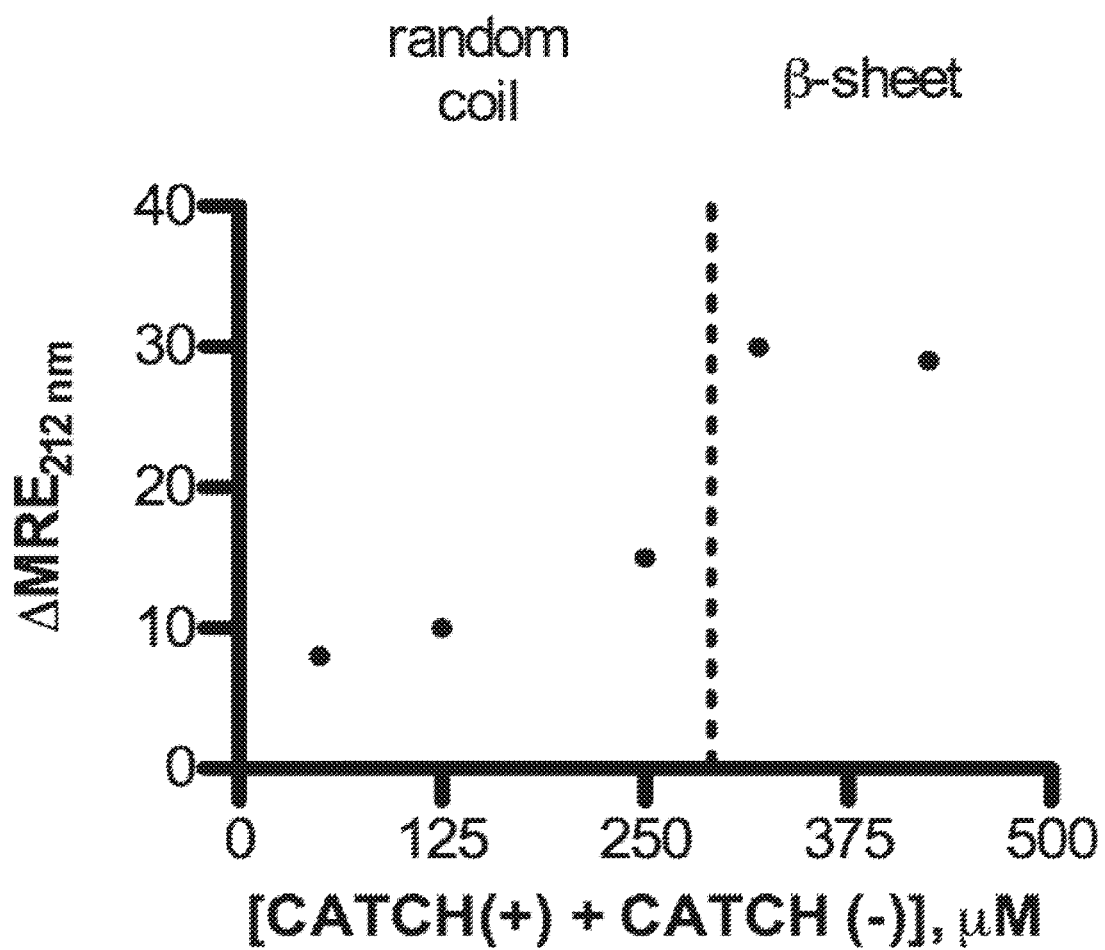
FIG. 23 shows a graph that can demonstrate a CATCH peptide β-sheet fibrillization concentration of about 300 uM.

Elongated structures having widths of about 5 nm and spanning hundreds of nm in length were observed in transmission electron micrographs of solutions containing an equimolar mixture of CATCH peptides (FIG. 16). In contrast, no discernible structures were observed in samples containing either CATCH peptide alone (data not shown). Consistent with this, CATCH(+) and CATCH(−) adopted predominantly random coil secondary structures when incubated alone, as demonstrated by circular dichroism maxima at 220 nm and minima at 200 nm (FIG. 17). CATCH peptides in an equimolar mixture also adopted a primarily random coil secondary structure at a concentration of 50 UM (FIG. 18, red). However, as the CATCH peptide concentration increased from 125-425 µM, the ellipticity at 200 nm approached zero and a new minimum emerged at 212 nm, which suggested that CATCH peptides underwent a concentration-dependent transition from a random coil to β-sheet secondary structure (FIG. 18, grayscale). In particular, the significant change in ellipticity at 212 nm between CATCH peptide concentrations of 250 and 320 µM, combined with similar ellipticity at 212 nm for peptide concentrations of 320 and 425 µM, suggested a CATCH peptide β-sheet fibrillization concentration of about 300 µM (FIG. 23). In contrast, mixtures of mCATCH and CATCH peptides adopted primarily random-coil secondary structures (FIG. 19), suggesting that the phenylalanine residues within the core of CATCH peptides were necessary for assembly into β-sheet structures.

Figure 20:
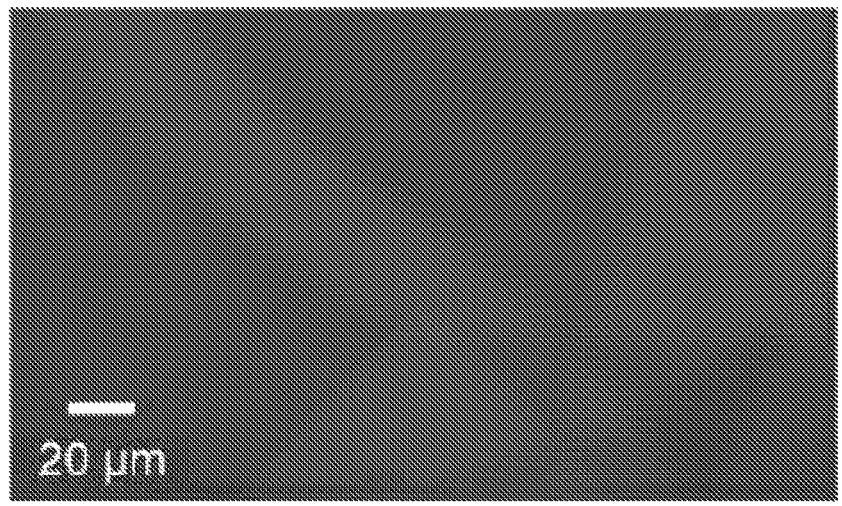
FIG. 20 shows a fluorescent photomicrograph of solutions containing ThT and CATCH(−).
Figure 21:
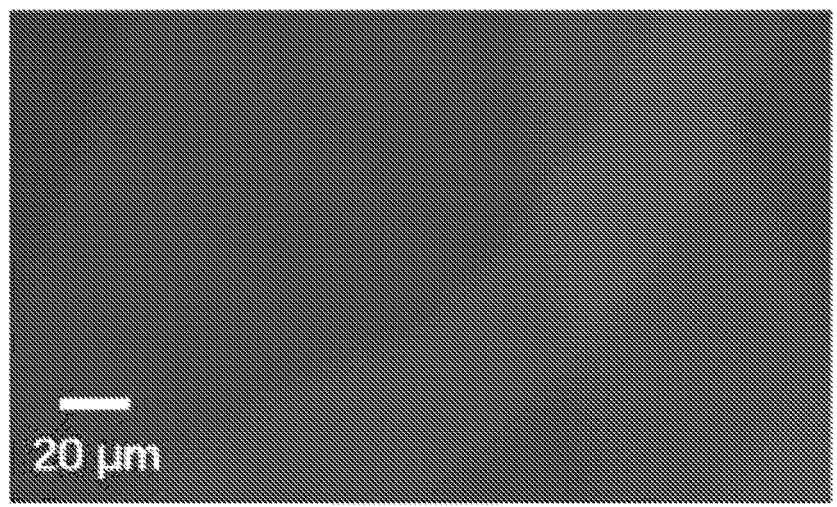
FIG. 21 shows a fluorescent photomicrograph of solutions containing ThT and CATCH(+).
Figure 22:
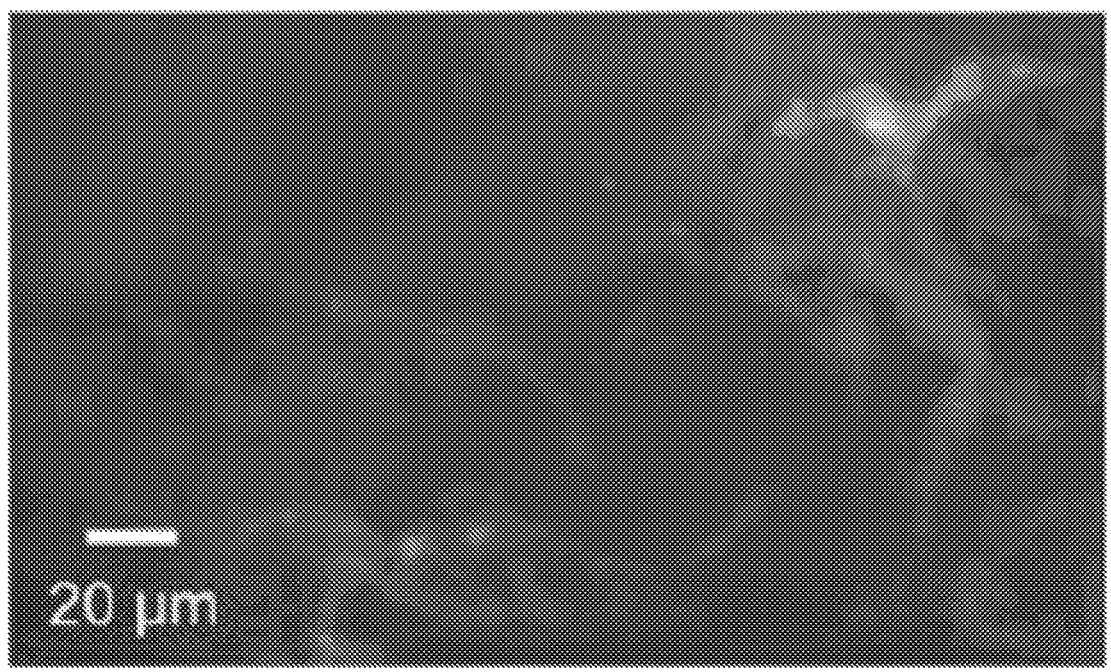
FIG. 22 shows a fluorescent photomicrograph of solutions containing ThT and an equimolar mixture of CATCH peptides.

Finally, fluorescent flocculates were observed in fluorescence photomicrographs of solutions containing ThT and an equimolar mixture of CATCH peptides (FIG. 22), whereas no fluorescent signal was observed in sample containing ThT and either CATCH peptide alone (FIG. 20-21). This observation was consistent with previous reports for solutions containing ThT and the self-assembling peptide Q11,[12] which has a similar alternating hydrophilic-hydrophobic residue core design as CATCH(+/−).[7] Taken together, these data demonstrated that CATCH(+) and CATCH(−) can co-assemble into β-sheet nanofibers when combined, yet are unable to independently assemble due to electrostatic repulsion. Therefore, CATCH peptides met the fundamental requirements for further characterization as recombinant fusion tags to integrate a functional protein ligand into supramolecular biomaterials.

Figures 24A, 24B:
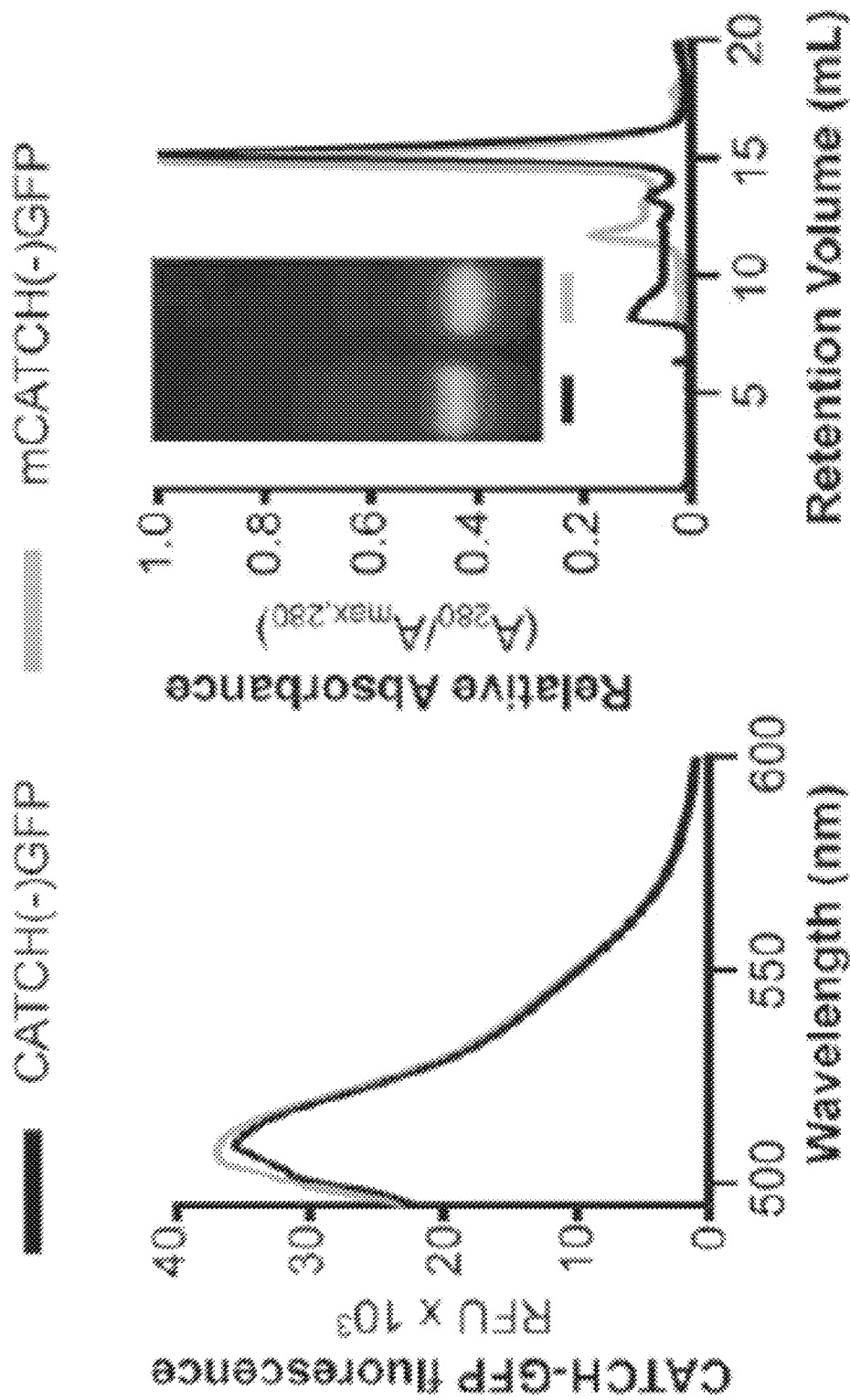
FIGS. 24A-24B show the results of an analysis of CATCH (−)GFP fusion protein expression.
Figure 25:
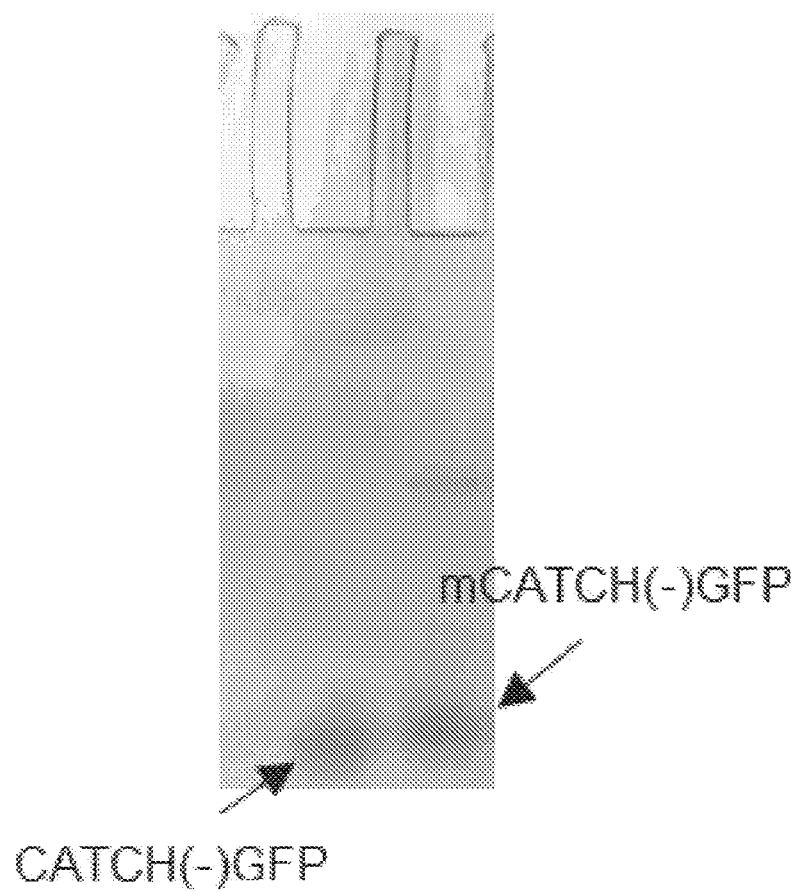
FIG. 25 shows an image of a representative gel demonstrating migration of CATCH(−)GFP and mCATCH(−)GFP.
Figure 26:
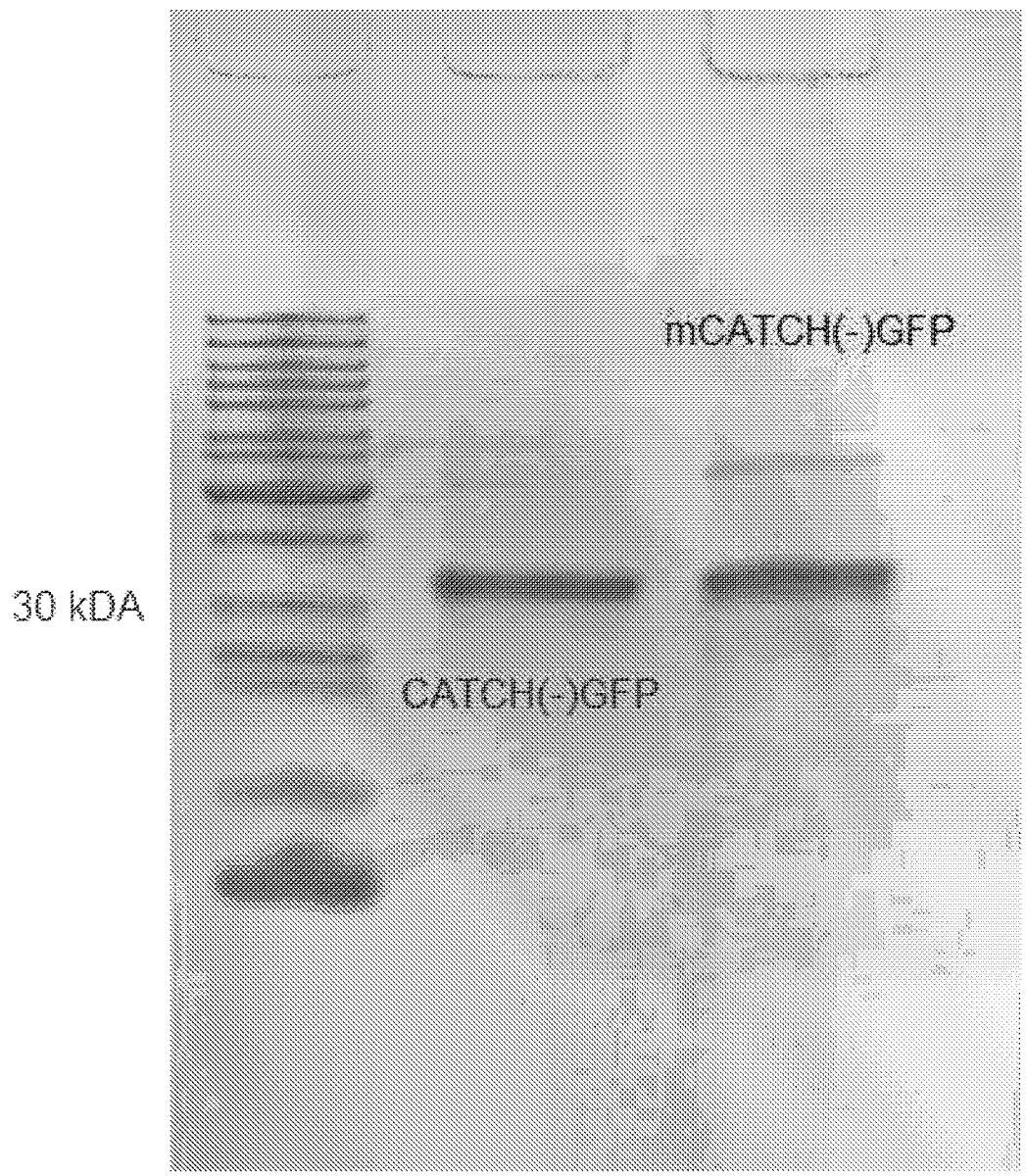
FIG. 26 shows an image of a representative gel demonstrating the molecular weight of CATCH(−)GFP and mCATCH(−)GFP.

Expression and recovery of a fluorescent CATCH fusion protein. The expression and recovery of a recombinant fusion of CATCH(−) and superfolder green fluorescent protein (GFP) herein referred to as "CATCH(−)GFP", from E. coli hosts was characterized using fluorimetry, native polyacrylamide gel electrophoresis (PAGE), and size exclusion chromatography (SEC) (FIGS. 24A-24B). GFP was an ideal candidate for these studies because perturbations to its conformation can be easily and reliably analyzed using fluorimetry and fluorescence microscopy. CATCH(-) was used to minimize the potential for misfolding or aggregation due to charge complementarity between the fusion tag and GFP, which has a net negative charge. Fluorescent CATCH(-)GFP and mCATCH(-)GFP were expressed and recovered from microbial hosts in the soluble fraction in mg/L quantities. CATCH(-)GFP and mCATCH(-)GFP demonstrated similar fluorescence emission spectra (FIG. 24A), having maxima at 509 and 508 nm, respectively, which were consistent with previous reports for superfolder GFP.[36] CATCH(-)GFP and mCATCH(-)GFP eluted from a size-exclusion column at similar retention volumes (FIG. 24B), which correlated with molecules having molecular weights of about 30 kDa. CATCH(-)GFP and mCATCH(-)GFP had similar electrophoretic mobility, migrating as a single fluorescent band under native conditions (FIG. 24B, inset; FIGS. 25-26), as expected for molecules having similar charge and molecular weight. Taken together, these data demonstrated that the CATCH(-)GFP fusion protein was recovered in high yield as a soluble monomer following expression in a microbial host.

Co-assembly of CATCH(-)GFP and CATCH peptides. The co-assembly of CATCH(-)GFP with CATCH peptides was characterized under various conditions using fluorescence microscopy and transmission electron microscopy (FIGS. 27A-27B, 28A-28B, 29A-29B, 30A-30B, 32A-32I, and 34A-34H). Fluorescent flocculates were observed in a ternary mixture of CATCH(-)GFP, CATCH(+), and CATCH(-) visualized with a fluorescence microscope (FIG. 27A), which we refer to here as a "tri-assembly" due to its three-component nature. Elongated structures having widths of ~5 nm and spanning hundreds of nm in length were observed in transmission electron micrographs of solutions containing the ternary mixture of CATCH(-)GFP, CATCH(+), and CATCH(-) (FIG. 27B). Tri-assembly nanofibers had morphological similarities to those observed in an equimolar mixture of CATCH peptides (FIG. 16), which suggested that the presence of CATCH(-)GFP did not disrupt CATCH peptide β-sheet fibrillization. Coupled with the morphological similarity of tri-assembly fluorescent flocculates to flocculates of CATCH(+) and CATCH(-) nanofibers stained with ThT (FIG. 22, these data suggested that CATCH(-)GFP integrated into CATCH peptide nanofibers. Further confirming this, diffuse fluorescence was observed in control samples containing CATCH(-)GFP alone, as well as in ternary mixtures of CATCH peptides plus the mCATCH(-)GFP variant having a non-fibrillizing CATCH tag (FIGS. 28A-28B). Notably, the latter demonstrated that CATCH(-)GFP was likely not adsorbed onto the surface of CATCH nanofibers via electrostatic complementarity, but rather integrated into CATCH nanofibers. Taken together, these data demonstrated that the CATCH fusion tag can install a folded protein into CATCH peptide nanofibers, thereby imparting functional capabilities to the resulting supramolecular tri-assembly.

Figure 31:
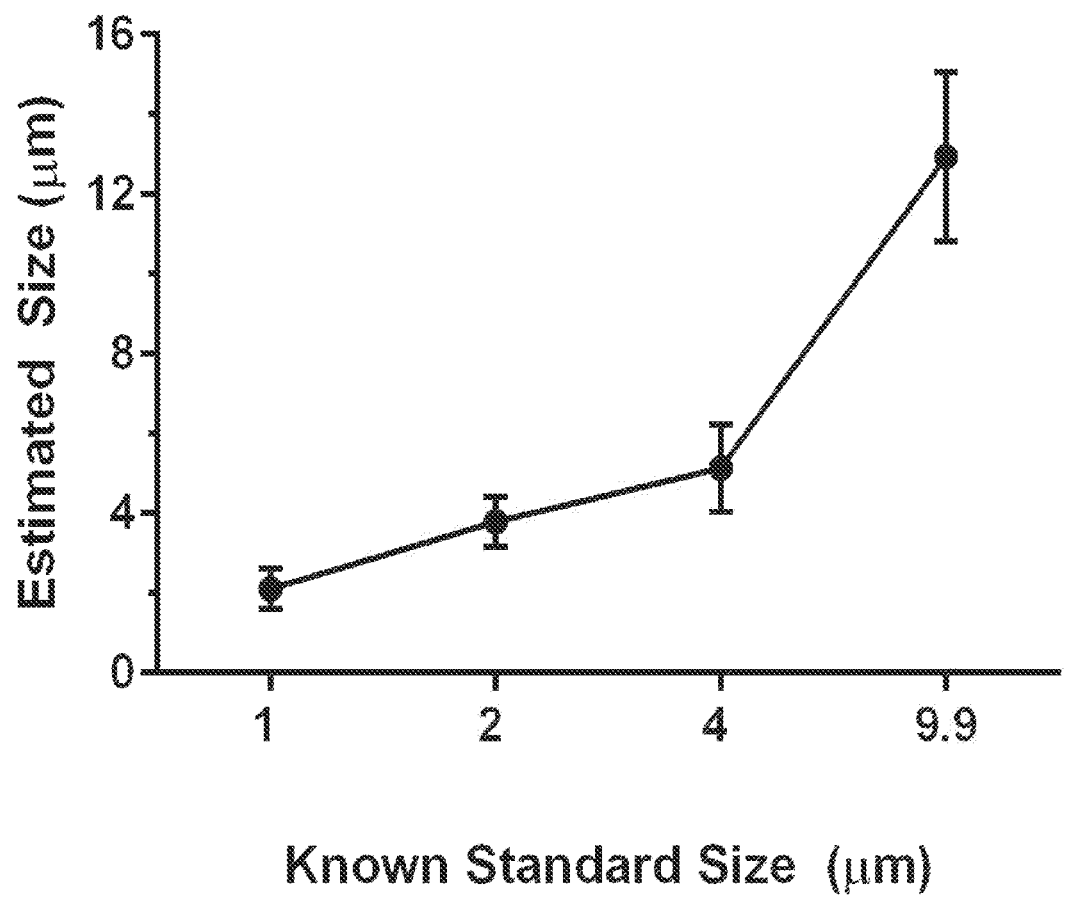
FIG. 31 shows a graph demonstrating a standard curve for estimated size of the microparticles.
Figure 33A:
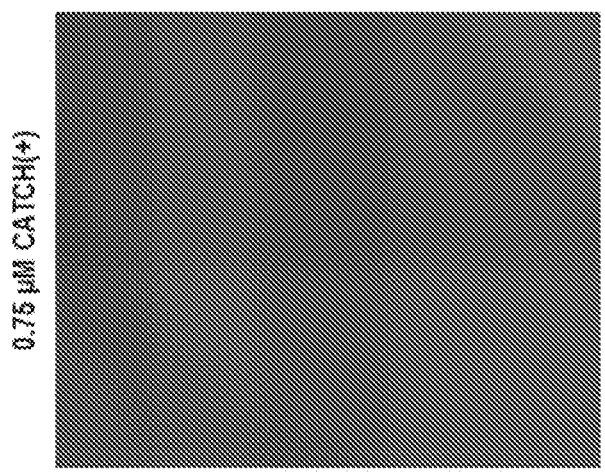
FIGS. 33A-33C show fluorescence photomicrographs of 0.75 UM of CATCH(+) (FIG. 33A), 7.5 CATCH(+) (FIG. 33B), and 100 UM of CATCH(+) (FIG. 33C).

Micron-sized fluorescent particles (i.e. "microparticles") were observed in a binary mixture of CATCH(-)GFP and CATCH(+) (FIG. 29A), which we refer to here as a "di-assembly" because of its two-component nature. No discernible nano-scale structures were present in transmission electron micrographs of the binary mixture of CATCH(-)GFP and CATCH(+) (FIG. 29B), suggesting that the resulting supramolecular di-assemblies were primarily micron-sized and therefore too large to adsorb onto TEM grids. Diffuse fluorescence observed in control samples containing CATCH(-)GFP alone (FIG. 30A), as well as in binary mixtures of CATCH(-)GFP and CATCH(+) at concentrations below 7.5 µM (FIG. 33A), which suggested that interactions between CATCH(-)GFP and CATCH(+) were required for supramolecular di-assembly of microparticles. Notably, diffuse fluorescence observed in samples of CATCH(+) and mCATCH), suggested that electrostatic complementarity alone was insufficient for supramolecular di-assembly of microparticles. FIG. 31 shows a size standard curve of commercially available fluorescent microparticles for size estimation of the di-assembly microparticles.

Figure 32A:
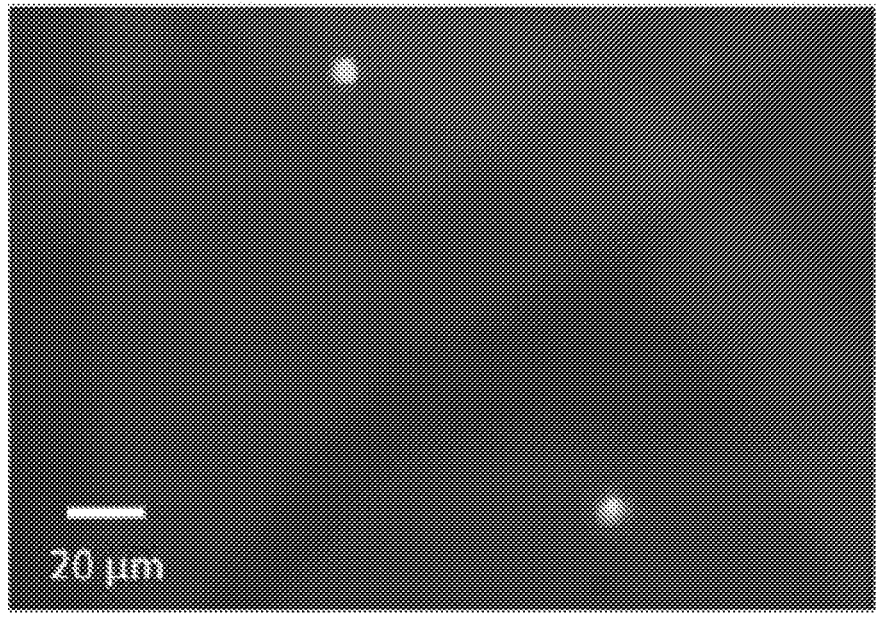
FIGS. 32A-32I demonstrate the influence of mixing on CATCH(+) and CATCH(−)GFP di-assembly size.
Figure 32B:
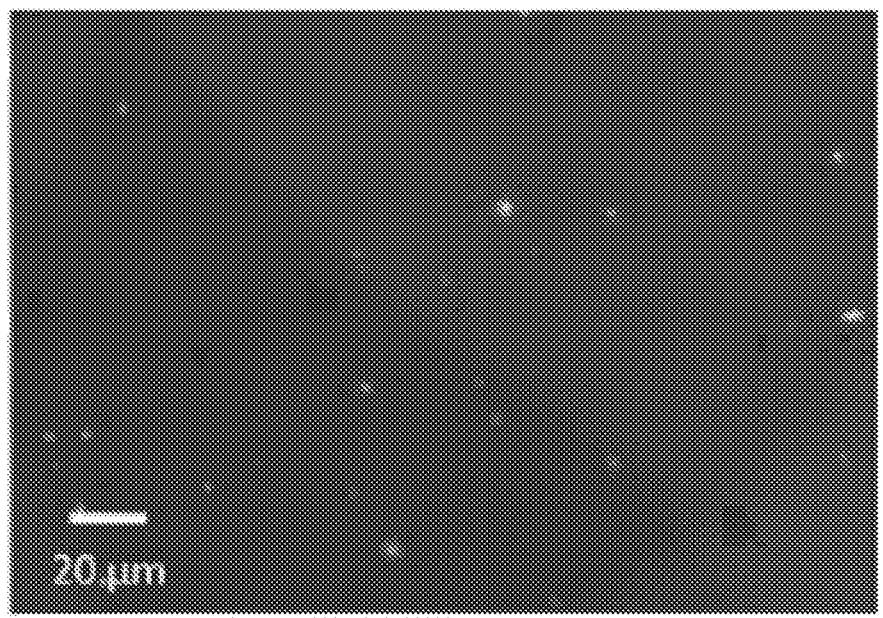
Figure 32C:
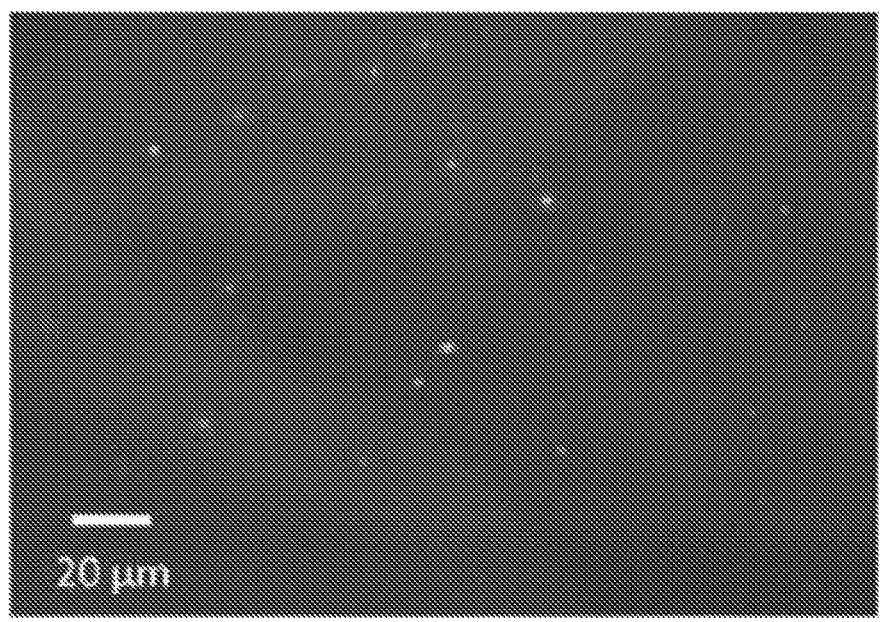
Figure 32D:
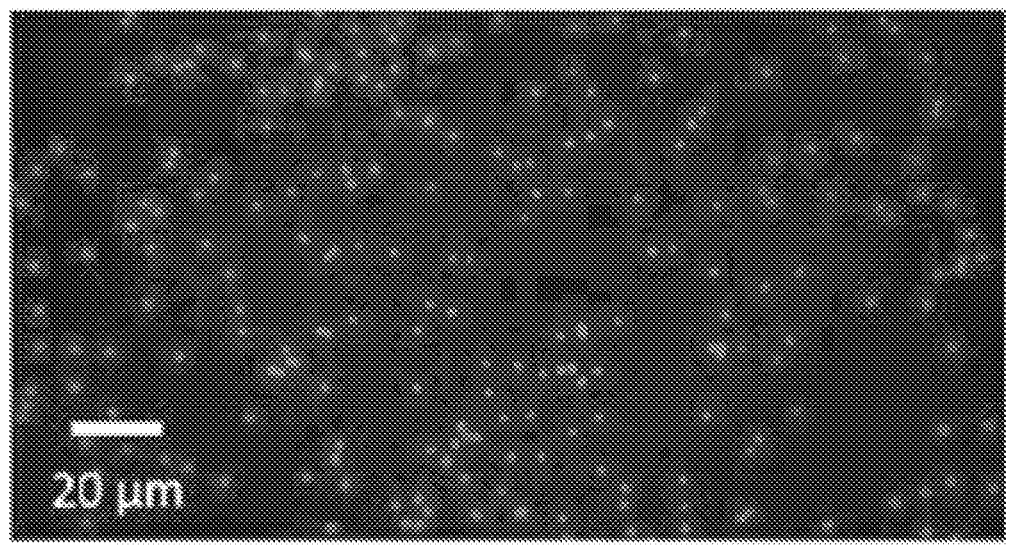
Figure 32E:
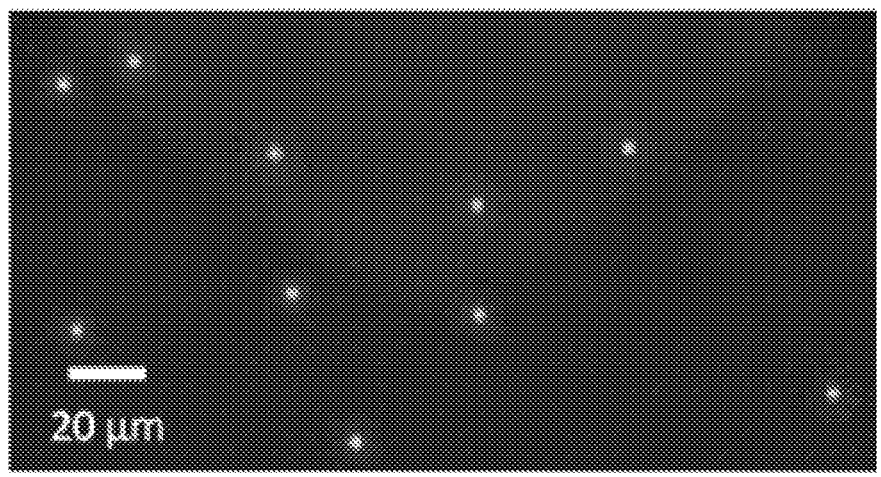
Figure 32F:
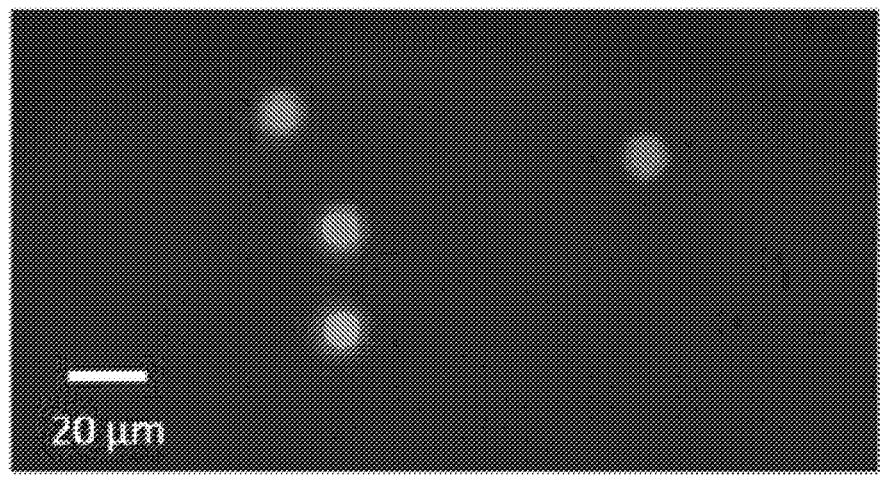
Figure 32G:
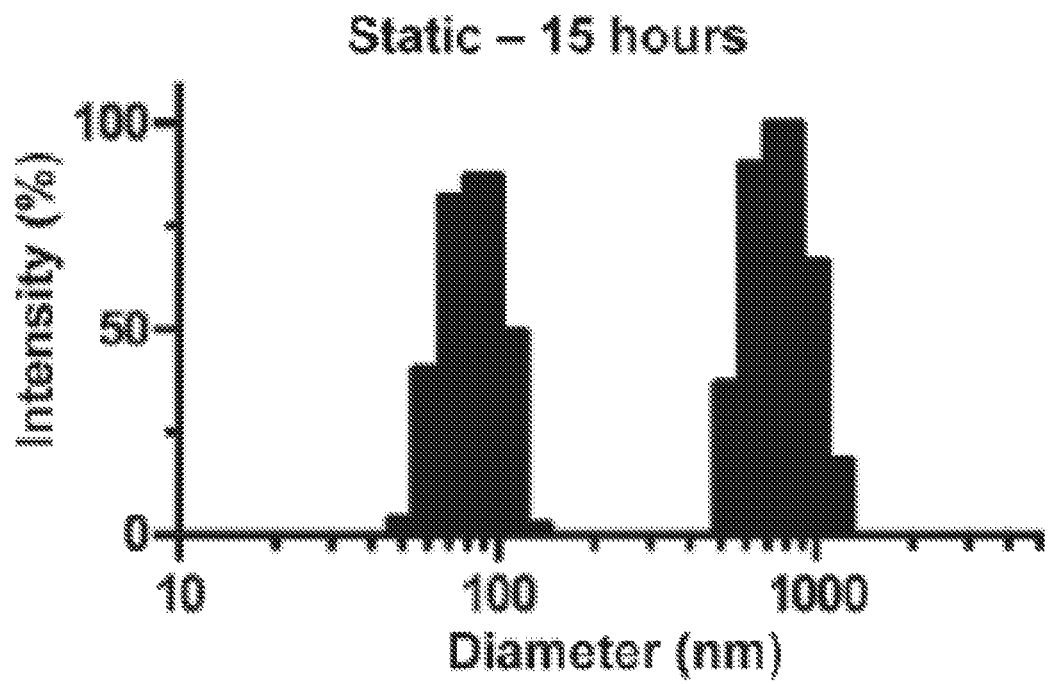
Figure 32H:
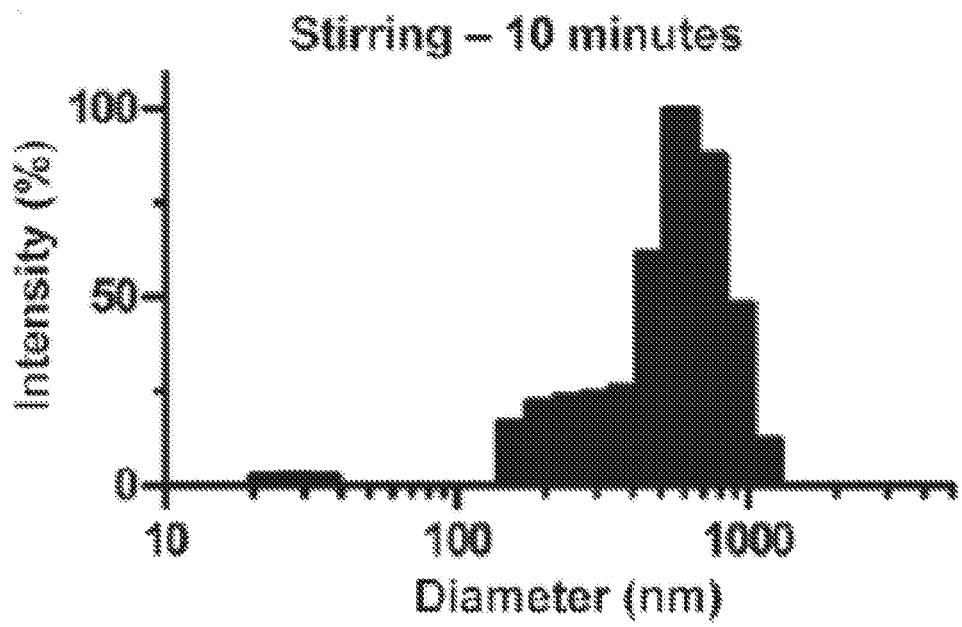
Figure 32I:
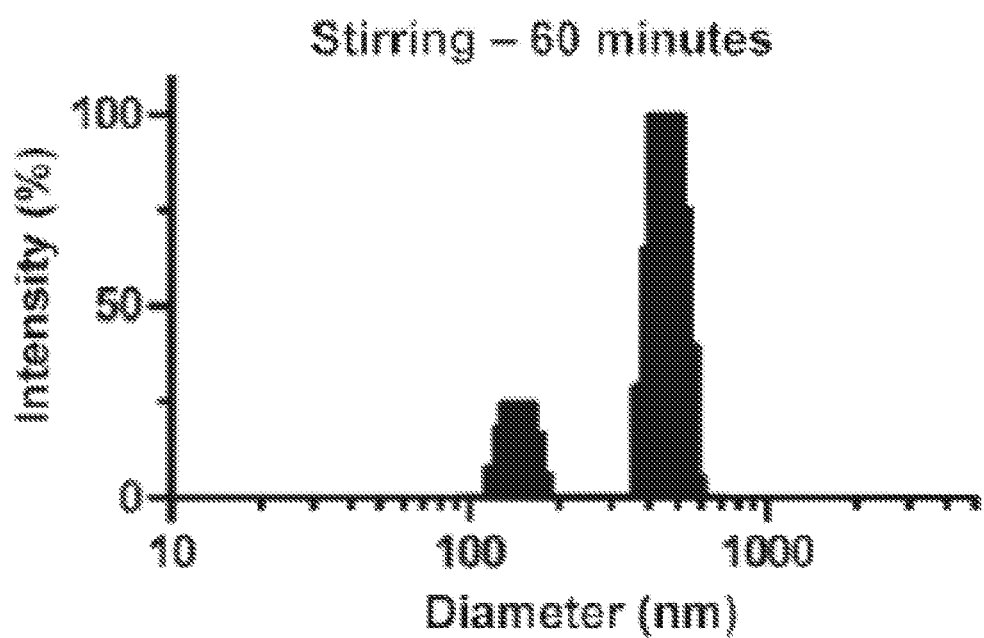
Figure 33B:
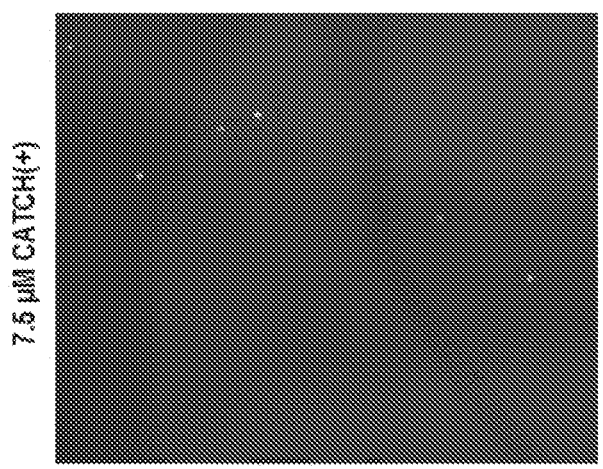
Figure 33C:
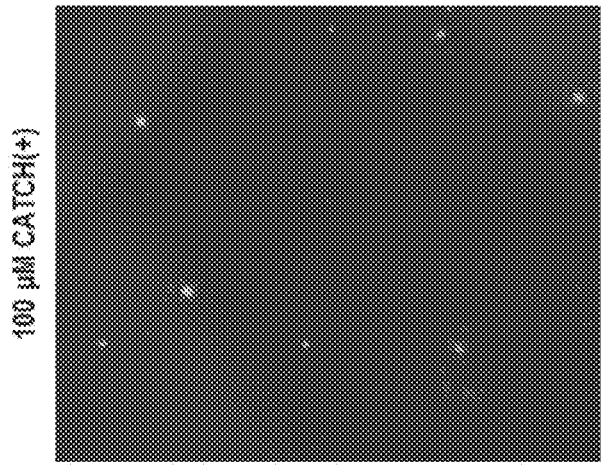
Figures 34A, 34B, 34C, 34D, 34E, 34F, 34G, 34H:
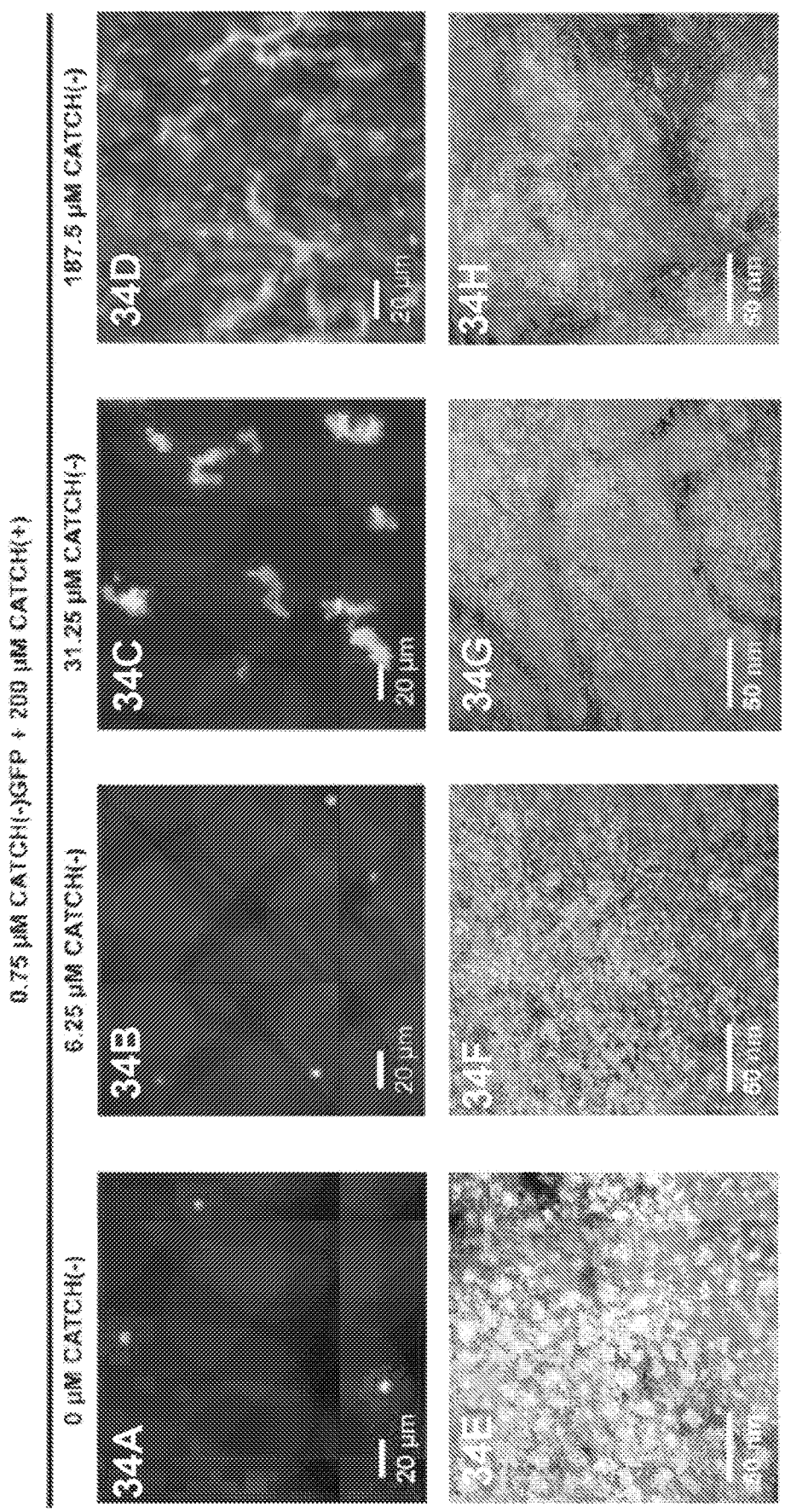
FIGS. 34A-34H demonstrate the influence of excess CATCH(−) on transition from di-assembly to tri-assembly. Fluorescence photomicrographs (FIGS. 34A-34D) and transmission electron micrographs (FIGS. 34E-34H) after 15 hours of static incubation of mixtures containing 0.75 µM CATCH(−)GFP and different concentrations of CATCH(−) (0-187.5 µM) mixed with 200 UM of CATCH(+).

Understanding the extent and kinetics of CATCH fusion protein and CATCH peptide di-assembly could also be advantageous from a practical perspective, as supramolecular microparticles with integrated functional proteins could be useful for various medical and biotechnological applications. It was envisioned that fusing CATCH(-) to GFP could introduce a significant diffusion limitation that would diminish reaction kinetics and in turn reduce the extent of reaction observed in real-time. Thus, we used fluorescence microscopy to assess the influence of incubation time and stirring on microparticle number, a qualitative measure of the extent of reaction, and microparticle size (FIGS. 32A-32I). The number of fluorescent microparticles per viewing area in binary mixtures of 0.75 µM CATCH(-)GFP and 200 µM CATCH(+) increased significantly in samples stirred for 10 or 60 minutes when compared to samples maintained under static conditions for 15 h (FIGS. 32A-32C). Consistent with this, some diffuse GFP staining was noted in the background of fluorescent photomicrographs of binary mixtures maintained under static conditions, suggesting a lower extent of reaction in the absence of mixing (FIG. 32A). Comparing fluorescence photomicrographs of binary mixtures of CATCH(-)GFP and CATCH(+) to commercially-available fluorescent microspheres of various sizes (FIGS. 32D-32F), suggested that the CATCH microparticles were about 1-2 µm in diameter. Thresholding and image analysis of fluorescence photomicrographs of commercial microspheres provided diameters that were approximately 1 µm larger than that reported by the supplier (FIGS. 33A-33C), however, and therefore could not be used to accurately measure the diameter of fluorescent CATCH microparticles. Thus, we also analyzed CATCH microparticle size using DLS (FIGS. 32G-32I). A bimodal size distribution was observed with peaks around 70-100 nm and 600-1000 nm for solutions of CATCH(-)GFP and CATCH(+) incubated overnight without stirring (i.e. "static"). In contrast, stirring solutions of CATCH(-)GFP and CATCH(+) for 10-60 min greatly reduced the population of particles in the 70-100 nm range, with the longer stirring time leading to a much narrower population of microparticles in the 600-800 nm range. The discrepancies in microparticle size determined via DLS and fluorescence microscopy are likely the result of two effects. First, particles having diameters of 70-100 nm are well below the diffraction limit required for observation via fluorescence microscopy. Second, the size of microparticles visualized with epifluorescence microscopy may appear larger due to a 'halo effect' arising from light refracted through the aqueous media surrounding the microparticle. Finally, the zeta potential of microparticles in solutions of CATCH(-)GFP and CATCH(+) stirred for 60 min was −3.11±0.14 mV at pH 7.4, suggesting that the microparticle suspension has low stability and is prone to flocculation. Taken together, these data indicated that stirring binary mixtures of CATCH(-)GFP and CATCH(+) can increase the kinetics and, in turn, extent of microparticle formation, ultimately leading to a population of functional supramolecular biomaterials having a relatively narrow sub-micron size distribution.

Finally, we used fluorescence microscopy and TEM to investigate the relationship between the composition of CATCH(−)GFP, CATCH(+), and CATCH(−) mixtures and the transition from di-assembly to tri-assembly (FIGS. 34A-34H). A ternary mixture containing 6.25 µM CATCH(−) produced fluorescent microparticles, and no discernible nano-scale structures in transmission electron micrographs, similar to binary mixtures. A ternary mixture containing 31.25 M CATCH(−) produced fluorescent flocculates, with elongated tri-assembly nanofibers having widths of about 5 nm and spanning hundreds of nm in length observed in transmission electron micrographs. Increasing the concentration of CATCH(−) to 187.5 µM increased the fluorescent flocculate density, yet the nano-scale morphology of the tri-assembly nanofibers was similar to those formed at lower CATCH(−) concentrations. Together, these data demonstrated a CATCH(−) concentration-dependent threshold for transition from di-assembly microparticles to tri-assembly nanofibers, which occurred at a total CATCH(−) concentration that was well below the critical fibrillization concentration for CATCH(−) and CATCH(+) peptide assembly in the absence of CATCH(−)GFP.

Figure 35A:
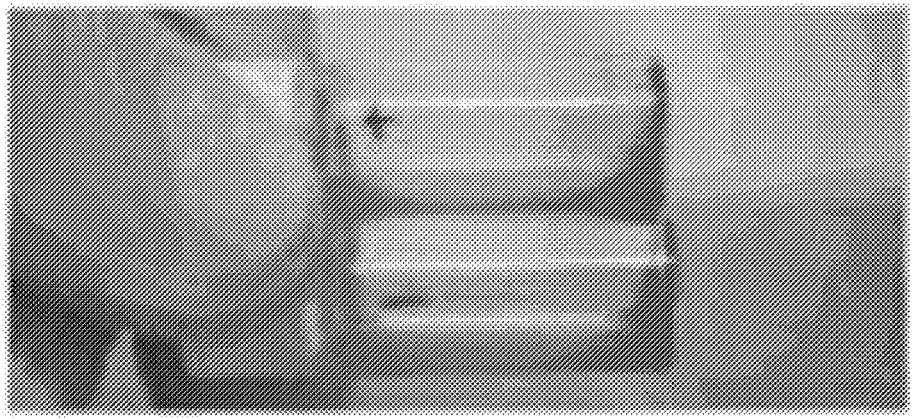
Figure 35B:
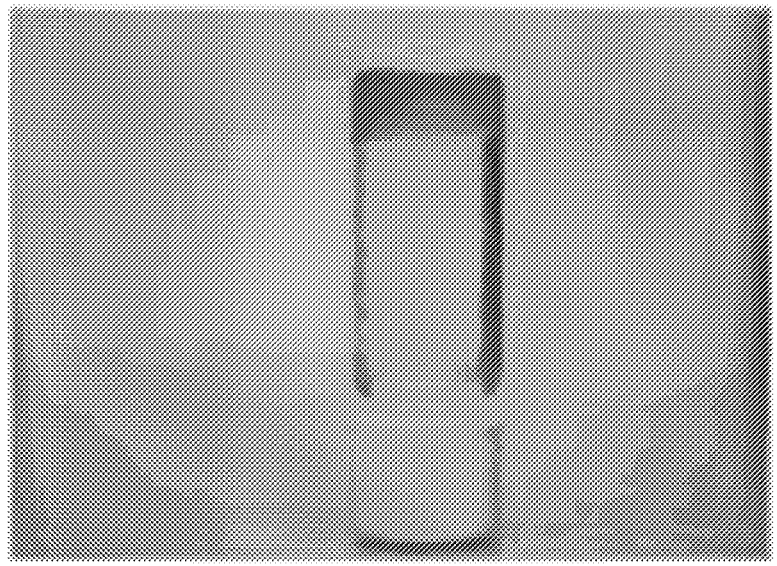
Figures 35C, 35D:
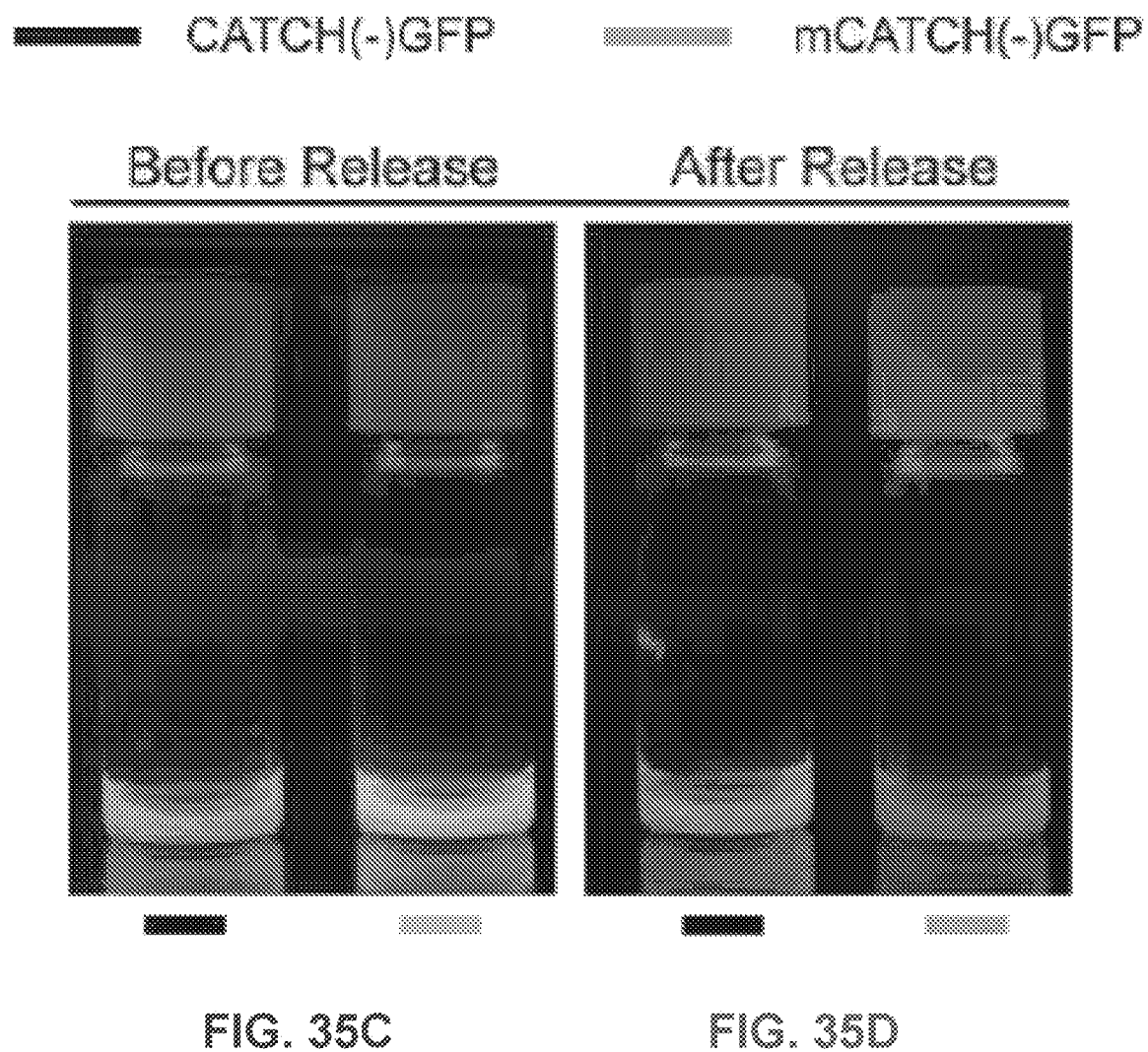
Figure 36:
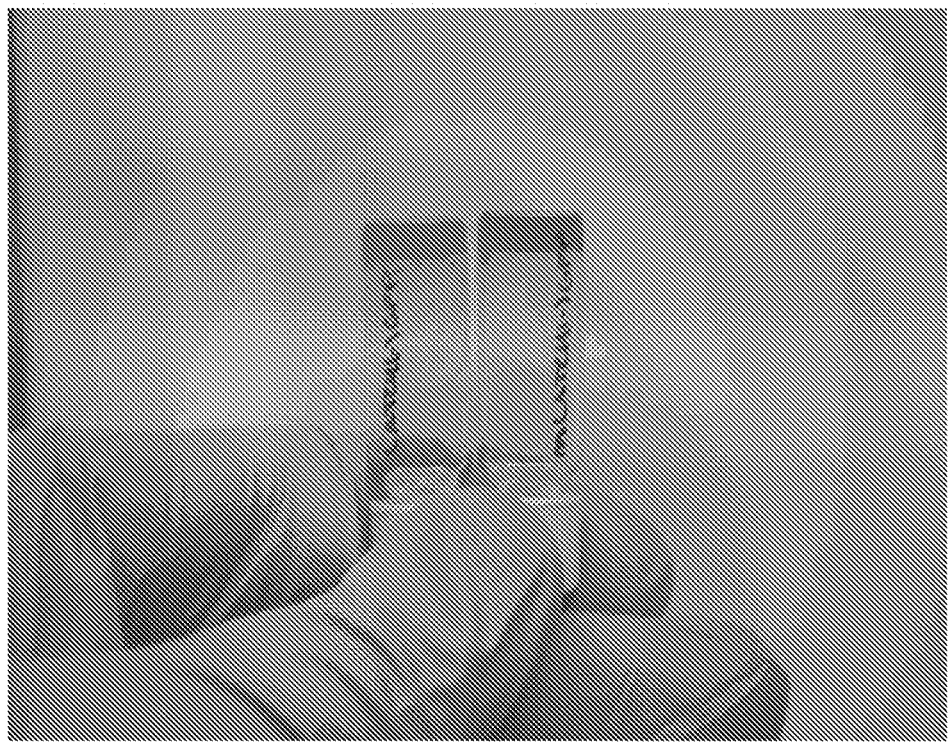
FIG. 36 shows an image of CATCH hydrogels formed in the presence of CATCH(−)GFP.

Macroscopic CATCH hydrogels with an integrated folded protein component. To demonstrate the potential of CATCH for creating functional supramolecular biomaterials with an integrated folded protein component, we characterized the formation of self-supporting macroscopic fluorescent hydrogels from ternary mixtures of CATCH(+), CATCH(−), and CATCH(−) GFP (FIGS. 35A-35G). Aqueous buffered solutions of 12 mM CATCH(+) or CATCH(−) were free flowing (FIG. 35A), but rapidly formed a self-supporting hydrogel when combined (FIG. 35B). Adding CATCH(−)GFP or mCATCH(−)GFP to the aqueous buffered CATCH(−) solution produced fluorescent hydrogels upon addition of CATCH(+) (FIG. 35C). CATCH hydrogels formed in the presence of CATCH(−)GFP retained their fluorescence when incubated under a volumetric excess of 1× PBS for 48 h, whereas a significant loss of fluorescence was observed in hydrogels formed in the presence of mCATCH(−)GFP (FIGS. 35D and 36). The loss of mCATCH(−)GFP from CATCH hydrogels was due to protein diffusion into the excess buffer, with the hydrogel and buffer approaching equilibrium by 48 h (FIGS. 35E-35G, gray bars). In contrast, no GFP was detected in the buffer layer over hydrogels formed in the presence of CATCH(−)GFP (FIGS. 35E-35G, black bars). Taken together, these data demonstrated that a covalent fusion of a folded protein and a CATCH peptide was stably installed into CATCH hydrogels without appreciable loss of activity. This was likely due to the CATCH domain of the fusion co-assembling into CATCH nanofibers, rather than adsorbing onto their surface, as a fusion protein having a mutated variant of CATCH(−) was rapidly released from hydrogels into surrounding media. Thus, CATCH can enable fabrication of supramolecular biomaterials with integrated folded protein components.

Discussion

In this Example, at least a pair of synthetic peptides that can co-assemble into β-sheet nanofibers in aqueous media via electrostatic complementarity was demonstrate and is referred to as CATCH. CATCH(+) and CATCH(−) peptides are cationic and anionic variants of Q11, a zwitterionic synthetic peptide that self-assembles into β-sheet nanofibers in aqueous media.[7] CATCH peptides rapidly co-assemble into β-sheet nanofibers when combined in aqueous media above a critical concentration, yet cannot self-assemble under identical conditions, likely due to electrostatic repulsion resulting from their net charge at neutral pH. Fibrillization of CATCH(+) and CATCH(−) was mediated by their core sequence of alternating phenylalanine residues and hydrophilic amino acids, analogous to the parent peptide Q11.[7, 40] The co-assembly behavior of CATCH peptides was similar to that of the charge-complementary synthetic peptides $P_{11}$-13 and $P_{11}$-14 developed by Aggeli et al,[25] which only assembled into elongated β-sheet nanofibers when combined. Together, these observations suggest that the common primary sequence motif shared by CATCH peptides and the charge-complementary $P_{11}$ peptides, in which charged and polar amino acids flank a core of alternating hydrophobic and hydrophilic residues, is likely to be broadly applicable for designing synthetic peptides that selectively co-assemble into β-sheet nanofibers. However, inserting charged residues within the primary sequence may also introduce an energetic penalty for peptide β-sheet fibrillization, given that the critical concentration for CATCH peptide co-assembly was more than an order of magnitude higher than that of Q11, which self-assembles into β-sheet nanofibers at a concentration of ~10 µM.[7] Future efforts could systematically investigate CATCH primary sequences to identify motifs that confer robust electrostatic control of assembly, yet decrease the critical fibrillization concentration.

The CATCH system can create a versatile recombinant fusion tag to install folded proteins into supramolecular biomaterials to endow them with specific functional features. For a fusion tag to be broadly useful, it should not drive protein aggregation or disrupt protein folding during expression or purification, a noted limitation for recombinant tags having high propensity for self-assembly into β-sheet nanofibers.[24, 50] Proteins that self-assemble into nanofibers in response to specific stimuli, such as pH, can address this limitation.[1, 2, 28, 33] However, the functional protein domain appended onto the assembly domain must have a conformation that is insensitive to the assembly stimulus. Additionally, the size of the functional domain may need to be limited to enable accurate translation and high yield expression if the assembly domain is large. Therefore, key features of more broadly useful recombinant tags to install folded proteins into supramolecular biomaterials would include selective assembly in response to a mild external stimulus that is unlikely to perturb protein conformation, as well as a relatively low molecular weight to enable co-expression with fusion partners having a range of molecular weights. CATCH peptides were ideal candidates in this regard, given their relatively low molecular weight (about 1.5 kDa) and tightly controlled mixing-induced assembly in aqueous media at neutral pH.

Figure 37:
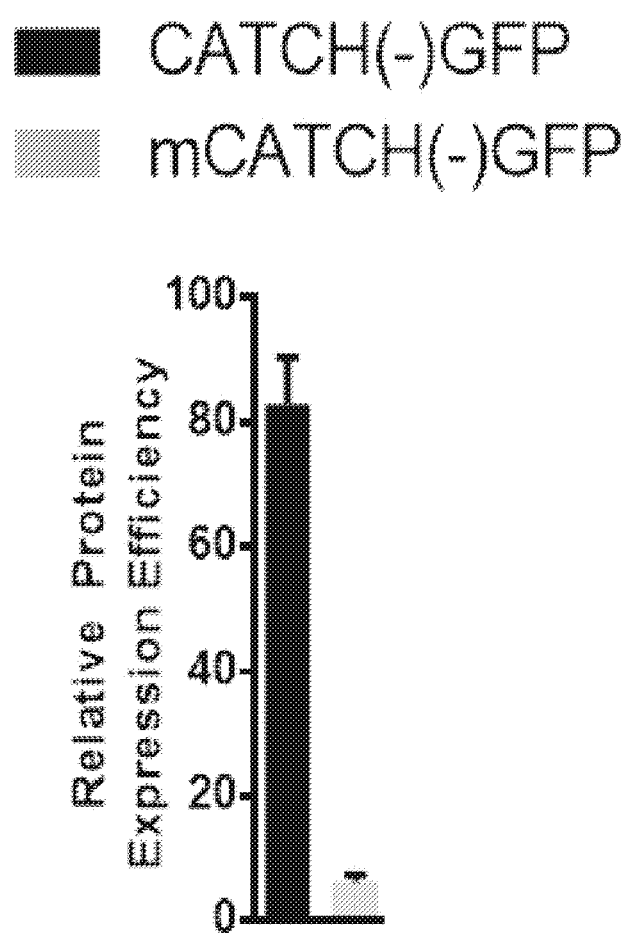
FIG. 37 shows a graph that can demonstrate that a fusion of CATCH(−) and GFP that was expressed and recovered as a soluble monomer from E. coli hosts in mg/L yields that were often as good or better than those for an mCATCH(−) GFP variant having a mutated fusion tag that cannot assemble into β-sheet nanofibers.
Figure 38A:
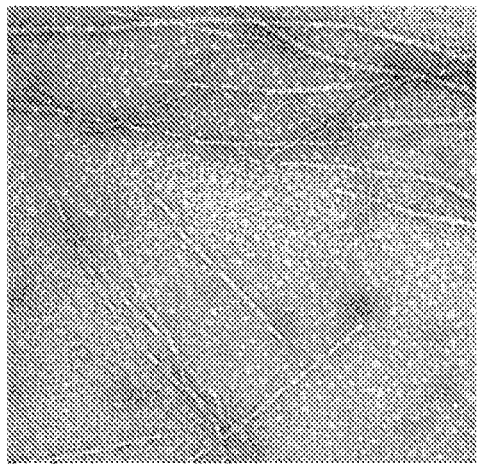
FIGS. 38A-38D show transmission electron micrographs of various combinations of CATCH peptides. Scale bar=0.1 µm.
Figure 38B:
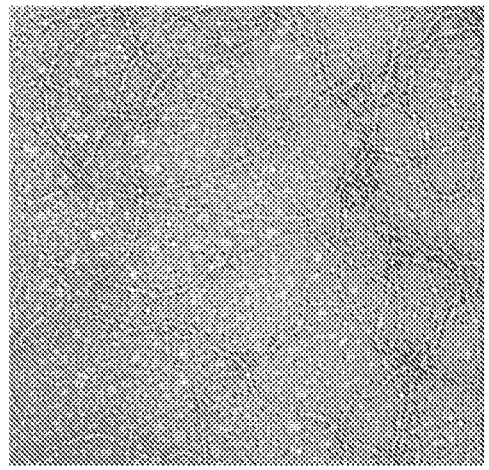
Figure 38C:
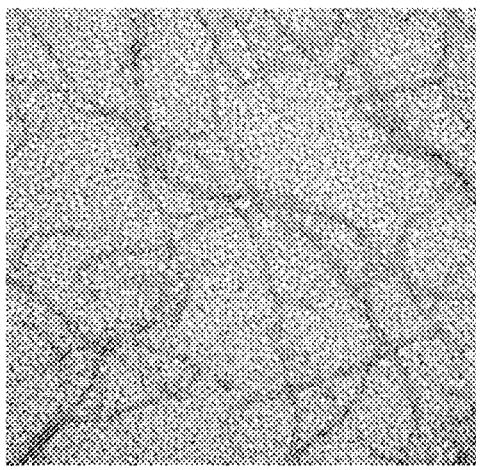
Figure 38D:
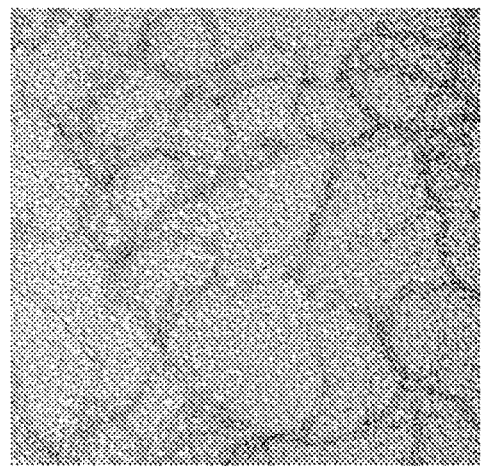

In this report it was demonstrated that a fusion of CATCH (−) and GFP was expressed and recovered as a soluble monomer from *E. coli* hosts in mg/L yields that were often as good or better than those for an mCATCH(−)GFP variant having a mutated fusion tag that cannot assemble into β-sheet nanofibers (FIG. 37). Taken together with data demonstrating that the fluorescence properties of GFP were similar when fused to CATCH(−) or mCATCH(−), this data demonstrated that the CATCH tag did not mediate GFP aggregation or disrupt GFP folding during expression in *E. coli*, likely because the net charge on CATCH(−) inhibited its self-assembly within bacterial cytoplasm. In contrast, a prior report demonstrated that a recombinant fusion of GFP and βTail, a β-sheet fibrillizing tag having slow self-assembly kinetics, was typically recovered as a soluble monomer from E. coli hosts in lower yield than a GFP fusion having a mutated βTail tag that was unable to assemble into β-sheet nanofibers.[19] Thus, our observations suggest that fusion tags with energetically-controlled assembly properties may be advantageous over kinetically-controlled tags for limiting fusion protein aggregation during expression. Additionally, the flexibility of choosing a CATCH tag that has a similar net charge as the folded protein domain may further improve expression, for example, by preventing electrostatic aggregation between CATCH and its fusion partner.

Beyond facilitating fusion protein expression, CATCH also met the criteria for a recombinant fusion tag that can endow supramolecular biomaterials with the functional properties of folded proteins. Herein, we demonstrated that simply combining CATCH(−)GFP with CATCH peptides in aqueous media yielded fluorescent supramolecular biomaterials via integration of GFP into the resulting assemblies in a CATCH-dependent manner. Interestingly, the structural features of the resulting fluorescent supramolecular biomaterials could be varied by altering the concentration or composition of CATCH peptides added to solutions containing CATCH(−)GFP. For example, ternary mixtures of CATCH(−)GFP and both CATCH peptides produced soluble fluorescent nanofibers or macroscopic nanofibrillar hydrogels depending on the peptide concentration, whereas binary mixtures of CATCH(−)GFP and its complementary CATCH(+) peptide yielded micron-sized particles. We speculate that supramolecular di-assembly of microparticles in binary mixtures may be due to β-sheet fibrillization of CATCH(−)GFP and CATCH(+), analogous to the tri-assembly of fluorescent nanofibers from ternary mixtures. However, given that CATCH peptides adopted a primarily random-coil conformation at concentrations of 50 µM, observing CATCH(−)GFP and CATCH(+) co-assembly into microparticles at concentrations that were well below the critical fibrillization concentration of CATCH peptides was unexpected. One possible explanation is arrived at by rationalizing that the magnitude of the system free energy change is likely primarily governed by differences in the entropic penalty of organizing CATCH(−) or CATCH(−)GFP into a supramolecular structure. It can be assumed that any entropic gain due to release of water molecules from the surface of CATCH(−) is similar for peptides and fusion proteins (i.e. that the protein domain does not alter the ordering of water molecules around CATCH(−), or any hydrophobic effect is independent of the protein domain). Second, it can be assumed that the entropic penalty for organizing CATCH(+) into a supramolecular structure is similar regardless of whether the peptide is binding to CATCH(−) peptide or a CATCH(−) fusion protein. Third, it can be assumed that enthalpic contributions from binding of CATCH(−) and CATCH(+) are also similar for peptides and fusion proteins (i.e. that protein-protein or protein-peptide interactions are negligible). Finally, it can be inferred that fusing CATCH(−) to a large protein molecule will reduce the translational and rotational entropy of the peptide, analogous to immobilizing the peptide onto a solid phase. In other words, the entropic penalty for organizing freely diffusible CATCH(−) into a supramolecular structure is much greater than that for CATCH(−)GFP. Therefore, the magnitude of the free energy change for co-assembly of CATCH(+) and CATCH(−)GFP is much greater, and thus more favorable, than that for CATCH(+) and CATCH(−). It can be expected that this same relationship would hold for co-assembly of CATCH(−) peptides with a CATCH(+) fusion protein, while co-assembly of CATCH(−) and CATCH(+) fusion proteins may be even more energetically favorable.

Beyond informing a mechanistic basis for CATCH(−) GFP and CATCH(+) di-assembly into supramolecular microparticles, considering the behavior of the system as it approached equilibrium could also be advantageous from a practical perspective. In particular, a near-quantitative co-assembly reaction could ultimately be useful for fabricating functional supramolecular microparticles for various medical and biotechnological applications. Here, we observed that the kinetics and extent of di-assembly of CATCH(−) GFP and CATCH(+) into microparticles were increased by mixing, as stirring for 10-60 minutes qualitatively increased the number of microparticles observed within the binary mixtures. Interestingly, however, it was noted that mixing seemed to preferentially induce nucleation of new microparticles, rather than propagating growth of larger microparticles, as particle size distribution narrowed and centered about 700 nm with increasing stirring time. Thus, it remains to be determined if the di-assembly process and resultant features of supramolecular microparticles, such as the kinetics, extent of reaction, and size distribution, are influenced by the folded protein domain or net charge of the CATCH tag. Toward that end, future work will move toward characterizing microparticle fabrication with CATCH fusions consisting of folded proteins having functional properties that are relevant for biomedical or biotechnological applications.

Interesting CATCH assembly behaviors were observed in the transition from binary to ternary mixtures. In particular, low concentrations of CATCH(−) peptide in ternary mixtures yielded fluorescent microparticles similar to those observed in binary mixtures, whereas increasing the CATCH (−) concentration induced a transition to fluorescent nanofibers whose relative density increased with CATCH(−) concentration. Unexpectedly, CATCH(−) and CATCH(+) peptides co-assembled into fluorescent nanofibers in the presence of CATCH(−)GFP at peptide concentrations that were well below the critical concentration for peptide co-assembly in the absence of a fusion protein. Building from the thermodynamic considerations of di-assembly discussed above, the lower concentrations required for peptide co-assembly in the presence of the fusion protein may be explained by rapid, energetically favorable formation of stable CATCH(−)GFP and CATCH(+) nuclei that propagate co-assembly of CATCH(−) and CATCH(+) peptides, analogous to seeds in samples of amyloid-β.[16] Thus, assembly of CATCH fusion proteins into supramolecular biomaterials is not governed exclusively by a binary or ternary mixture, but rather by the relative concentration of each molecular component within the system. This flexibility in supramolecular assembly structural features, coupled with the versatility of CATCH tags for installing a wide variety of functional proteins, suggests the enormous potential of the CATCH system for creating new biomaterials for a broad assortment of applications.

Summary

Supramolecular assembly is receiving increasing attention for fabricating functional biomaterials for various biomedical and biotechnological applications, including tissue engineering, regenerative medicine, immunology, biosensors, and chemical synthesis. To be useful for these applications, however, supramolecular biomaterials must often demonstrate functional capabilities, such as molecular recognition, antigen display, tunable drug release, catalysis, or fluorescence. Installing molecules having particular functional properties is often required to endow supramolecular biomaterials with the desired functional capabilities. Toward this end, we created a pair of anionic and cationic synthetic peptides, referred to as "CATCH" or Co-Assembly Tags based on CHarge complementarity, to install folded proteins into supramolecular biomaterials. CATCH peptides were designed to co-assemble into β-sheet nanofibers when combined, yet resist self-assembly due to electrostatic repulsion. This electrostatically controlled assembly enabled high yield production of soluble CATCH(−)GFP by *E. coli*. Binary mixtures of CATCH(−)GFP and its charge-complementary peptide assembled into fluorescent microparticles, whereas ternary mixtures of CATCH(−)GFP and both CATCH peptides yielded fluorescent nanofibers and macroscopic hydrogels. A reliable approach for stable integration of folded proteins into supramolecular assemblies is likely to be broadly useful for creating biomaterials with more sophisticated functional capabilities that greatly advance the state-of-the-art. Thus, the CATCH system can be useful in addressing the impending functionality bottleneck imposed by continued reliance on unfolded peptides and small organic compounds as functional components within biomaterials.

REFERENCES FOR EXAMPLE 1

1. A J Baldwin, Bader R, Christodoulou J, MacPhee C E, Dobson C M, Barker P D. Cytochrome display on amyloid fibrils. J Am Chem Soc. 2006; 128(7):2162-3.
2. U Baxa, Speransky V, Steven A C, Wickner R B. Mechanism of inactivation on prion conversion of the *Saccharomyces cerevisiae* Ure2 protein. Proc Natl Acad Sci USA. 2002; 99(8):5253-60.
3. M Black, Trent A, Kostenko Y, Lee J S, Olive C, Tirrell M. Self-assembled peptide amphiphile micelles containing a cytotoxic T-cell epitope promote a protective immune response in vivo. Adv Mater. 2012; 24(28):3845-9.
4. C J Bowerman, Nilsson B L. Self-assembly of amphipathic beta-sheet peptides: insights and applications. Biopolymers. 2012; 98(3):169-84.
5. J Chen, Pompano R R, Santiago F W, Maillat L, Sciammas R, Sun T, Han H, Topham D J, Chong A S, Collier J H. The use of self-adjuvanting nanofiber vaccines to elicit high-affinity B cell responses to peptide antigens without inflammation. Biomaterials. 2013; 34(34):8776-85.
6. L W Chow, Wang L J, Kaufman D B, Stupp S I. Self-assembling nanostructures to deliver angiogenic factors to pancreatic islets. Biomaterials. 2010; 31(24):6154-61.
7. J H Collier, Messersmith P B. Enzymatic modification of self-assembled peptide structures with tissue transglutaminase. Bioconjug Chem. 2003; 14(4):748-55.
8. J H Collier, Rudra J S, Gasiorowski J Z, Jung J P. Multi-component extracellular matrices based on peptide self-assembly. Chem Soc Rev. 2010; 39(9):3413-24.
9. M E Davis, Hsieh P C, Takahashi T, Song Q, Zhang S, Kamm R D, Grodzinsky A J, Anversa P, Lee R T. Local myocardial insulin-like growth factor 1 (IGF-1) delivery with biotinylated peptide nanofibers improves cell therapy for myocardial infarction. Proc Natl Acad Sci USA. 2006; 103(21):8155-60.
10. M E Davis, Motion J P, Narmoneva D A, Takahashi T, Hakuno D, Kamm R D, Zhang S, Lee R T. Injectable self-assembling peptide nanofibers create intramyocardial microenvironments for endothelial cells. Circulation. 2005; 111(4):442-50.
11. X Du, Zhou J, Shi J, Xu B. Supramolecular Hydrogelators and Hydrogels: From Soft Matter to Molecular Biomaterials. Chem Rev. 2015; 115(24):13165-307.
12. M M Fettis, Wei Y, Restuccia A, Kurian J, Wallet S M, Hudalla G A. Microgels with tunable affinity-controlled protein release via desolvation of self-assembled peptide nanofibers. in press. 2016.
13. M O Guler, Soukasene S, Hulvat J F, Stupp S I. Presentation and recognition of biotin on nanofibers formed by branched peptide amphiphiles. Nano Lett. 2005; 5(2):249-52.
14. L A Haines-Butterick, Salick D A, Pochan D J, Schneider J P. In vitro assessment of the pro-inflammatory potential of beta-hairpin peptide hydrogels. Biomaterials. 2008; 29(31):4164-9.
15. T C Holmes, de Lacalle S, Su X, Liu G, Rich A, Zhang S. Extensive neurite outgrowth and active synapse formation on self-assembling peptide scaffolds. Proc Natl Acad Sci USA. 2000; 97(12):6728-33.
16. P Hortschansky, Schroeckh V, Christopeit T, Zandomeneghi G, Fandrich M. The aggregation kinetics of Alzheimer's beta-amyloid peptide is controlled by stochastic nucleation. Protein Sci. 2005; 14(7):1753-9.
17. P C Hsieh, Davis M E, Gannon J, MacGillivray C, Lee R T. Controlled delivery of PDGF-BB for myocardial protection using injectable self-assembling peptide nanofibers. J Clin Invest. 2006; 116(1):237-48.
18. G A Hudalla, Collier J H. Supramolecular artificial extracellular matrices. In: Hudalla G A, Murphy W L, editors. Mimicking the Extracellular Matrix: The Intersection of Matrix Biology and Biomaterials. London: Royal Society of Chemistry; 2015.
19. G A Hudalla, Sun T, Gasiorowski J Z, Han H, Tian Y F, Chong A S, Collier J H. Gradated assembly of multiple proteins into supramolecular nanomaterials. Nat Mater. 2014; 13(8):829-36.
20. J P Jung, Gasiorowski J Z, Collier J H. Fibrillar peptide gels in biotechnology and biomedicine. Biopolymers. 2010; 94(1):49-59.
21. J P Jung, Moyano J V, Collier J H. Multifactorial optimization of endothelial cell growth using modular synthetic extracellular matrices. Integr Biol (Camb). 2011; 3(3):185-96.
22. J P Jung, Nagaraj A K, Fox E K, Rudra J S, Devgun J M, Collier J H. Co-assembling peptides as defined matrices for endothelial cells. Biomaterials. 2009; 30(12):2400-10.
23. S Khan, Sur S, Dankers P Y, da Silva R M, Boekhoven J, Poor T A, Stupp S I. Post-assembly functionalization of supramolecular nanostructures with bioactive peptides and fluorescent proteins by native chemical ligation. Bioconjug Chem. 2014; 25(4):707-17.
24 W Kim, Kim Y, Min J, Kim D J, Chang Y T, Hecht M H. A high-throughput screen for compounds that inhibit aggregation of the Alzheimer's peptide. ACS Chem Biol. 2006; 1(7):461-9.
25. S Kyle, Felton S H, McPherson M J, Aggeli A, Ingham E. Rational molecular design of complementary self-assembling peptide hydrogels. Adv Healthc Mater. 2012; 1(5):640-5.
26. S S Lee, Hsu E L, Mendoza M, Ghodasra J, Nickoli M S, Ashtekar A, Polavarapu M, Babu J, Riaz R M, Nicolas J D, Nelson D, Hashmi S Z, Kaltz S R, Earhart J S, Merk B R, Mckee J S, Bairstow S F, Shah R N, Hsu W K, Stupp S I. Gel scaffolds of BMP-2-binding peptide amphiphile nanofibers for spinal arthrodesis. Adv Healthc Mater. 2015; 4(1):131-41.
27. S S Lee, Huang B J, Kaltz S R, Sur S, Newcomb C J, Stock S R, Shah R N, Stupp S I. Bone regeneration with low dose BMP-2 amplified by biomimetic supramolecular nanofibers within collagen scaffolds. Biomaterials. 2013; 34(2):452-9.
28. Y Leng, Wei H P, Zhang Z P, Zhou Y F, Deng J Y, Cui Z Q, Men D, You X Y, Yu Z N, Luo M, Zhang X E. Integration of a Fluorescent Molecular Biosensor into Self-Assembled Protein Nanowires: A Large Sensitivity Enhancement. Angew Chem Int Edit. 2010; 49(40):7243-6.
29. Z N Mahmoud, Gunnoo S B, Thomson A R, Fletcher J M, Woolfson D N. Bioorthogonal dual functionalization of self-assembling peptide fibers. Biomaterials. 2011; 32(15):3712-20.
30. J B Matson, Zha R H, Stupp S I. Peptide Self-Assembly for Crafting Functional Biological Materials. Curr Opin Solid State Mater Sci. 2011; 15(6):225-35.
31. S Matsumura, Uemura S, Mihara H. Construction of biotinylated peptide nanotubes for arranging proteins. Mol Biosyst. 2005; 1(2):146-8.
32. N Mehrban, Abelardo E, Wasmuth A, Hudson K L, Mullen L M, Thomson A R, Birchall M A, Woolfson D N. Assessing cellular response to functionalized alpha-helical peptide hydrogels. Adv Healthc Mater. 2014; 3(9): 1387-91.
33. D Men, Guo Y C, Zhang Z P, Wei H P, Zhou Y F, Cui Z Q, Liang X S, Li K, Leng Y, You X Y, Zhang X E. Seeding-induced self-assembling protein nanowires dramatically increase the sensitivity of immunoassays. Nano Lett. 2009; 9(6):2246-50.
34. A C Mendes, Baran E T, Reis R L, Azevedo H S. Self-assembly in nature: using the principles of nature to create complex nanobiomaterials. Wiley Interdiscip Rev Nanomed Nanobiotechnol. 2013; 5(6):582-612.
35 A Miyachi, Takahashi T, Matsumura S, Mihara H. Peptide nanofibers modified with a protein by using designed anchor molecules bearing hydrophobic and functional moieties. Chemistry. 2010; 16(22):6644-50.
36. J D Pedelacq, Cabantous S, Tran T, Terwilliger T C, Waldo G S. Engineering and characterization of a superfolder green fluorescent protein. Nat Biotechnol. 2006; 24(1):79-88.
37. R R Pompano, Chen J, Verbus E A, Han H, Fridman A, McNeely T, Collier J H, Chong A S. Titrating T-cell epitopes within self-assembled vaccines optimizes CD4+ helper T cell and antibody outputs. Adv Healthc Mater. 2014; 3(11):1898-908.
38. M Reches, Gazit E. Biological and chemical decoration of peptide nanostructures via biotin-avidin interactions. J Nanosci Nanotechno. 2007; 7(7):2239-45.
39. A Restuccia, Tian Y F, Collier J H, Hudalla G A. Self-assembled glycopeptide nanofibers as modulators of galectin-1 bioactivity. Cell Mol Bioeng. 2015; 8(3):471-87.
40. J S Rudra, Sun T, Bird K C, Daniels M D, Gasiorowski J Z, Chong A S, Collier J H. Modulating adaptive immune responses to peptide self-assemblies. ACS Nano. 2012; 6(2):1557-64.
41. J S Rudra, Tian Y F, Jung J P, Collier J H. A self-assembling peptide acting as an immune adjuvant. Proc Natl Acad Sci USA. 2010; 107(2):622-7.
42. S Sangiambut, Channon K, Thomson N M, Sato S, Tsuge T, Doi Y, Sivaniah E. A robust route to enzymatically functional, hierarchically self-assembled peptide frameworks. Advanced Materials. 2013; 25(19):2661-5.
43. T Sawada, Mihara H. Dense surface functionalization using peptides that recognize differences in organized structures of self-assembling nanomaterials. Mol Biosyst. 2012; 8(4):1264-74.
44. T Sawada, Takahashi T, Mihara H. Affinity-based screening of peptides recognizing assembly states of self-assembling peptide nanomaterials. Journal of the American Chemical Society. 2009; 131(40):14434-41.
45. J C Stendahl, Wang L J, Chow L W, Kaufman D B, Stupp S I. Growth factor delivery from self-assembling nanofibers to facilitate islet transplantation. Transplantation. 2008; 86(3):478-81.
46. Y F Tian, Devgun J M, Collier J H. Fibrillized peptide microgels for cell encapsulation and 3D cell culture. Soft Matter. 2011; 7(13):6005-11.
47 P S Vassar, Culling C F. Fluorescent stains, with special reference to amyloid and connective tissues. Arch Pathol. 1959; 68:487-98.
48. M J Webber, Appel E A, Meijer E W, Langer R. Supramolecular biomaterials. Nat Mater. 2016; 15(1):13-26.
49. G M Whitesides, Boncheva M. Beyond molecules: self-assembly of mesoscopic and macroscopic components. Proc Natl Acad Sci USA. 2002; 99(8):4769-74.
50. W Wu, Xing L, Zhou B, Lin Z. Active protein aggregates induced by terminally attached self-assembling peptide ELK16 in *Escherichia coli*. Microb Cell Fact. 2011; 10:9.

Example 2

FIGS. 38A-38D show transmission electron micrographs (TEM) of various combinations of CATCH peptides. Scale bar=0.1 μm. TEM micrographs and combinations of CATCH peptides were obtained using methods previously described in Example 1.

Figure 39A:
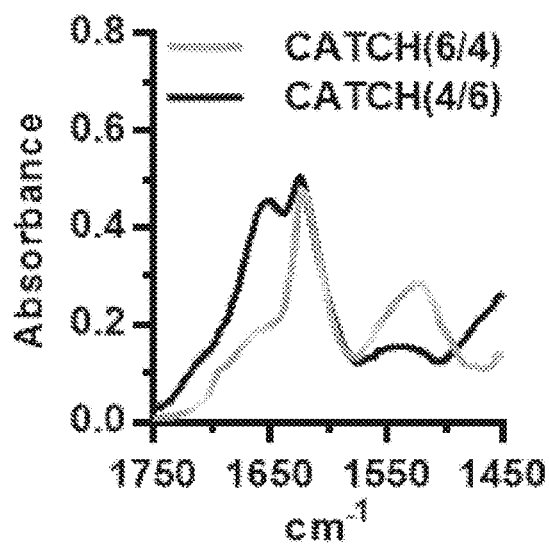
FIGS. 39A-39B show graphs demonstrating Fourier transform infrared spectra for all combinations of CATCH peptide pairs at 5 mM.
Figure 39B:
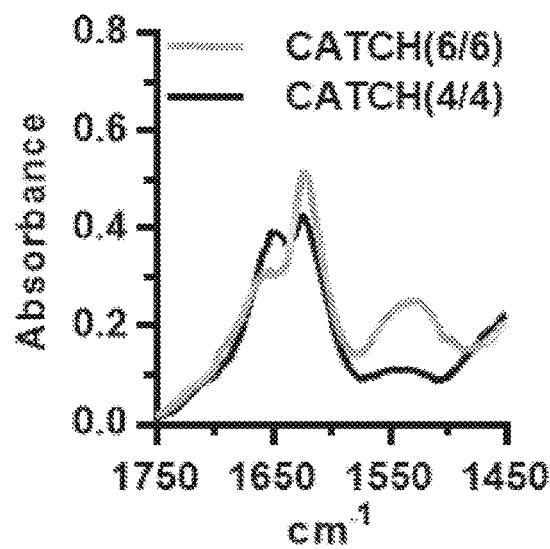
Figures 41A, 41B, 41C, 41D:
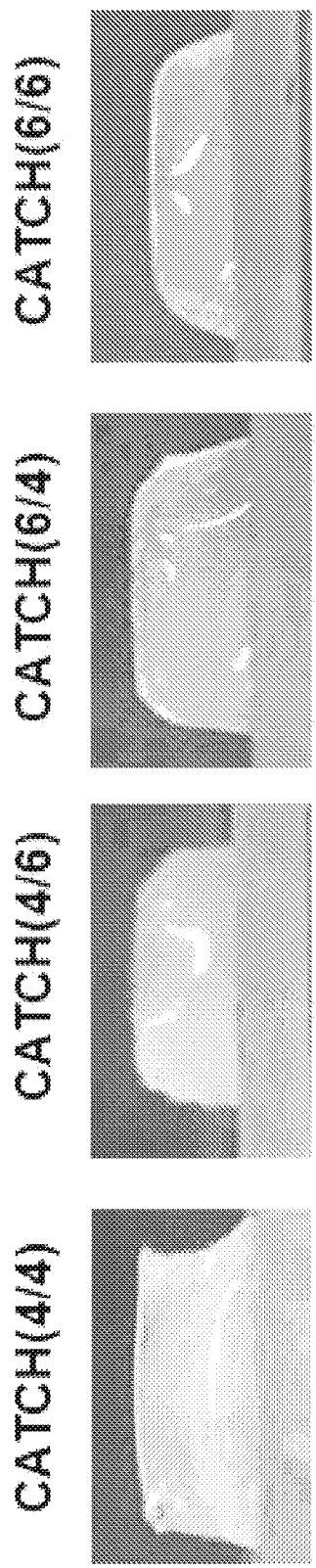
FIGS. 41A-41D show images of macroscopic self-supporting hydrogels formed by different CATCH combinations.

FIGS. 39A-39B show graphs demonstrating Fourier transform infrared spectra (FTIR) for all combinations of CATCH peptide pairs at 5 mM. The FTIR spectra were recorded on a Frontier FTIR spectrophotometer (PerkinElmer) using the universal ATR sampling accessory. 1 μl of 5 mM peptide solution was placed onto the ATR sampling accessory and allowed to dry. Samples were run 4 times with the average of the spectra reported.

FIGS. 40A-40B show graphs demonstrating ThT end-point analysis (FIG. 40A) and ThT kinetic analysis (FIG. 40B) of different CATCH combinations. The ThT end-point analysis was performed using methods and techniques previously described in Example 1.

FIGS. 41A-41D show images of macroscopic self-supporting hydrogels formed by different CATCH combinations. Briefly, self-supporting hydrogels from stock solutions of CATCH peptides were prepared by dissolving lyophilized peptides in water then diluting with 10× PBS to reach a final concentration of 10 mM peptide and 1× PBS. Peptide solutions were mixed on a Sigmacote-coated microscope slide, then shaped by placing another Sigmacote-coated microscope slide on top of the peptide solution separated by a spacer. Hydrogels were incubated for 18 hours before removal of the top microscope slide.

FIGS. 42A-42H show images and graphs demonstrating the characterization of CATCH-GFP fusion proteins and their integration into CATCH fibers. Briefly, 500 μM CATCH(4/4) nanofiber sedimentation in the presence of (FIG. 42A) ThT, (FIG. 42B) CATCH(6-)GFP, (FIG. 42C) mCATCH(6-)GFP. FIG. 42D shows a graph demonstrating quantification of protein remaining in supernatant (i.e., not integrated into CATCH nanofibers) after nanofiber sedimentation. 500 μM CATCH(6/6) nanofiber sedimentation in the presence of (FIG. 42E) ThT, (FIG. 42F) CATCH(6-) GFP, (FIG. 42G) mCATCH(6-)GFP. FIG. 42H shows a graph demonstrating quantification of protein remaining in supernatant (i.e., not integrated into CATCH nanofibers) after nanofiber sedimentation. Together, these data demonstrate that CATCH(6-) integrates into both CATCH(6/6) and CATCH(4/4) nanofibers in a CATCH-dependent manner.

Figures 43A, 43B:
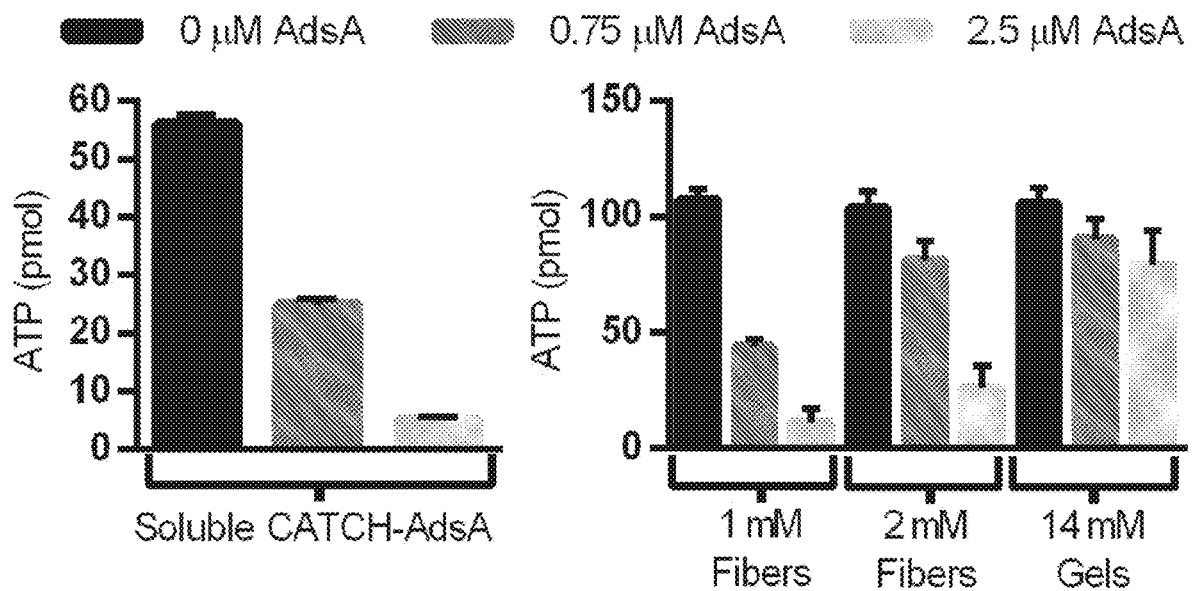
FIGS. 43A-43B show graphs demonstrating ATP turnover by soluble CATCH-Adenosine Synthase A (AdsA) (FIG. 43A) and CATCH-AdsA integrated at CATCH peptide concentrations of 1 mM, 2 mM, and 14 mM (FIG. 43B).

FIGS. 43A-43B show graphs demonstrating ATP turnover by soluble CATCH-Adenosine Synthase A (AdsA) (FIG. 43A) and CATCH-AdsA integrated at CATCH peptide concentrations of 1 mM, 2 mM, and 14 mM (FIG. 43B). Briefly, to quantify ATP turnover, soluble CATCH-AdsA or CATCH-AdsA integrated in CATCH fibers were mixed with ATP in 1× PBS and incubated for 15 minutes in a 96 well plate. Samples were diluted 1:10 with a stock solution made from the ATP Determination Kit (ThermoFisher) as directed. ATP quantification was determined through luminescence using a SpectraMax M3 spectrophotometer.

Figure 44:
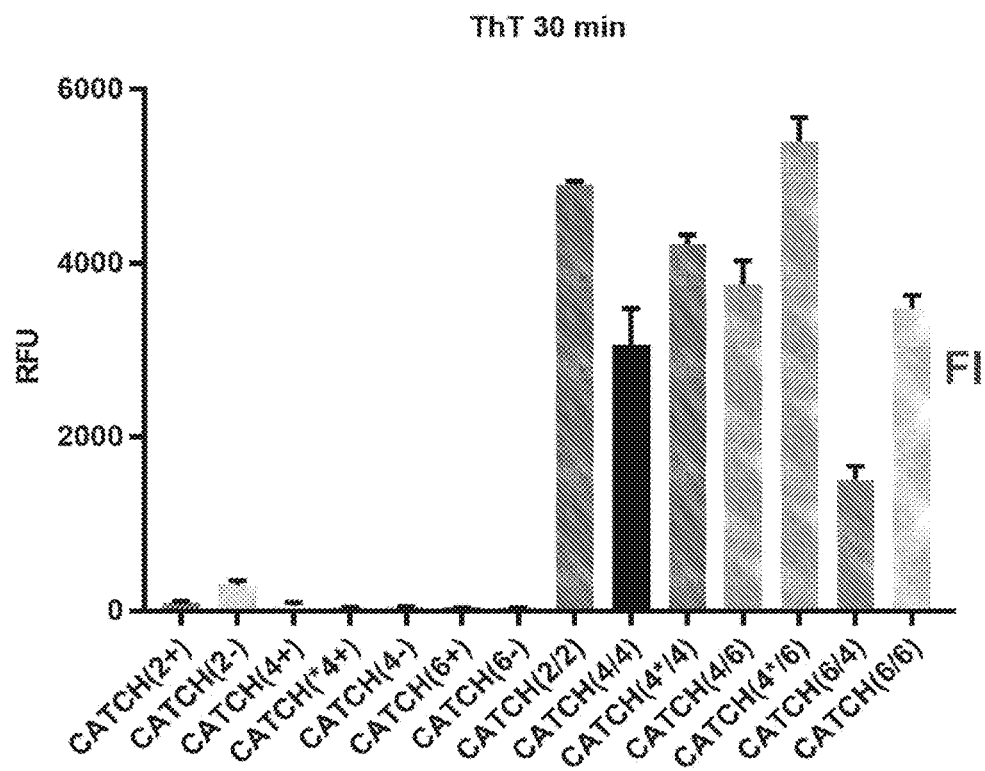
FIG. 44 shows a graph demonstrating the results from an endpoint analysis of ThT after about 30 minutes. A large increase in relative fluorescent units (RFU) from a peptide is indicative of co-assembly into β-sheet nanofibers.
Figure 45A:
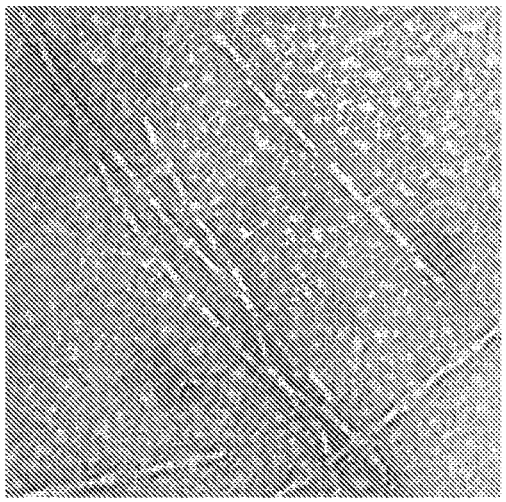
FIGS. 45A-45D show transmission electron microscope (TEM) images of CATCH variant combinations that can demonstrate β-sheet nanofibers.
Figure 45B:
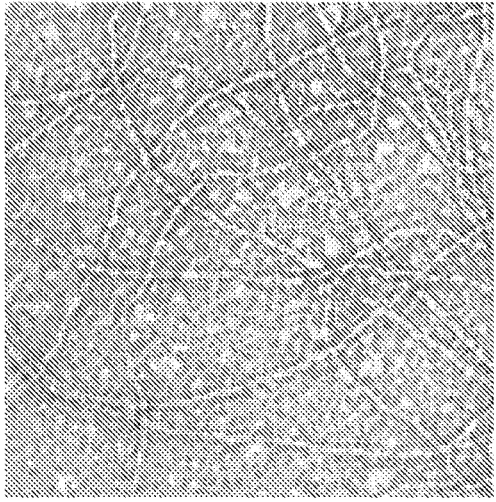
Figure 45C:
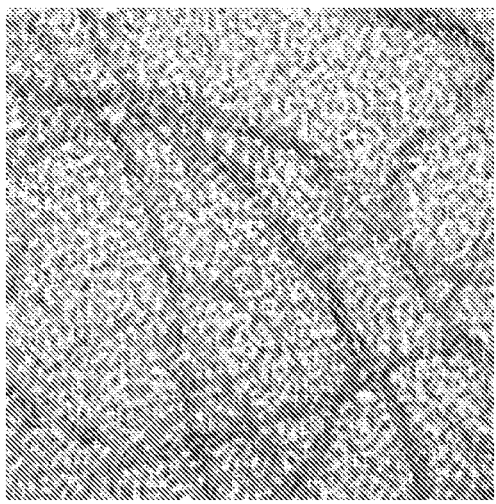
Figure 45D:
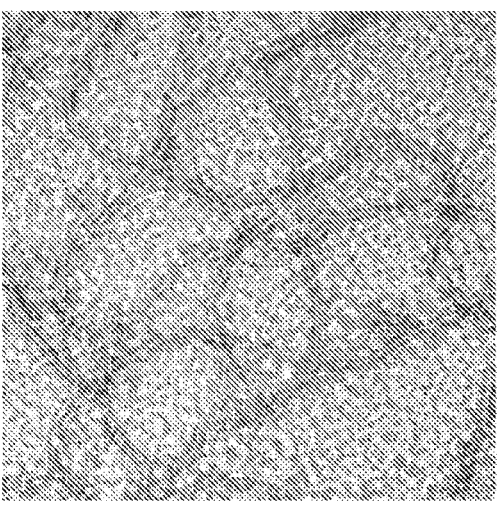
Figure 46A:
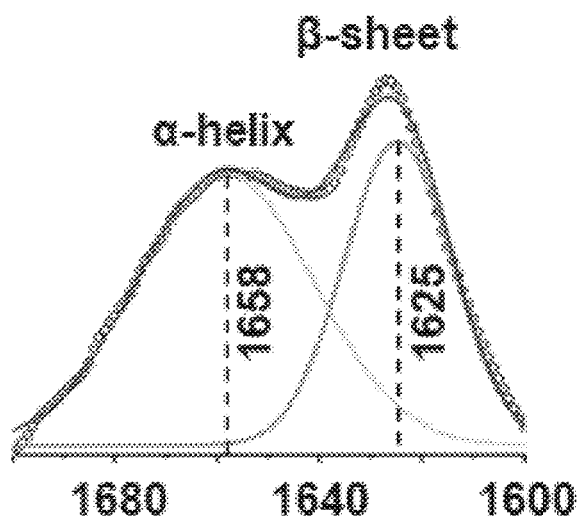
FIGS. 46A-46F show graphs that demonstrate Fourier transform infrared spectroscopy spectra of various CATCH assemblies demonstrating secondary structures.
Figure 46B:
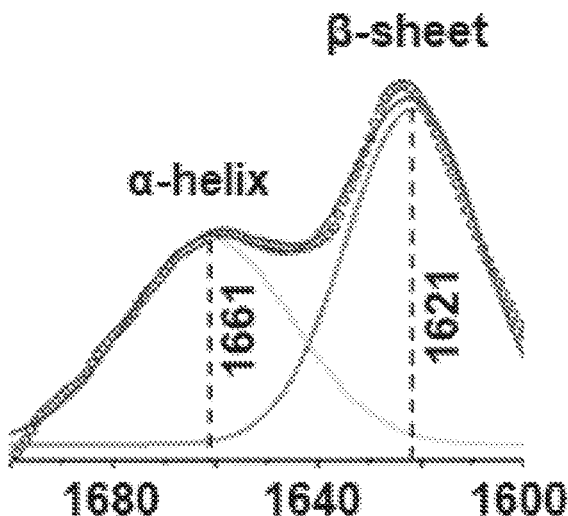
Figure 46C:
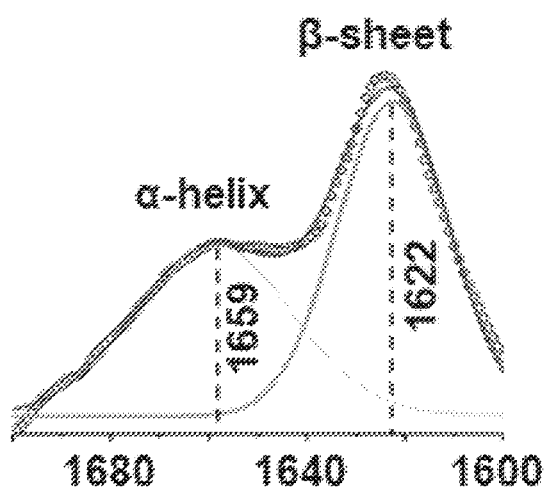
Figure 46D:
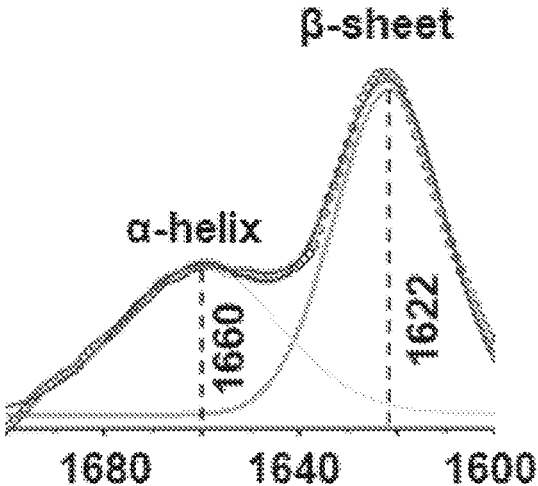
Figures 46E, 46F:
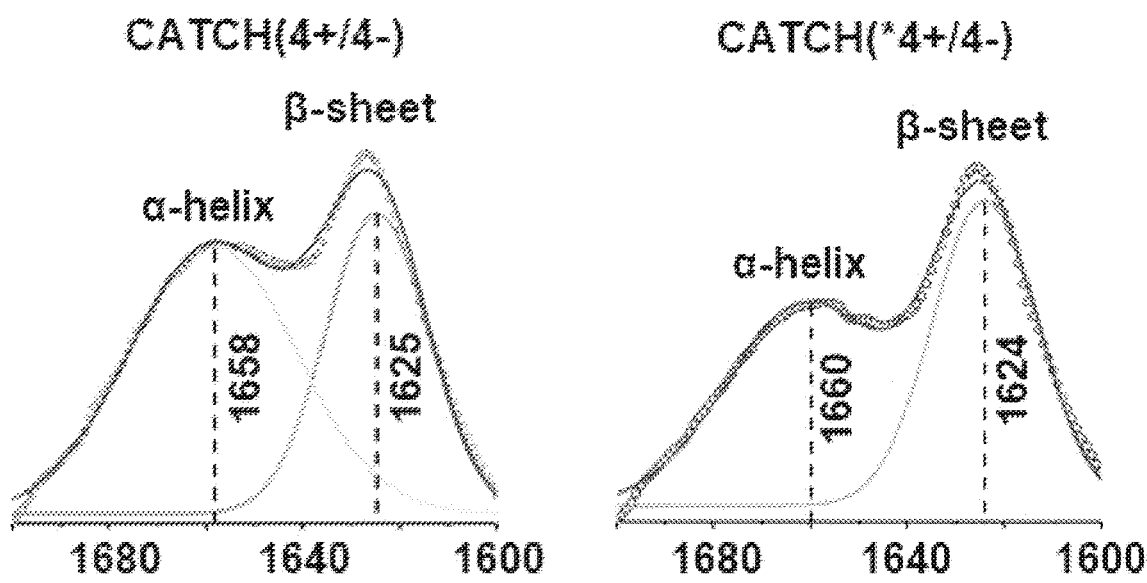

FIG. 44 shows a graph demonstrating the results from an endpoint analysis of ThT after about 30 minutes. A large increase in relative fluorescent units (RFU) from a peptide is indicative of co-assembly into β-sheet nanofibers. Briefly, a ThT stock solution containing 0.8 mg/ml of thioflavin T (Acros) in 1× phosphate-buffered saline (PBS) (137 mM NaCl, 2.7 mM KCl, 10 mM $Na_2HPO_4$ and 1.8 mM $KH_2PO_4$, pH 7.4) was filtered through a 0.22 μm syringe filter (Millex), and further diluted 1:10 with 1× PBS to create a working solution. Peptide samples were mixed with the ThT working solution at a 1:10 (v/v) ratio, added to a black 96-well plate (Corning), and analyzed with a Molecular Devices SpectraMax M3 spectrophotometer (excitation 450, emission 482 nm). All samples were run in triplicate, with the mean and standard deviation of these samples reported.

FIGS. 45A-45D show transmission electron microscope (TEM) images of CATCH variant combinations that can demonstrate β-sheet nanofibers. Briefly, Formvar-carbon coated 400 mesh copper grids (FCF400-CU-UB, EMS) were floated on top of 20 μL of 1× PBS solutions containing CATCH peptides with or without CATCH(-)GFP, and then dried by tilting the grid on a Kimwipe. Samples were negatively stained with 2% uranyl acetate in water, and analyzed using a Hitachi H-7000.

FIGS. 46A-46F show graphs that demonstrate Fourier transform infrared spectroscopy spectra of various CATCH assemblies demonstrating secondary structures. Briefly, fourier transform infrared spectra (FTIR) for all combinations of CATCH peptide pairs were run at 5 mM. The FTIR spectra were recorded on a Frontier FTIR spectrophotometer (PerkinElmer) using the universal ATR sampling accessory. 1 μl of 5 mM peptide solution was placed onto the ATR sampling accessory and allowed to dry. Samples were run 4 times with the average of the spectra reported.

Example 3

Multiple CATCH peptides can be produced from a single synthetic gene that encodes a polypeptide containing multiple CATCH peptides that separated from each other by a flanking protease cleavage amino acid sequence. The synthetic gene can include DNA segments that each encode a CATCH peptide that are separated in the synthetic gene by DNA segments that can each encode a protease cleavage sequence. This can allow for scalable production of the CATCH peptides.

FIG. 47 shows a schematic demonstrating an embodiment of an expression system that can be used to produce CATCH peptides. As show CATCH peptide regions with flanking TEVc (TEV protease cut site ENKFQ/S (SEQ ID NO: 42)) can be produced from a synthetic gene encoding the polypeptide by expression from a suitable expression vector in a suitable host cell (e.g. *E. coli*). The polypeptide can also include a suitable purification tag. The tag included in the embodiment shown in FIG. 47 can be His. The produced polypeptide can be recovered, and purified using immobilized affinity chromatography. The polypeptide can then be broken down into its individual peptides (positive and negative CATCH peptides). The separated peptides can be purified using immobilized affinity chromatography, reversed-phase chromatography, ion-exchange chromatography, or size-exclusion chromatography. While any CATCH sequence being included in the gene as described above, some exemplary sequences demonstrating splitting of the protease cleavage cite are demonstrated by SQQKFKFKFKQQENLYEQ (SEQ ID NO: 9), SQQKFKFKFKQQWENLYFQ (SEQ ID NO: 10), and SEQEFEFEFEQEWENLYFQ (SEQ ID NO: 11). Any CATCH sequence can be placed between the two portions of the protease cleavage site (S/ENLYFQ (SEQ ID NO: 43)).

Figure 48:
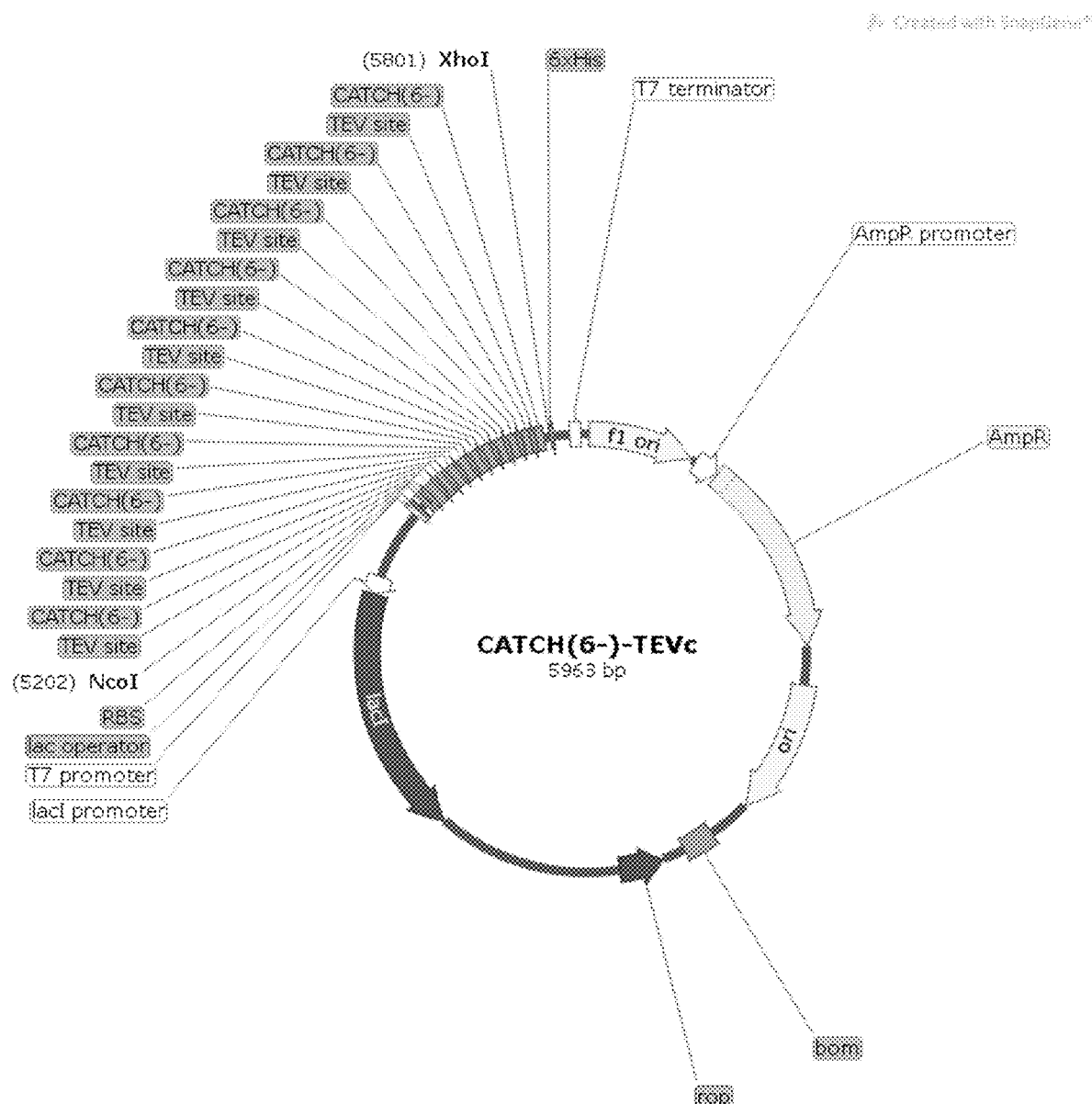
FIG. 48 shows an embodiment of an expression vector that can be used for expression of one or more CATCH peptides (CATCH 6- shown) with a cleavable linker between each CATCH peptide sequence in the vector.
Figure 49:
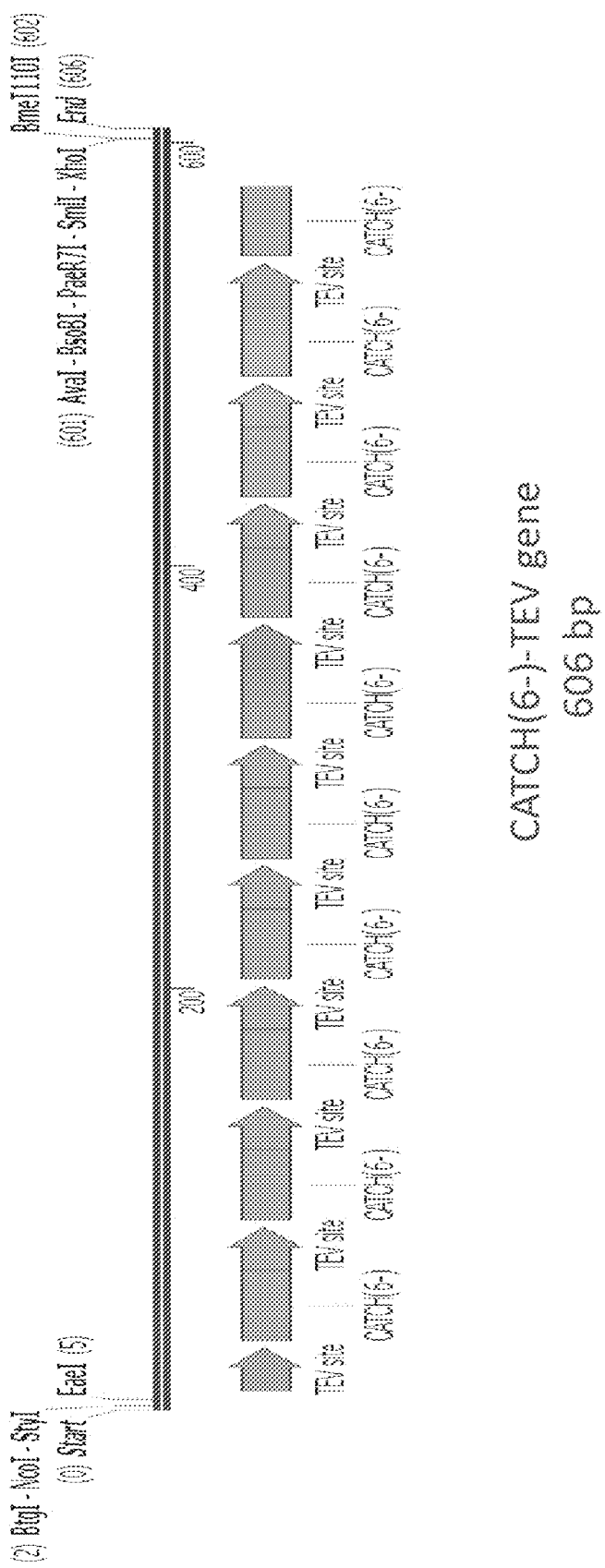
FIG. 49 shows a diagram of an embodiment of a CATCH gene with at least two CATCH peptide sequences (CATCH 6- shown) separated by cleavable linkers that can be expressed from a vector, such as that shown in FIG. 48.

FIG. 48 shows an embodiment of an expression vector that can be used for expression of one or more CATCH peptides (CATCH 6- shown) with a cleavable linker between each CATCH peptide sequence in the vector. FIG. 49 shows a diagram of an embodiment of a CATCH gene with at least two CATCH peptide sequences (CATCH 6- shown) separated by cleavable linkers that can be expressed from a vector, such as that shown in FIG. 48.

Figure 50B:
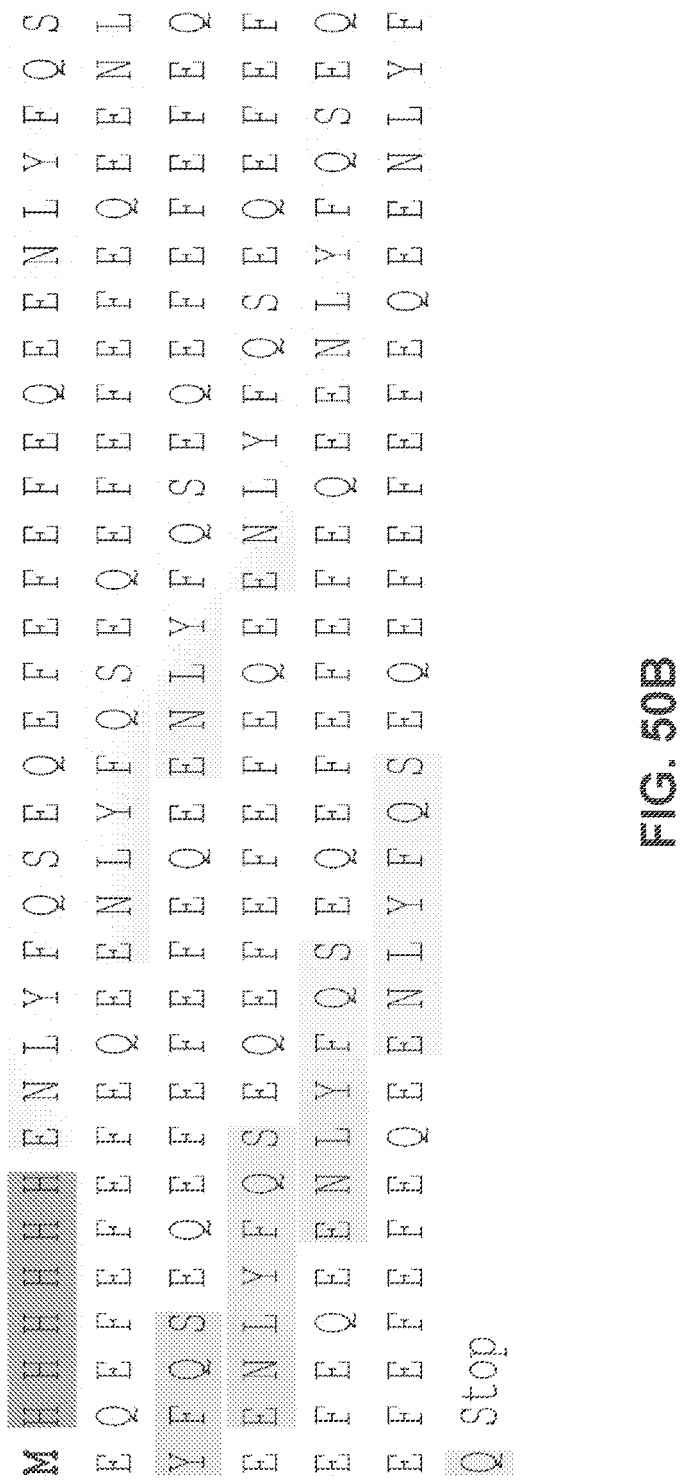

FIGS. 50A-50C show DNA sequence (FIG. 50A) that can encode an amino acid sequence (FIG. 50B) of a CATCH(6-) -. The DNA sequence of FIG. 50A can be recombinantly expressed in an expression vector to produce the protein sequence of FIG. 50B. FIG. 50C. shows a table of some of the specific features of the DNA sequence of FIG. 50A and the polypeptide of FIG. 50B.

Figure 51:
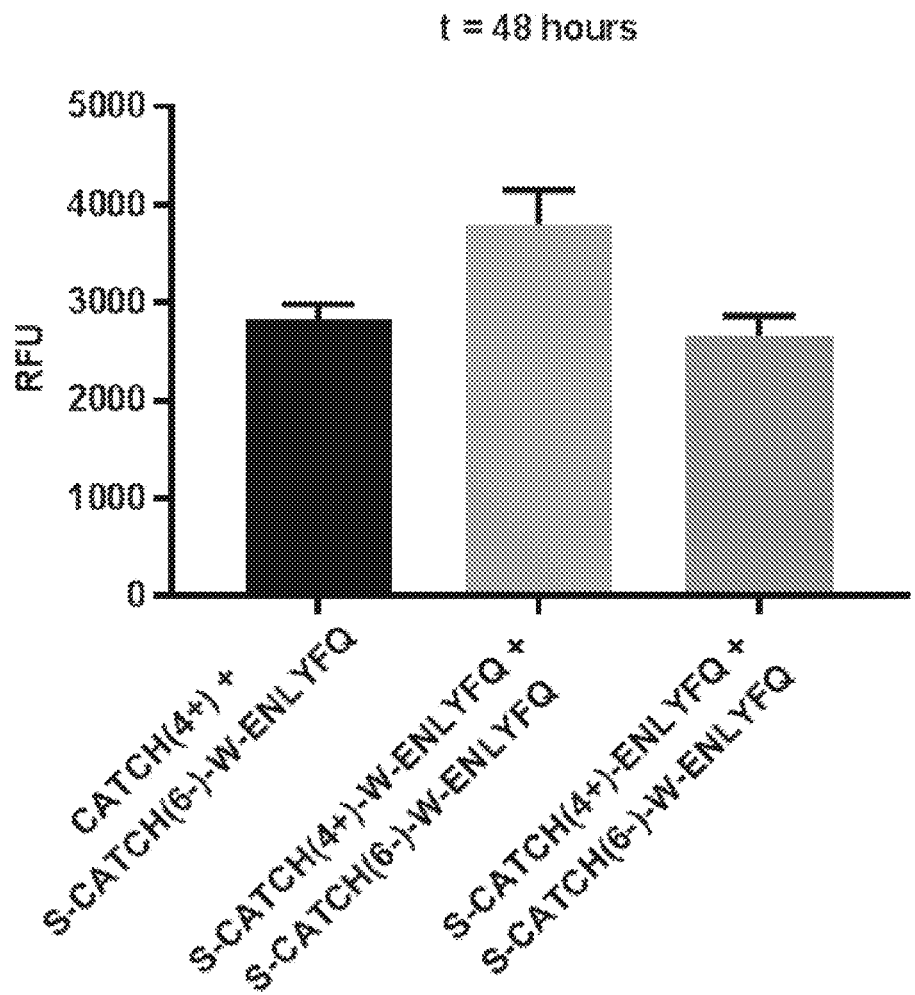
FIG. 51 shows a graph that demonstrates results from an endpoint ThT study of CATCH peptides with an appended TEVc linker. An RFU signal of this strength can indicate β-sheet amyloid formation.

FIG. 51 shows a graph that demonstrates results from an endpoint ThT study of CATCH peptides with an appended TEVc linker. An RFU signal of this strength can indicate β-sheet amyloid formation. Briefly, a ThT stock solution containing 0.8 mg/ml of thioflavin T (Acros) in 1× phosphate-buffered saline (PBS) (137 mM NaCl, 2.7 mM KCl, 10 mM $Na_2HPO_4$ and 1.8 mM $KH_2PO_4$, pH 7.4) was filtered through a 0.22 μm syringe filter (Millex), and further diluted 1:10 with 1× PBS to create a working solution. Peptide samples were mixed with the ThT working solution at a 1:10 (v/v) ratio, added to a black 96-well plate (Corning), and analyzed with a Molecular Devices SpectraMax M3 spectrophotometer (excitation 450, emission 482 nm). All samples were run in triplicate, with the mean and standard deviation of these samples reported.

Figure 52A:
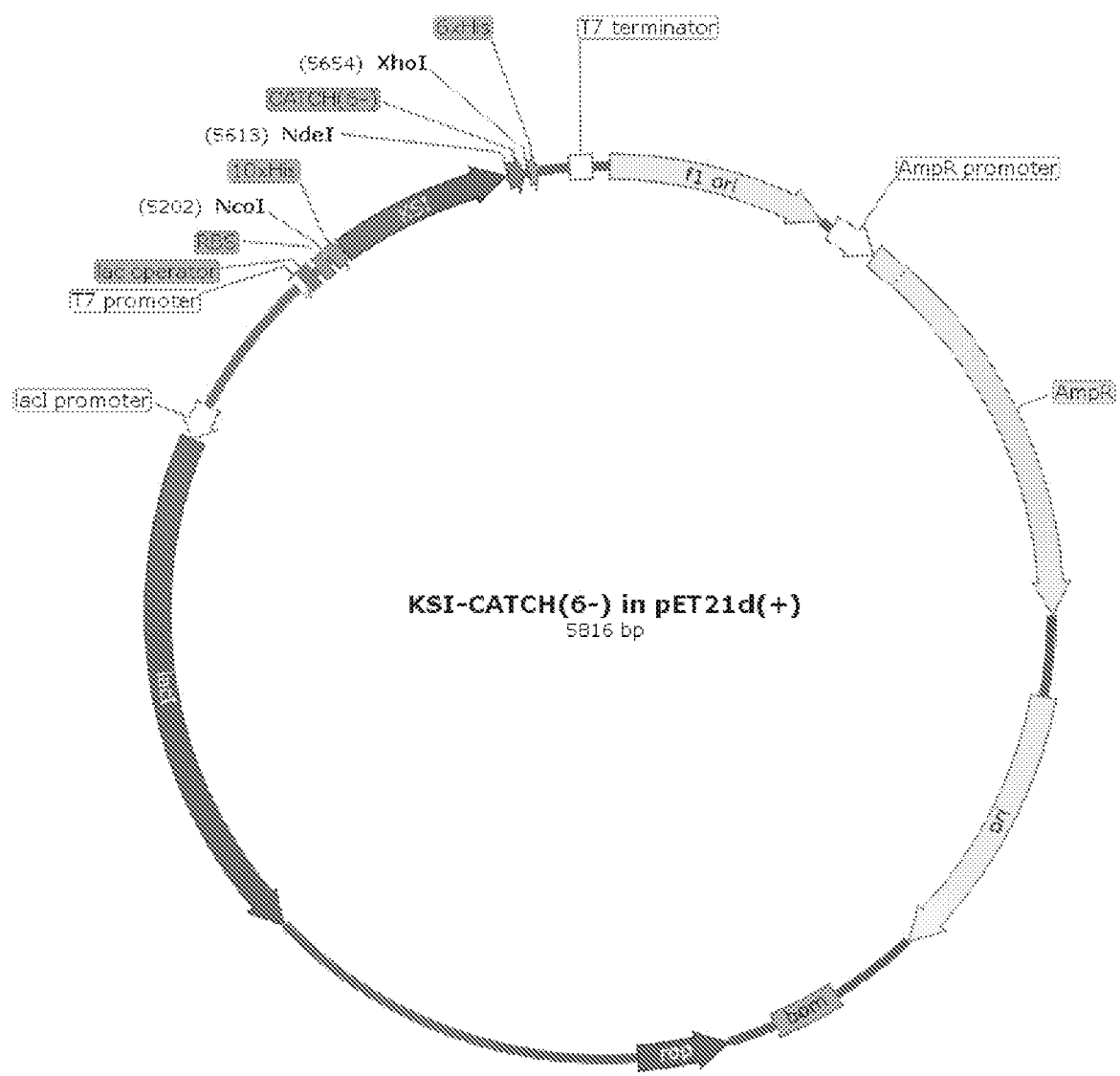
FIGS. 52A-52B show an expression vector (FIG. 52A) that can contain an KSI (kerosteroid isomerase), which can be a carrier protein for the CATCH peptide sequence and can be separable by including, for example, a methionine residue before the first amino acid of the CATCH peptide and cleaving with CNBr; and an image of an SDS-PAGE gel demonstrating the KSI-CATCH(6-) protein at the correct molecular weight (about 16.5 kDa) after expression and separation by CNBr treatment.
Figure 52B:
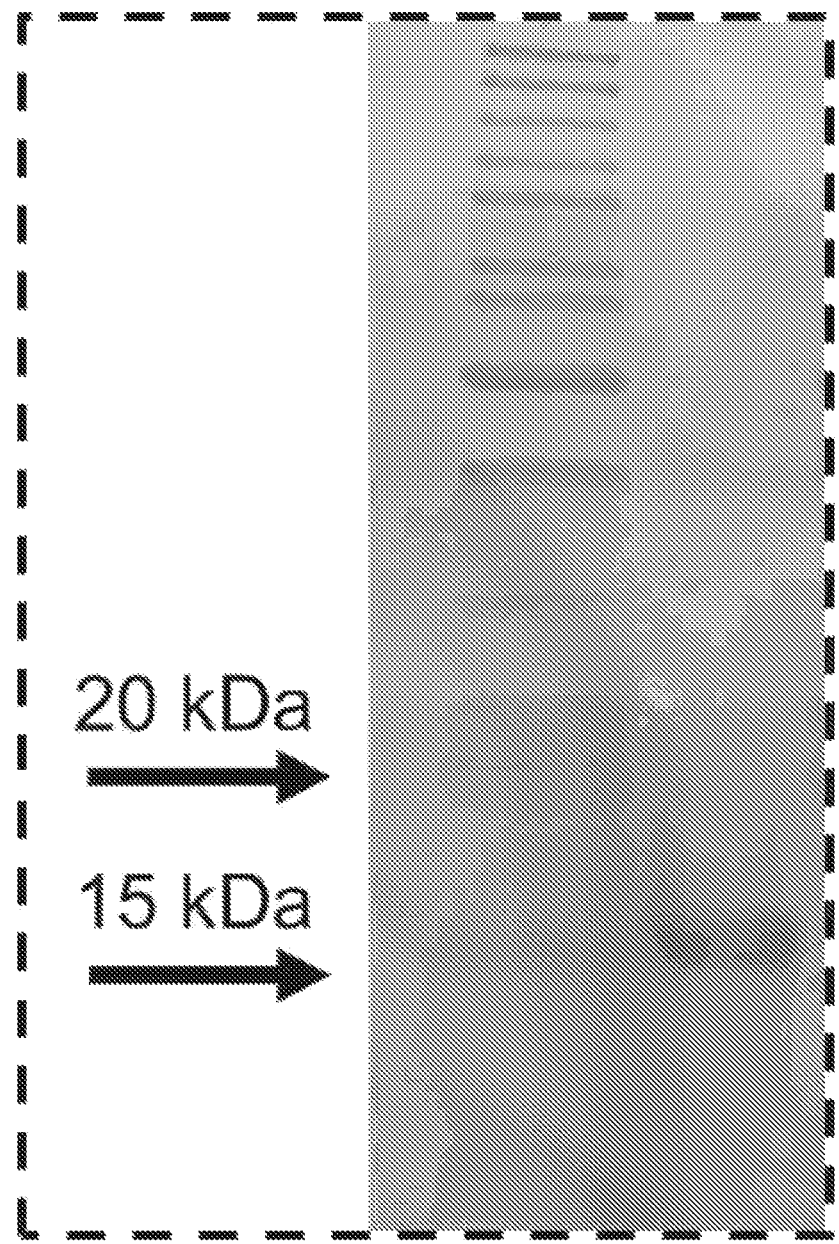

FIGS. 52A-52B show an expression vector (FIG. 52A) that can contain an KSI (kerosteroid isomerase), which can be a carrier protein for the CATCH peptide sequence and can be separable by including, for example, a methionine residue before the first amino acid of the CATCH peptide and cleaving with CNBr; and an image of an SDS-PAGE gel demonstrating the KSI-CATCH(6-) protein at the correct molecular weight (about 16.5 kDa) after expression and separation by CNBr treatment.

FIGS. 53A-53B shows a DNA sequence (FIG. 53A) and the encoded KSI-CATCH(6-) polypeptide (FIG. 53B), where CATCH(6-) can be replaced with any CATCH peptide. FIG. 53C shows a table with some of the features of the DNA sequence of FIG. 53A and the polypeptide of FIG. 53B.

We claim:

1. A set of charge complementary self-assembling peptides coupled to at least one Adenosine Synthase A (AdsA) through the N-terminus or C-terminus of at least one peptide of the set of charge complementary peptides, wherein the set of charge complementary peptides comprises:
   a positive peptide comprising at least 3 amino acids ($A_3$-$A_1$, as set forth sequentially from N-terminus to C-terminus), wherein $A_3$, $A_2$, and $A_1$ are each independently selected from a positively charged amino acid and a hydrophobic amino acid, and wherein at least one amino acid of $A_3$-$A_1$ is a positively charged amino acid and at least one amino acid of $A_3$-$A_1$ is a hydrophobic amino acid; and
   a negative peptide having a sequence selected from the group consisting of SEQ ID NOs: 2, 4, or 7.

2. The set of charge complementary self-assembling peptides of claim 1,
   wherein the positive peptide comprises at least 4 amino acids ($A_4$-$A_1$, as set forth sequentially from N-terminus to C-terminus), wherein $A_4$, $A_3$, $A_2$, and $A_1$, are each independently selected from a positively charged amino acid and a hydrophobic amino acid, and wherein at least one amino acid of $A_4$-$A_1$ is a positively charged amino acid and at least one amino acid of $A_4$-$A_1$ is a hydrophobic amino acid.

3. The set of charge complementary self-assembling peptides of claim 1,
   wherein the positive peptide comprises at least 5 amino acids ($A_5$-$A_1$, as set forth sequentially from N-terminus to C-terminus), wherein $A_5$, $A_4$, $A_3$, $A_2$, and $A_1$, are each independently selected from a positively charged amino acid and a hydrophobic amino acid, and wherein at least one amino acid of $A_5$-$A_1$ is a positively charged amino acid and at least one amino acid of $A_5$-$A_1$ is a hydrophobic amino acid.

4. The set of charge complementary self-assembling peptides of claim 1,
   wherein the positive peptide comprises at least 7 amino acids ($A_7$-$A_1$, as set forth sequentially from N-terminus to C-terminus), wherein $A_7$, $A_6$, $A_5$, $A_4$, $A_3$, $A_2$, and $A_1$, are each independently selected from a positively charged amino acid and a hydrophobic amino acid, and wherein at least one amino acid of $A_7$-$A_1$ is a positively charged amino acid and at least one amino acid of $A_7$-$A_1$ is a hydrophobic amino acid.

5. The set of charge complementary self-assembling peptides of claim 1,
   wherein the positive peptide comprises at least 11 amino acids ($A_{11}$-$A_1$ as set forth sequentially from N-terminus to C-terminus), wherein:
   $A_{11}$, $A_9$, $A_7$, and $A_5$ are each independently selected from a polar amino acid or a positively charged amino acid;
   $A_{10}$ is a polar amino acid;
   $A_8$, $A_6$, $A_4$, and $A_2$ are each a hydrophobic amino acid; and
   $A_3$ and $A_1$ are each a positively charged amino acid.

6. The set of charge complementary self-assembling peptides of claim 1,
   wherein the positive peptide has a sequence selected from the group consisting of SEQ ID NO: 1, 3, 5, 6, or 8.

7. The set of charge complementary self-assembling peptides of claim 1, wherein the peptides self-assemble in an aqueous solution having a pH of about 6.5 to about 8.5.

8. The set of charge complementary self-assembling peptides of claim 1, wherein the positive peptide, the negative peptide, or each the positive and the negative peptide, further comprise one or more cargo polypeptides.

9. The set of charge complementary self-assembling peptides of claim 1, wherein the positively charged amino acids are each independently selected from the group consisting of: arginine (R), histidine (H), and lysine (K), and wherein the hydrophobic amino acids are each independently selected from the group consisting of: alanine (A), glycine (G), isoleucine (I), leucine (L), methionine (M), phenylalanine (F), tryptophan (W), tyrosine (Y), and valine (V).

10. A supramolecular structure comprising the set of charge complementary self-assembling peptides of claim 1, wherein the positive and the negative-peptide are attached to each other via electrostatic interactions.

11. A set of charge complementary self-assembling peptides coupled to at least one Adenosine Synthase A (AdsA) through the N-terminus or C-terminus of at least one peptide of the set of charge complementary peptides, wherein the set of charge complementary peptides comprises:
    a negative peptide comprising at least 3 amino acids ($B_3$-$B_1$, as set forth sequentially from N-terminus to C-terminus), wherein $B_3$, $B_2$, and $B_1$ are each independently selected from a negatively charged amino acid and a hydrophobic amino acid, and wherein at least one amino acid of $B_3$-$B_1$ is a negatively charged amino acid and at least one amino acid of $B_3$-$B_1$ is a hydrophobic amino acid; and
    a positive peptide having a sequence selected from the group consisting of SEQ ID NOs: 1, 3, 5, 6, or 8.

12. The set of charge complementary self-assembling peptides of claim 11, wherein the negative peptide comprises at least 4 amino acids ($B_4$-$B_1$, as set forth sequentially from N-terminus to C-terminus),
    wherein $B_4$, $B_3$, $B_2$, and $B_1$ are each independently selected from a negatively charged amino acid and a hydrophobic amino acid, and wherein at least one amino acid of $B_4$-$B_1$ is a negatively charged amino acid and at least one amino acid of $B_4$-$B_1$ is a hydrophobic amino acid.

13. The set of charge complementary self-assembling peptides of claim 11, wherein the negative peptide comprises at least 5 amino acids ($B_5$-$B_1$, as set forth sequentially from N-terminus to C-terminus),
    wherein $B_5$, $B_4$, $B_3$, $B_2$, and $B_1$ are each independently selected from a negatively charged amino acid and a hydrophobic amino acid, and wherein at least one amino acid of $B_5$-$B_1$ is a negatively charged amino acid and at least one amino acid of $B_5$-$B_1$ is a hydrophobic amino acid.

14. The set of charge complementary self-assembling peptides of claim 11, wherein the negative peptide comprises at least 7 amino acids ($B_7$-$B_1$, as set forth sequentially from N-terminus to C-terminus), wherein $B_7$, $B_6$, $B_5$, $B_4$, $B_3$, $B_2$, and $B_1$ are each independently selected from a negatively charged amino acid and a hydrophobic amino acid, and wherein at least one amino acid of $B_7$-$B_1$ is a negatively charged amino acid and at least one amino acid of $B_7$-$B_1$ is a hydrophobic amino acid.

15. The set of charge complementary self-assembling peptides of claim 11, wherein the negative peptide comprises at least 11 amino acids ($B_{11}$-$B_1$ as set forth sequentially from N-terminus to C-terminus), wherein:

$B_{11}$, $B_9$, $B_7$, and $B_5$ are each independently selected from a polar amino acid or a negatively charged amino acid;

$B_{10}$ is a polar amino acid;

$B_8$, $B_6$, $B_4$, and $B_2$ are each a hydrophobic amino acid; and $B_3$ and $B_1$ are each a negatively charged amino acid.

16. The set of charge complementary self-assembling peptides of claim 11, wherein the negative peptide has a sequence selected from the group consisting of SEQ ID NO: 2, 4, or 7.

17. The set of charge complementary self-assembling peptides of claim 11, wherein the peptides self-assemble in an aqueous solution having a pH of about 6.5 to about 8.5.

18. The set of charge complementary self-assembling peptides of claim 11, wherein the positive peptide, the negative peptide, or each the positive and the negative peptide, further comprise one or more cargo polypeptides.

19. The set of charge complementary self-assembling peptides of claim 11, wherein the negatively charged amino acids are each independently selected from the group consisting of: aspartate (D) and glutamate (E), and wherein the hydrophobic amino acids are each independently selected from the group consisting of: alanine (A), glycine (G), isoleucine (I), leucine (L), methionine (M), phenylalanine (F), tryptophan (W), tyrosine (Y), and valine (V).

20. A supramolecular structure comprising the set of charge complementary self-assembling peptides of claim 11, wherein the positive and the negative-peptide are attached to each other via electrostatic interactions.

\* \* \* \* \*